United States Patent
Raines et al.

(10) Patent No.: US 9,738,664 B2
(45) Date of Patent: Aug. 22, 2017

(54) BORONIC ACID INHIBITORS OF HIV PROTEASE

(71) Applicant: WISCONSIN ALUMNI RESEARCH FOUNDATION, Madison, WI (US)

(72) Inventors: Ronald T. Raines, Madison, WI (US); Ian Windsor, Wisconsin Rapids, WI (US); Michael Palte, Melrose, MA (US); John Lukesh, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/927,390

(22) Filed: Oct. 29, 2015

(65) Prior Publication Data

US 2016/0122366 A1    May 5, 2016

Related U.S. Application Data

(60) Provisional application No. 62/072,367, filed on Oct. 29, 2014.

(51) Int. Cl.
| | | |
|---|---|---|
| *A61K 31/34* | (2006.01) | |
| *A61K 31/69* | (2006.01) | |
| *C07F 5/02* | (2006.01) | |
| *A61K 31/427* | (2006.01) | |
| *A61K 31/00* | (2006.01) | |

(52) U.S. Cl.
CPC .............. *C07F 5/025* (2013.01); *A61K 31/00* (2013.01); *A61K 31/34* (2013.01); *A61K 31/427* (2013.01); *A61K 31/69* (2013.01)

(58) Field of Classification Search
CPC .......... C07F 5/025; A61K 31/34; A61K 31/69
See application file for complete search history.

(56) References Cited

U.S. PATENT DOCUMENTS

| | | | |
|---|---|---|---|
| 5,196,438 A | 3/1993 | Martin et al. | |
| 5,413,999 A | 5/1995 | Vacca et al. | |
| 5,484,801 A | 1/1996 | Al-Razzak et al. | |
| 5,484,926 A | 1/1996 | Dressman et al. | |
| 5,585,397 A | 12/1996 | Tung et al. | |
| 5,744,481 A | 4/1998 | Vazquez et al. | |
| 5,786,483 A | 7/1998 | Vazquez et al. | |
| 5,843,946 A | 12/1998 | Vazquez et al. | |
| 5,849,911 A | 12/1998 | Fassler et al. | |
| 5,852,195 A | 12/1998 | Romines et al. | |
| 5,856,353 A | 1/1999 | Tung et al. | |
| 5,914,332 A | 6/1999 | Sham et al. | |
| 5,968,942 A | 10/1999 | Vazquez et al. | |
| 6,060,476 A | 5/2000 | Vazquez et al. | |
| 6,169,181 B1 | 1/2001 | Romines et al. | |
| 6,248,775 B1 | 6/2001 | Vazquez et al. | |
| 6,372,778 B1 | 4/2002 | Tung et al. | |
| 6,417,387 B1 | 7/2002 | Vazquez et al. | |
| 6,436,989 B1 | 8/2002 | Hale et al. | |
| 6,472,407 B1 | 10/2002 | Vazquez et al. | |
| 6,500,832 B1 | 12/2002 | Vazquez et al. | |
| 6,646,010 B2 | 11/2003 | Vazquez et al. | |
| 6,924,286 B1 | 8/2005 | Vazquez et al. | |
| 7,608,632 B2 | 10/2009 | Tung et al. | |
| 7,981,929 B2 | 7/2011 | Eissenstat | |
| 8,318,983 B2 | 11/2012 | Burke et al. | |
| 8,557,980 B2 | 10/2013 | Burke et al. | |
| 8,722,916 B2 | 5/2014 | Duncton et al. | |
| 2006/0172936 A1 | 8/2006 | Hale et al. | |
| 2007/0010489 A1 | 1/2007 | Arimilli et al. | |
| 2009/0325903 A1 | 12/2009 | Elliot et al. | |
| 2010/0093811 A1 | 4/2010 | Coburn et al. | |
| 2010/0256092 A1 | 10/2010 | Xia et al. | |
| 2013/0196433 A1 | 8/2013 | Raines et al. | |
| 2014/0206648 A1 | 7/2014 | Reddy et al. | |

OTHER PUBLICATIONS

Albers et al. (2010) "Discovery and Optimization of Boronic Acid Based Inhibitors of Autotaxin," J. Med. Chem. 53(13):4958-4967.
Albers et al. (May 26, 2011) "Structure-Based Design of Novel Boronic Acid-Based Inhibitors of Autotaxin," J. Med. Chem. 54(13):4619-4626.
Altman et al. (2008) "HIV-1 protease inhibitors from inverse design in the substrate envelope exhibit subnanomolar binding to drug-resistant variants," J. Am. Chem. Soc. 130:6099-6113.
Dembitsky (2003) "Synthesis and Biological Activity of α-Aminoboronic Acids, Amine-Carboxyboranes and Their Derivatives," Tetrahedron. 59(5):579-593.
Ghosh et al. (2006) "Structure-based design of novel HIV-1 protease inhibitors to combat drug resistance," J. Med. Chem. 49:5252-5261.
Gillis et al. (2007) "A Simple and Modular Strategy for Small Molecule Synthesis: Iterative Suzuli-Miyaura Coupling of B-Protected Haloboroanic Acid Building Blocks," J. Am. Chem. Soc. 129:6716-6717.
Gillis et al. (2009) "Iterative Cross-Coupling with NIDA Boronates: towards a General Strategy for Small-Molecule Synthesis," Aldrichimica Acta. 42:17-27.
Honda et al. (2004) "New approaches to the industrial synthesis of HIV protease inhibitors," Org. Biomol. Chem. 2:2061-2070.
International Search Report with Written Opinion corresponding to International Patent Application No. PCT/US2015/058164, mailed Jan. 21, 2016.
Knapp et al. (2009) "A General Solution for Unstable Boronic Acids: Slow-Release Cross-Coupling from Air-Stable MIDA Boronates," J. Am. Chem. Soc. 131:6961-6963.
Mancilla et al. (1986) "New bicyclic organylboronic esters derived from iminodiacetic acids," J. Organomet. Chem. 307:1-6.
Matteson (2007) "α-Amido boronic acids: A synthetic challenge and their properties as serine protease inhibitors," Med. Res. Review. 28(2)233-246.

(Continued)

*Primary Examiner* — Yong Chong
(74) *Attorney, Agent, or Firm* — Lathrop & Gage LLP

(57) ABSTRACT

Protease inhibitors, particularly aspartyl protease inhibitors, and more particularly HIV protease inhibitors which are boronated to enhance activity or to enhance entry into cells. Compounds, prodrugs and salts thereof of this invention contain phenylboronate groups, in particular p -$B(OH)_2$-phenyl groups, benzoxaborole groups or borono-pyridyl groups or analogous groups in which the boronate group is protected. Methods for treating AIDS and ARC as well as providing a method for treating or preventing HIV infection.

14 Claims, 14 Drawing Sheets

(56) References Cited

OTHER PUBLICATIONS

Philipp et al. (1971) "Inhibition of Serine Proteases by Arylboronic Acids," Proc. Natl. Acad. Sci. USA. 68(2):478-480.
Plourde et al. (1990) "Synthesis of a Potentially Insulin-Mimetic Phosphodissaccharide," Tetrahedron Lett. 31(19):2693-2696.
Richardson et al. (2006) "Bortezomib: proteasome inhibition as an effective anticancer therapy," Annu. Rev Med. 57:33-47.
Smoum et al. (Apr. 20, 2012) "Boron Containing Compounds as Protease Inhibitors," Chemcial Reviews. 112(7):4156-4220.
Sui et al. (1993) "Inhibition of the HIV-1 and HIV-2 proteases by curcumin and curcumin boron complexes," Biorganic Med. Chem. 1(6):415-422.
Surleraux et al. (2005) "Discovery and Selection of TMC114, a Next Generation HIV-1 Protease Inhibitor," J. Med. Chem. 48:1813-1822.
Tie et al. (2004) "High resolution crystal structures of HIV-1 protease with a potent non-peptide inhibitor (UIC-94017) active against multi-drug-resistant clinical strains," J. Mol. Biol. 338:341-352.
Trippier et al. (2010) "Boronic acids in medicinal chemistry: anticancer, antibacterial and antiviral applications," Med Chem Commun. 1:183-198.
Yang et al. (2003) "Boronic acid compounds as potential pharmaceutical agents," Med Res Rev. 23:346-368.
Yang et al. (2005) "Biological and medicinal applications of boronic acids," In; Boronic acids: preparation, applications, in organic synthesis and medicine. Ed.: Hall. Wiley-VCH. Weinheim, Germany. pp. 481-512.
Yoshimura et al. (2002) "A potent human immunodeficiency virus type 1 protease inhibitor, UIC-94003 (TMC-126), and selection of a novel (A28S) mutation in the protease active site," J. Virol. 76:1349-1358.

A31        A32        A33

A34        A35        A36

A37        A38

A39    A40    A41    A42

Exemplary $R_{21}$ and $R^7$ 6,2Groups

PO3-spermine, PO3(spermine)2, or PO3(meglamine)2.

BORONIC ACID INHIBITORS OF HIV PROTEASE

CROSS-REFERENCE TO RELATED APPLICATIONS

This application claims the benefit of U.S. provisional application 62/072,367, filed Oct. 29, 2014 which is incorporated by reference herein in its entirety.

STATEMENT REGARDING GOVERNMENT FUNDING

This invention was made with government support under GM044783 awarded by the National Institutes of Health. The government has certain rights in the invention.

BACKGROUND OF THE INVENTION

Acquired immunodeficiency syndrome (AIDS), characterized by the destruction of the immune system, particularly of CD4 T-cells and susceptibility to opportunistic infections, and its precursor AIDS-related complex ("ARC"), are the result of infection by the HIV (human immunodeficiency) retrovirus. HIV strains include HIV type 1 (HIV-1) and HIV type 2 (HIV type 2). Retrovirus replication involves post-translation processing of precursor polypeptides by a virally encoded protease to produce mature viral proteins, viral assembly and the generation of infective virus. Inactivation of the viral protease (HIV protease) can result in the production of non-infectious virus. Inhibition of HIV protease provides a method for treatment of AIDS and ARC as well as providing a method for treating or preventing HIV infection.

Several HIV protease inhibitors are presently approved for clinical use in the treatment of AIDS and HIV infection, including indinavir (see U.S. Pat. No. 5,413,999), saquinavir (U.S. Pat. No. 5,196,438), ritonavir (U.S. Pat. No. 5,484,801), nelfinnavir (U.S. Pat. No. 5,484,926), lopinavir (U.S. Pat. No. 5,914,332), atazanavir (U.S. Pat. No. 5,849,911), amprenavir (U.S. Pat. No. 5,585,397), darunavir (U.S. Pat. No. 6,248,775) and tipranavir (U.S. Pat. No. 5,852,195). Tipranavir is a non-peptide protease inhibitor, the other listed protease inhibitor are peptide-derived protease inhibitors. Protease inhibitors are currently administered in combination with at least one and typically at least two other HIV antiviral agents, for example, nucleoside reverse transcriptase inhibitors such as zidovudine (AZT) and lamivudine (3TC) and/or non-nucleoside reverse transcriptase inhibitors, such as efavirenz and nevirapine. Combinations of the HIV protease inhibitors may be administered together, such as the combination of lopinavir and ritonavir. Ritonavir can be administered with other HIV protease inhibitors as a booster. Fosamprenavir (fosamprenavir calcium), is a prodrug of the HIV protease inhibitor and antiretroviral drug amprenavir. Each of the above-listed U.S. patents is incorporated by reference herein in its entirety, for description of methods of treatment and prevention of AIDs and HIV infection employing HIV protease inhibitors, dosage forms for such treatment, drug combinations with HIV protease inhibitors for such treatment, and administration of HIV protease inhibitors alone or in combinations with other antiretroviral drugs.

Of the listed approved HIV protease inhibitors amprenavir, fosamprenavir, darunavir and tipranavir contain sulfonamide structures. Additional HIV protease inhibitors include β-amino acid hydroxyethylamino sulfonamides, α-amino and β-amino acid hydroxyethylamino sulfonamides, lysine sulfonamides, among others. The present invention relates to new sulfonamide derivatives which exhibit HIV protease inhibition, antiretroviral activity and which are useful for the treatment of AIDS and HIV infection.

The following patent documents provide description of HIV protease inhibitors having sulfonamide groups: U.S. Pat. Nos. 5,585,397; 5,585,397; 5,744,481; 5,786,483; 5,843,946; 5,852,195; 5,852,195; 5,856,353; 5,968,942; 6,060,476; 6,169,181; 6,248,775; 6,248,775; 6,372,778; 6,417,387; 6,436,989; 6,472,407; 6,500,832; 6,646,010; 6,924,286; 7,608,632; 7,981,929; or U.S. published application 20100093811. Each of these patents or published applications describe structures of HIV protease inhibitors and prodrugs thereof which contain at least on sulfonamide group (—NR—$SO_2$—Ar/Het) where the aryl of heteroaryl group can be replaced generally with a boronated aryl group, a boronated heteroaryl group, an aryl group having a protected boronate group, or a heteroaryl group having a protected boronate group. More specifically, the aryl or heteroaryl groups of such HIV protease inhibitor sulfonamides can be replaced with a phenylboronate group, a benzoxaborole group, a borono-pyridyl group or derivative groups thereof where the boronate is protected as described in the present invention. Each of these patents is incorporated by reference herein in its entirety such description of the structures of HIV protease inhibitors and prodrugs thereof and of methods of preparation of such compounds and use of such compounds.

The use of HIV protease inhibitors has been impeded by difficulties with formulation (e.g., poor aqueous solubility), extensive metabolism, adverse effects in some patients, and the development of resistance to protease inhibitors. There is in general a need for new HIV proteases with improved properties for formulation, increased in vivo half-life and to overcome resistance. Additionally, there is a need in the art for HIV protease inhibitors exhibiting enhanced levels of inhibition which will provide for lower effective dosage amounts.

SUMMARY OF THE INVENTION

The invention relates to protease inhibitors, particularly aspartyl protease inhibitors, and more particularly to those which inhibit HIV protease. The invention provides compounds and certain prodrugs thereof and salts thereof which function as aspartyl protease inhibitors and HIV protease inhibitors.

The compounds, prodrugs and salts thereof of this invention contain phenylboronate groups, in particular p-B(OH)$_2$-phenyl groups, benzoxaborole groups or borono-pyridyl groups or analogous groups in which the boronate group is protected. More specifically, the phenyl boronate, benzoxaborole groups or borono-pyridyl groups or analogous groups in which the boronate group is protected replace certain aryl or heteroaryl groups of art-known sulfonamide HIV protease inhibitors and the resulting phenyl boronates, benzoxaboroles, or borono-pyridyl groups exhibit enhanced inhibition of HIV protease.

HIV protease inhibitors which are known in the art can be described by the formula:

G-NR—$SO_2$—Ar/Het where G, and R are various organic groups of known protease inhibitor, particularly known HIV inhibitors, which will be described in more detail below in the detailed description and which are exemplified herein. Various structures for the G group are found in formulas I, Ia, II, IIA, III, IIIA, IV, IVA, V, VI, VII, Viii, X, XI, XXI, XXII, XXVI, XXVII, XXXI, XXXIII, XLI, XLIII, XXXVI, XXXVIII, L, LII, LV, LVII, LVIV, LVV, MM, M, MI, or MVI. In specific embodiments, R is $C_1$-$C_4$ alkyl or $C_1$-$C_4$ alkyl substituted with a $C_3$-$C_7$ cycloalkyl group, Ar is an aryl group (e.g., optionally substituted phenyl) and Het is a heteroaryl group (e.g., optionally substituted pyridyl). Replacement of Ar or Het of such HIV inhibitors with a boronated aryl or boronated heteroaryl group results in significant enhancement of inhibition of HIV protease. In a specific embodiment, replacement of Ar or Het with phenyl boronate, benzoxaborole, or borono-pyridyl group results in significant enhancement of inhibition of HIV protease. In a specific embodiment, the boronate group of the boronated aryl or boronated heteroaryl is itself protected with a boronate protecting group and more particularly with a protecting group that is enzymatically removed in vivo. In a specific embodiment, the boronate protecting group is removed by an esterase found in mammalian cells and more particularly in human cells. In such an embodiment, the boronate protecting group is removed in vivo after administration. Protease inhibitors in which the aryl or heteroaryl group of the sulfonamide protease inhibitor are replaced with a boronated aryl or hereteroaryl group, respectively, and in which the boronate group therein is protected can function as prodrug where the protecting group is removed in vivo after administration.

The invention is directed to certain phenyl boronate compounds, certain prodrugs thereof and salts thereof. In specific embodiments, the compounds, prodrugs and salts are useful for inhibition of aspartyl proteases, particularly HIV aspartyl proteases. The phenylboronate compounds, prodrugs and salts thereof of the invention are useful for the treatment and prevention of HIV invention and AIDS.

The invention is directed to certain benzoxaborole compounds, certain prodrugs thereof and salts thereof. In specific embodiments, the compounds, prodrugs and salts of the invention are useful for inhibition of aspartyl proteases, particularly HIV aspartyl proteases. The benzoxaborole compounds, prodrugs and salts thereof of the invention are useful for the treatment and prevention of HIV invention and AIDS.

The invention is directed to certain borono-pyridine compounds, certain prodrugs thereof and salts thereof. In specific embodiments, the compounds, prodrugs and salts of the invention are useful for inhibition of aspartyl proteases, particularly HIV aspartyl proteases. The borono-pyridine compounds, prodrugs and salts thereof of the invention are useful for the treatment and prevention of HIV invention and AIDS.

The invention is directed to pharmaceutically acceptable compositions which comprise a therapeutically effective amount of one or more of the phenyl boronates, benzoxaboroles, borono-pyridines or boronate protected derivatives thereof of this invention and a pharmaceutically acceptable carrier. The invention is directed to pharmaceutically acceptable compositions which comprise a therapeutically effective amount of one or more of the phenyl boronates, benzoxaboroles, borono-pyridines or boronate protected derivatives thereof of this invention in a pharmaceutically acceptable dosage form.

The invention is further directed to methods of treating mammals, particularly humans, with the compounds, prodrugs, and salts thereof and pharmaceutical compositions thereof of the invention.

The invention is additionally directed to a method for making an improved protease inhibitor wherein the protease inhibitor is of the formula:

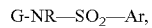

G-NR—SO$_2$—Ar, containing a aryl or heteroaryl group, which comprises the step of replacing the aryl or heteroaryl group of the protease inhibitor with a boronated aryl or boronated heteroaryl group, wherein the boronate group in the boronated aryl or boronated heteroaryl group is optionally protected with boronate protecting group. In specific embodiments, the protease inhibitor is an aspartyl protease inhibitor. In more particular embodiments, the protease inhibitor is an HIV protease inhibitor. In specific embodiments, the aryl is replaced with phenyl boronate or benzoxaborole. In specific embodiments, the heteroaryl group is replaced with a borono-pyridine. In specific embodiments, the boronated aryl or boronated heteroaryl group contains a protected boronate group. In specific embodiments, the boronate protecting group is removed or is removable by an enzymatic reaction in vivo, for example in mammalian cell or more particularly in human cells. In more specific embodiments, the boronate protecting group is removable by an esterase found in mammalian cells and more particularly in human cells. The term "replacement" is used herein with respect to the formulas of the group that is to be replaced and that of the boronated aryl or heteroaryl group that will be in the resulting compound. Replacement is achieved by chemical conversion of the existing group to be replaced or more typically by synthesis of the compound having the boronated aryl or heteroaryl group. This synthesis can be accomplished in a variety of ways, for example, by choice of appropriate boronated starting materials or by boronation at an intermediate stage in the synthesis.

Other aspects and embodiments of the invention will be apparent to one of ordinary skill in the art on review of the detailed description, and examples.

DETAILED DESCRIPTION OF THE INVENTION

Figure 1A:
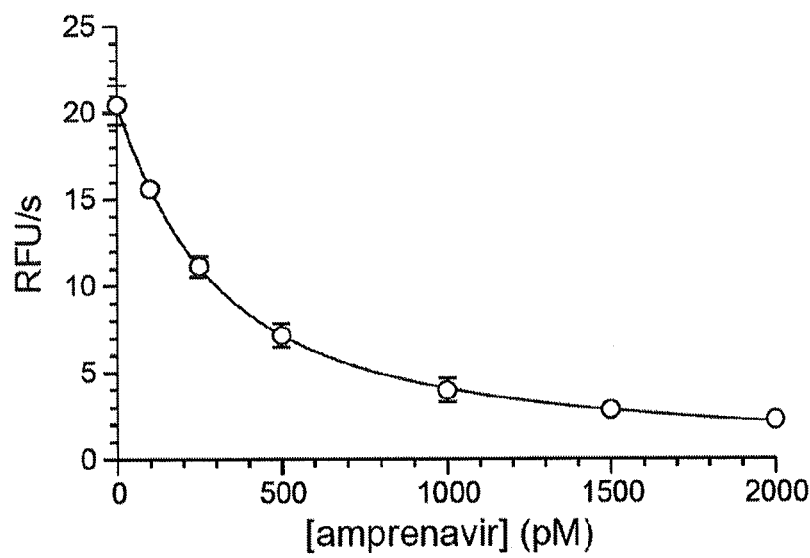
FIGS. 1A-B are graphs showing the inhibition of the enzymatic activity of HIV-1 protease by (A) amprenavir and (B) darunavir, and the boronated cognates B-amprenavir 6 and B-darunavir 9.

The present invention relates to protease inhibitors, particularly HIV protease inhibitors, having an aryl or heteroaryl sulfonamide group, wherein the aryl or heteroaryl group is a boronated aryl or boronated heteroaryl group, e.g., a phenyl boronate group, a benzoxaborole group or a borono pyridyl group. The inventors have found that such substitution on known sulfonamide HIV protease inhibitors does not detrimentally affect activity, but rather results in enhanced inhibition. In addition, the boronate group of the boronated aryl or boronated heteroaryl group is optionally protected with a boronate protecting group that is removable in vivo to provide an exemplary HIV protease inhibitor prodrug.

The inventors have determined that boronation on an aryl or heteroaryl group of a sulfonamide protease inhibitor unexpectedly enhances that activity. Without wishing to be bound by any particular theory the inventors currently believe that the presence of phenyl boronate or boronated pyridyl groups, with a —B(OH)₂ group, or a benzoxaborole group, with a:

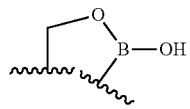

moiety, in the sulfonamide protease inhibitors of this invention as described herein enhances binding of the inhibitor to the protease. This enhanced activity has been specifically demonstrated in sulfonamide HIV protease inhibitors.

The term phenyl boronate group (which may also be called a phenyl boronic acid group or a borono-phenyl group) refers to a phenyl group carrying a —B(OH)₂ group. The phenyl boronate group is formally a monovalent radical where a ring hydrogen is formally removed to form the radical. The phenyl boronate groups of this invention are not further substituted with non-hydrogen groups on the ring. When the group is not further substituted with non-hydrogen groups, there are three isomers of the group dependent upon the ring carbon through which the group is bonded into the compounds therein. Numbering the carbons of the phenyl ring where the carbon carrying B is carbon 1, the isomers can be named 2-phenyl boronate, and 3-phenyl boronate. The phenyl boronate group generically has the formula:

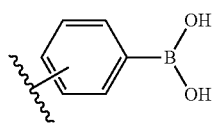

where the position of the boronate group with respect to the carbon bonded to the rest of the inhibitor can vary. Compounds of the invention can be any of the positional isomers of the phenyl boronate group. The preferred phenyl boronate group is the 3-phenyl boronate group in which the —B(OH)₂ group is para to the site of the group's bonding, i.e., para to the carbon through which the group is bonded:

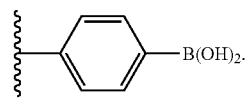 [SMILES: *c1ccc(B(O)O)cc1]

The term benzoxaborole group refers to a phenyl boronate group that is substituted with a —CH₂—CH₂—OH group on the ring carbon next to (ortho to) the —B(OH)₂ group, wherein a five member ring fused to the phenyl ring is formed with loss of water. The benzoxaborole group is a monovalent radical formally formed by removal of a hydrogen from the phenyl ring. The benzoxaborole group generically has the formula:

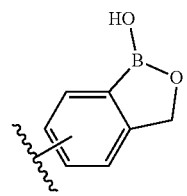

where the position of the carbon bonded to boron with respect to the carbon bonded to the rest of the inhibitor can vary. The benzoxaborole groups of this invention are not further substituted with non-hydrogen groups on the ring. When the group is not further substituted with non-hydrogen groups, there are four isomers of the group dependent upon the ring carbon through which the group is bonded into the compounds herein. Numbering the carbons of the phenyl ring where the carbon carrying B is carbon 1, the isomers can be named 2-benzoxaborole (2-benzoxaborolyl), 3-benzoxaborole (3-benzoxaborolyl), 4-benzoxaborole (4-benzoxaborolyll) and -5-benzoxaborole (5-benzoxaborolyl). Compounds of the invention can have any one of isomers of the benzoxaborole group. The preferred benzoxaborole groups are the 3-benzoxaborole (A) and the 4-benzoxaborole (B) groups

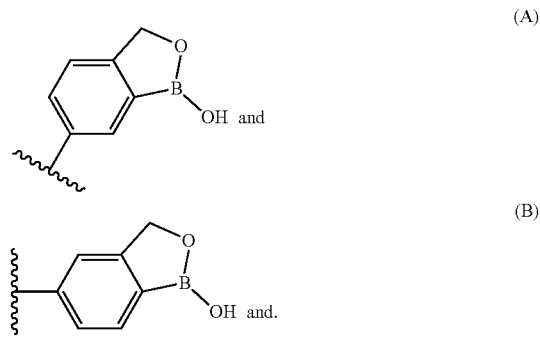 [SMILES: *c1ccc2c(c1)B(O)OC2 ; *c1ccc2c(c1)COB2O]

The more preferred benzoxaborole group is 4-benzoxaborole, structure B.

Nitrogen-containing heteroaryl groups such as pyridyl groups can be boronated. Boronated pyridyl groups have the generic formula:

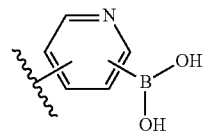

where the relative positions of the carbon bonded to the boronate, the carbon bonded to the rest of the inhibitor and the ring nitrogen can vary. Boronated pyridyl groups include several isomers which will be apparent to one of ordinary skill in the art. In the present invention, preferred boronated heteroaryl groups are those where a —B(OH)$_2$ group is in the para-orientation from the site of its attachment in the protease inhibitor. For boronated pyridyl groups a preferred isomer is: 5-borono-pyrid-2-yl:

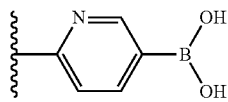

An alternative boronated pyridyl group that can be used in the compounds of the invention is the 6-borono-pyrid-2-yl:

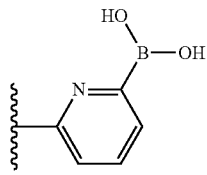 [SMILES: *c1cccc(B(O)O)n1]

Example 7 provides an exemplary synthesis of the boronated analogue of tipranavir, which contains the 5-borono-pyrid-2-yl group.

Boronate groups in the boronated aryl or boronated heteroaryl groups are optionally protected with a boronate protecting group. A number of such boronate protecting groups are known in the art. Of particular interest for the applications herein are those boronate protecting groups that can be removed enzymatically by one or more enzymes found in vivo in mammalian cells and particularly in human cells. A particularly useful boronate protecting reagent is N-methyliminodiacetic acid and derivatives thereof of formula:

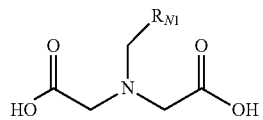

where $R_{N1}$ is hydrogen, alkyl (particularly C1-3 alkyl), cycloalkyl (particularly cyclohexyl), alkenyl (particularly C2-C4 alkenyl), aryl (particularly phenyl), heterocyclic groups (particularly heterocyclic groups having a 5- or 6-member ring and 1 or 2 heteroatoms in the ring selected independently from N, O or S), heteroaryl groups (particularly heteroaryl groups having a 5- or 6-member ring and 1 or 2 heteroatoms in the ring selected independently from N, O or S), or an alkyl group having 1-3 carbon atoms substituted with a cycloalkyl, aryl, heterocyclic, or heteroaryl group. In specific embodiments, $R_{N1}$ is hydrogen.

In an embodiment, protected boronated aryl and heteroaryl groups are selected from those of formulas:

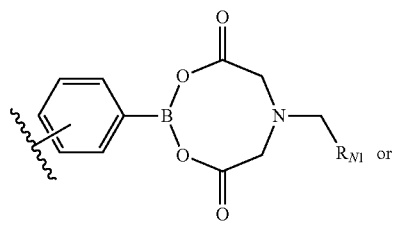

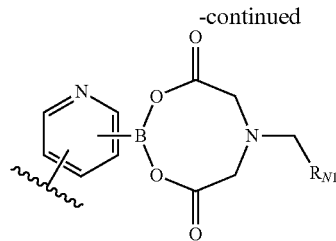

where the position of the protected boronate group with respect to the carbon bonded to the rest of the inhibitor and with respect to a the ring N (if present) can vary. The exemplified protected boronate group is an N-substituted iminodiacetate boronate ester often shown as formula:

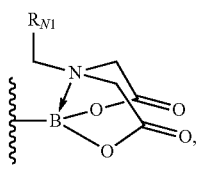

where $R_{N1}$ is as defined above and more specifically is hydrogen.

A more specific protected boronated aryl group is that of the formula:

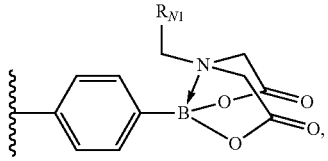

where $R_{N1}$ is as defined above and more specifically is hydrogen. Other positional isomers of phenyl boronate can also be protected with the N-substituted iminodiacetic acid.

More specific protected boronated heteroaryl groups are those of the formula:

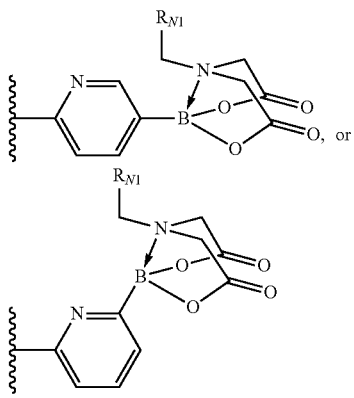

where $R_{N1}$ is as defined above and more specifically is hydrogen. Other positional isomers of borono-pyridyl can also be protected with the N-substituted iminodiacetic acid.

U.S. Pat. Nos. 5,585,397, 5,856,353, 6,372,778, and 7,608,632 relate to sulfonamide inhibitors of aspartyl protease which are useful as HIV protease inhibitors for the prevention and treatment of HIV infection and AIDS. Each of these patents is incorporated by reference herein in its entirety for descriptions of the compounds and pharmaceutically acceptable derivatives thereof, for methods of synthesis of these compounds and derivatives, for pharmaceutical compositions comprising the compounds and derivatives, for pharmaceutical dosage forms of the compounds and derivatives and for methods of treatment employing these compounds and derivatives and methods of administration of these compounds and derivatives to mammals and particularly to humans. Compounds of these patents include those of formula I:

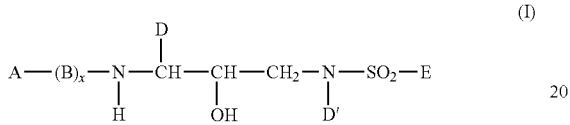
(I)

where variables are defined therein and the listed patents are incorporated by reference herein to provide variable definitions. More specifically, x is 0 or 1, B if present is —N(R$^2$)—C(R$^3$)$_2$—CO—, where R$^2$ is among others hydrogen, C1-C3 alkyl or C1-C3 alkyl substituted with an aryl group (e.g., a phenyl group). More specifically D and D' are among others independently selected from aryl, optionally substituted C1-C4 alkyl, C1-C4 alkyl substituted with aryl or C3-C6 cycloalkyl, C2-C4 alkenyl, C3-C6 cycloalkyl, C5-C6 cycloalkenyl, where variables are as defined in the listed patents. More specifically, A is among others hydrogen, A is selected among others from the group consisting of H; Het; and —CO-Het, and —CO—O-Het, where Het is selected among others from the group consisting of C3-C7 cycloalkyl; C5-C7 cycloalkenyl; C6-C10 aryl; and 5-7 membered saturated or unsaturated heterocyclic groups, containing one or more heteroatoms selected from N, N(R$^2$) O, S, SO or SO$_2$, wherein said heterocycle may optionally be benzofused. E as defined in the listed patents includes Het which is defined in these patents to include certain cycloalkyl, aryl and heterocyclic groups. The present invention provides compounds of the above formula as defined in the listed patent where E is BBB which is a phenylboronate group, a benzoxaborole group, a borono-pyridyl gorup or boronate protected derivatives thereof and in particular where BBB is selected from any one of:

BBB1
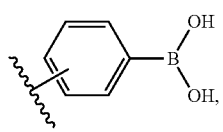

BBB2
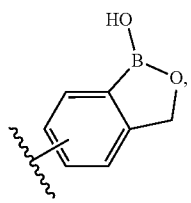

BBB3
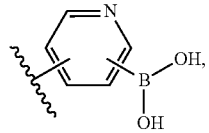

BBB4
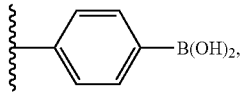

BBB5
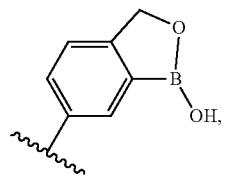

BBB6
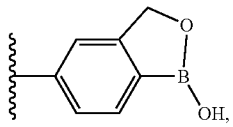

BBB7
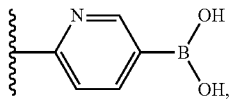

BBB8
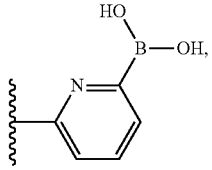

BBB9
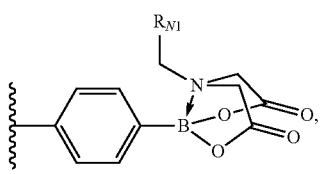

BBB10
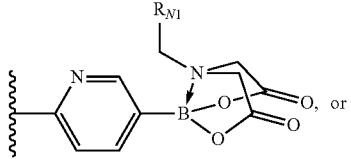

or

BBB11
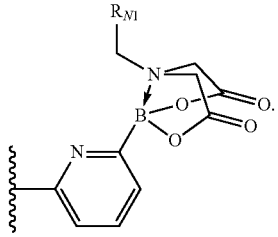

In a related embodiment, the invention provides compounds of the above formula as defined in the listed patent where E is:

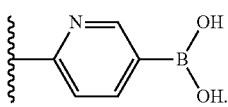

These patents further provide compounds of formulas II, III and IV, respectively:

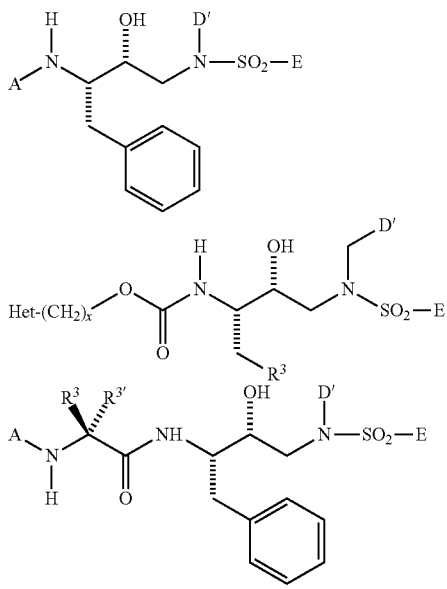

again where variables are as defined in the listed patents and more specifically where A, D' Het are as defined above, x is 1 or 0 and R³ and R³' is more specifically independently selected from the group consisting of among others, hydrogen, Het, C1-C6 alkyl, and C3-C6 cycloalkyl. The present invention provides compounds and pharmaceutically acceptable derivatives (as defined therein) of each of these formulas where E is BBB which is a phenylboronate group, a benzoxaborole group, a boron-pyridyl group or a protected boronate derivative thereof and in particular where BBB is:

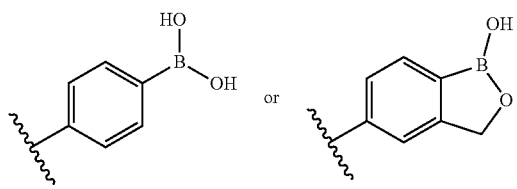 [SMILES: *c1ccc(B(O)O)cc1 ; *c1ccc2c(c1)COB2O]

In a related embodiment, the invention provides compounds of the above formulas as defined in the listed patent where E is:

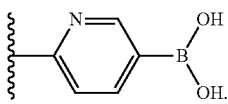

In a related embodiment, BBB is BBB1-BBB11 as defined above. In a more specific embodiment, BBB is BBB9-BBB11.

Compounds of formulas I, II, III and IV above where E is BBB can be prepared, from starting materials and reagents that are commercially available or readily prepared by known methods, or routine adaptations thereof, by one of ordinary skill in the art in view of methods described in U.S. Pat. Nos. 5,585,397, 5,856,353, 6,372,778, and 7,608,632, in view of methods for introducing phenyl boronates, benzoxaboroles or boron-substituted pyridyl groups as described herein and as are known in the art and in view of synthetic methods that are well known in the art.

Compound herein containing a boronate protected aryl or a boronate protected heteroaryl group can be prepared from starting materials and reagents that are commercially available or readily prepared by known methods, or routine adaptations thereof, by one of ordinary skill in the art, Compounds herein having a boronate group protected with an N-derivatized iminodiacetic acid (see formula above) can be prepared from starting materials and reagents that are commercially available or readily prepared by known methods, or routine adaptations thereof, by one of ordinary skill in the art, in view of descriptions herein and in U.S. Pat. Nos. 8,318,983, 8,557,980 and 8,722,916 as well as in references 14-16. Each of these patent and non-patent references are incorporated by reference herein in its entirety for descriptions of synthesis of compounds having a boronate group protected with an N-derivatized iminodiacetic acid.

U.S. Pat. Nos. 5,843,946, 5,744,481, 5,786,483, 6,060,476, 6,472,407, 6,500,832, relate to β-amino acid hydroxyethylamino sulfonamides, α-amino and β-amino acid hydroxyethylamino sulfonamides and pharmaceutically acceptable salts, prodrugs and esters thereof useful as retroviral protease inhibitors which are useful as HIV protease inhibitors for the prevention and treatment of HIV infection and AIDS. Each of these patents is incorporated by reference herein in its entirety for descriptions of the compounds and pharmaceutically acceptable salts, prodrugs and/or esters thereof, for methods of synthesis of these compounds and derivatives, for pharmaceutical compositions comprising the compounds and pharmaceutically acceptable salts, prodrugs and/or esters, for pharmaceutical dosage forms of the compounds and derivatives and for methods of treatment employing these compounds, salts, prodrugs and esters and methods of administration of these compounds salts, prodrugs and esters to mammals and particularly to humans. Compounds of these patents include those of formula IA:

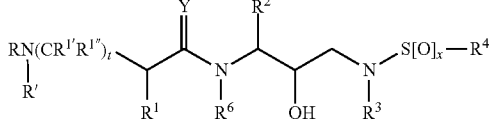

where variables are as defined in the U.S. Pat. Nos. 5,843,946, 5,744,481, and 5,786,483, which are each incorporated by reference herein for the definitions of such variables. Compounds of these patents include those in which x is 2 (e.g., sulfonamides) and where $R^4$ is, among others, aryl and heteroaryl. Compounds of this patent include those where Y is O or S, $R^6$ is hydrogen and $R^3$ is alkyl among others.

The present invention provides compounds and pharmaceutically acceptable derivatives (as defined therein) of each of these formulas where $R^4$ is BBB which is a phenylboronate group, a benzoxaborole group, a borono-pyridyl group or a protected boronate derivative thereof. In particular BBB is BBB1-BBB11. In particular BBB is:

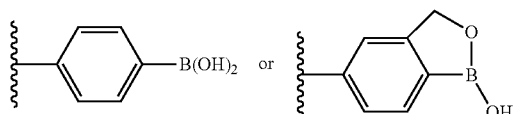

In a related embodiment, the invention provides compounds of the above formula as defined in the listed patent where BBB is:

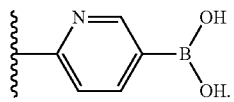

In a related embodiment, the invention provides compounds of the above formula as defined in the listed patent where BBB is BBB9-BBB11.

Among the compounds described in U.S. Pat. Nos. 5,843,946, 5,744,481, 5,786,483, 6,060,476, 6,472,407, 6,500,832 are those of formulas IIA-IVA:

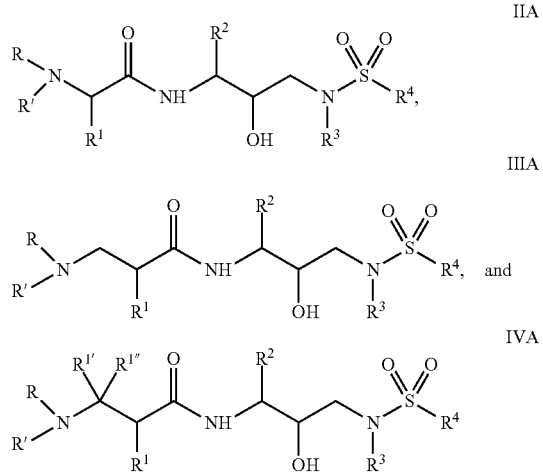

therein,
where variables are as defined in the listed U.S. patents and particularly in U.S. Pat. Nos. 5,843,946, 5,744,481, and 5,786,483, which are each incorporated by reference herein for the definitions of such variables. In these formulas, $R^4$ is among others aryl and heteroaryl groups, $R^3$ is among others alkyl groups. In these formulas:

R is selected from hydrogen, alkoxycarbonyl, aralkoxycarbonyl, alkylcarbonyl, cycloalkylcarbonyl, cycloalkylaminocarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, hetercaralkoxycarbonyl, heteroaryloxycarbonyl, heteroaroyl, alkyl, alkenyl, alkynyl, cycloalkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl, wherein the substituents are selected from alkyl, aryl, aralkyl, cycloalkyl, cycloalkylalkyl, heteroaryl, heteroaralkyl, heterocycloalkyl, and heterocycloalkyalkyl or where the aminocarbonyl and aminoalkanoyl radicals are disubstituted said substituents along with the nitrogen atom to which they are attached form a heterocycloalkyl or heteroaryl group; and R' represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals. wherein said substituents are selected from alkyl, aryl, aralkyl, cycloalkyl, cycloalkylalkyl, heteroaryl, heteroaralkyl, heterocycloalkyl, and heterocycloalkylalkyl groups or in the case of a disubstituted aminoalkyl moiety said substituents along with the nitrogen atom to which they are attached. form a heterocycloalkyl or a heteroaryl group or R and R' together with the nitrogen to which they are attached represent heterocycloalkyl and heteroaryl radicals;

$R^1$ and $R^{1'}$ are independently selected from hydrogen, —$CH_2SO_2NH_2$, —$CH_2CO_2CH_3$, —$CO_2CH_3$, —$CONH_2$, —$CH_2CONHCH_3$, —$C(CH_3)_2(SH)$, —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl and cycloalkyl groups, and amino acid side chains or $R^1$ and $R^{1'}$ together with the carbon to which they are attached present a cycloalkyl group; and $R^2$ is selected from alkyl, aryl, cycloalkyl, cycloalkylalkyl, and aralkyl groups (alkyl substituted with an aryl group, such as benzyl).

The present invention provides compounds and pharmaceutically acceptable derivatives (as defined therein) of each of these formulas where $R^4$ is BBB which is a phenylboronate group, a benzoxaborole group, a borono-pyridyl group or a protected boronate derivative thereof. In particular BBB is BBB1-BBB11. In particular BBB is:

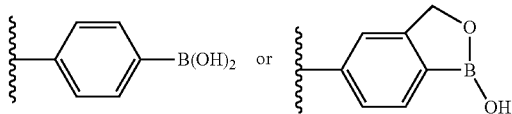

In related embodiments, BBB is:

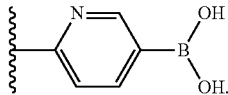 [SMILES: *c1ccc(B(O)O)cn1]

In related embodiments, BBB is BBB9-BBB11.

Compounds of formulas I, II, III and IV, where $R^4$ is BBB or a boronated pyridyl group can be prepared, from starting materials and reagents that are commercially available or readily prepared by known methods, or routine adaptations thereof, by one of ordinary skill in the art in view of methods described in U.S. Pat. Nos. 5,843,946, 5,744,481, 5,786,483, 6,060,476, 6,472,407, 6,500,832 in view of methods for introducing phenyl boronates, benzoxaboroles and boronated pyridyl groups as described herein and as are known in the art and in view of synthetic methods that are well known in the art. Compounds herein having a boronate group protected with an N-derivatized iminodiacetic acid can be prepared from starting materials and reagents that are commercially available or readily prepared by known methods, or routine adaptations thereof, by one of ordinary skill in the art, in view of descriptions herein and in U.S. Pat. Nos. 8,318,983, 8,557,980 and 8,722,916 as well as in references 14-16.

U.S. Pat. Nos. 5,968,942, 6,248,775, 6,646,010, 6,417,387 and 6,924,286 relate to α-amino and β-amino acid hydroxyethylamino sulfonamides and pharmaceutically acceptable salts, prodrugs and esters thereof useful as retroviral protease inhibitors which are useful as HIV protease inhibitors for the prevention and treatment of HIV infection and AIDS. Each of these patents is incorporated by reference herein in its entirety for descriptions of the compounds and pharmaceutically acceptable salts, prodrugs and/or esters thereof, for methods of synthesis of these compounds and derivatives, for pharmaceutical compositions comprising the compounds and pharmaceutically acceptable salts, prodrugs and/or esters, for pharmaceutical dosage forms of the compounds and derivatives and for methods of treatment employing these compounds, salts, prodrugs and esters and methods of administration of these compounds salts, prodrugs and esters to mammals and particularly to humans. Compounds of these patents include those of the following formula therein, herein designated formula V:

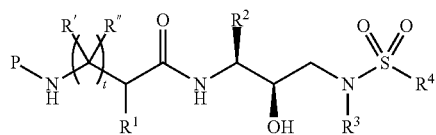

where variables are as defined in U.S. Pat. Nos. 5,968,942, 6,248,775, 6,646,010, 6,417,387 and 6,924,286, which are each incorporated by reference herein for the definitions of such variable. Compounds of these patents include those in where $R^4$ is, among others, aryl and heteroaryl. Specific variables in this structure are as defined above.

The present invention provides compounds and pharmaceutically acceptable derivatives (as defined therein) of this formula V, with variables as defined in the listed patents, where $R^4$ is BBB which is a phenylboronate group, a benzoxaborole group, a borono-pyridyl group or a protected boronate derivative thereof. In particular BBB is BBB1-BBB11. In particular, BBB is

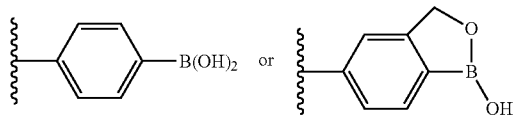

In a related embodiment BBB is:

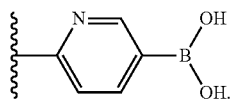

In another embodiment, BBB is BBB9-BBB11.

Compounds of the above formula as defined in U.S. Pat. Nos. 5,968,942, 6,248,775, 6,646,010, 6,417,387 and 6,924,286, and named formula V herein, except that $R^4$ is BBB can be prepared, from starting materials and reagents that are commercially available or readily prepared by known methods, or routine adaptations thereof, by one of ordinary skill in the art, in view of methods described in U.S. Pat. Nos. 5,968,942, 6,248,775, 6,646,010, 6,417,387 and 6,924,286, in view of methods for introducing phenyl boronates, benzoxaboroles, and boron-pyridyl groups as described herein and as are known in the art and in view of synthetic methods that are well known in the art.

U.S. Pat. Nos. 5,968,942, 6,248,775, 6,646,010, 6,417,387 and 6,924,286, also disclose compounds, salts, prodrugs and esters of the following formula VI

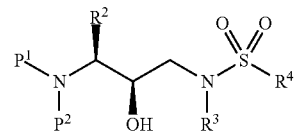

where variables are as defined in the listed patents and particularly in the claims of U.S. Pat. No. 6,248,775 which is incorporated by reference herein for these variable definitions and again where $R^4$ can, among others, be an aryl or heteroaryl group. In this formula:

each of $P^1$ and $P^2$ are independently selected from hydrogen, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxycarbonyl, heteroaroyl, alkyl, alkenyl, cycloalkyl, aryl, aralkyl, aryloxyalkyl, heteroaryloxyalkyl, hydroxyalkyl, aminocarbonyl, aminoalkanoyl, or mono- or disubstituted aminocarbonyl or mono- or disubstituted aminoalkanoyl radical, wherein the substituents are selected from the group consisting of alkyl, aryl, aralkyl, cycloalkyl, cycloalkylalkyl, heteroaryl, heteroaralkyl, heterocycloalkyl and heterocycloalkyalkyl radicals; or where said aminoalkanoyl radical is disubstituted, said substituents along with the nitrogen atom to which they are attached form a heterocycloalkyl or heteroaryl radical;

$R^2$ is an alkyl, aryl, cycloalkyl, cycloalkylalkyl or aralkyl radical, which radicals are optionally substituted with a group selected from alkyl and halogen radicals, nitro, cyano, $CF_3$, $-OR^9$, $-SR^9$, wherein $R^9$ is a hydrogen or alkyl radical;

$R^3$ is a hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl or mono- or disubstituted aminoalkyl radical, wherein said substituents are selected from the group consisting of alkyl, aryl, aralkyl, cycloalkyl, cycloalkylalkyl, heteroaryl, heteroaralkyl, heterocycloalkyl and heterocycloalkylalkyl radicals; or where the aminoalkyl radical is disubstituted, said substituents along with the nitrogen atom to which they are attached, form a heterocycloalkyl or a heteroaryl radical; and $R^4$ is among others an aryl or heteroaryl group.

The present invention provides compounds and pharmaceutically acceptable derivatives (as defined therein) of this formula VI, with variables as defined in the listed patents, where $R^4$ is BBB which is a phenylboronate group, a benzoxaborole group, a borono-pyridyl group or a protected boronate derivative thereof. In particular BBB is BBB1-BBB11. In particular, BBB is

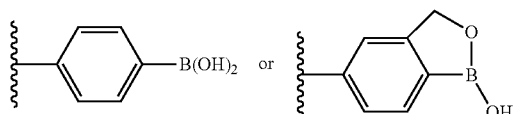

In a related embodiment, BBB is:

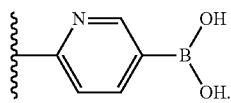

In another embodiment, BBB is BBB9-BBB11.

In specific embodiments the present invention provides compounds, salts, prodrugs and esters of formula VII

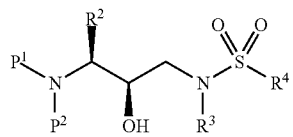

VII where $P^1$ is a heterocyclooxycarbonyl as defined in U.S. Pat. No. 6,248,775, $P^2$ is hydrogen and $R^4$ is where $R^4$ is BBB which is a phenylboronate group, a benzoxaborole group, a borono-pyridyl group or a protected boronate derivative thereof. In particular BBB is BBB1-BBB11. In particular, BBB is

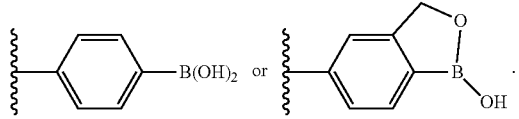

In related embodiments, BBB is:

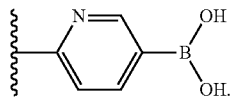 [SMILES: *c1ccc(B(O)O)cn1]

In other embodiments, BBB is BBB9-BBB11.

Figure 1B:
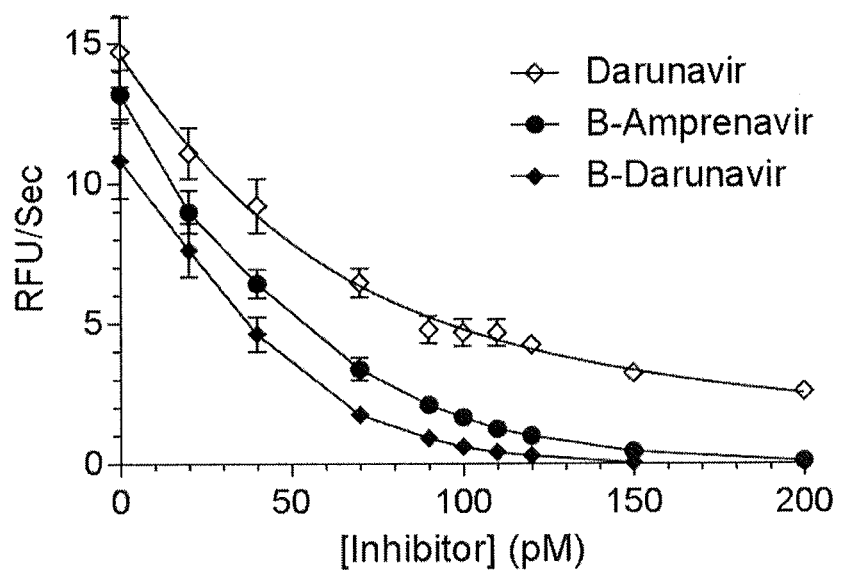
Figure 2:
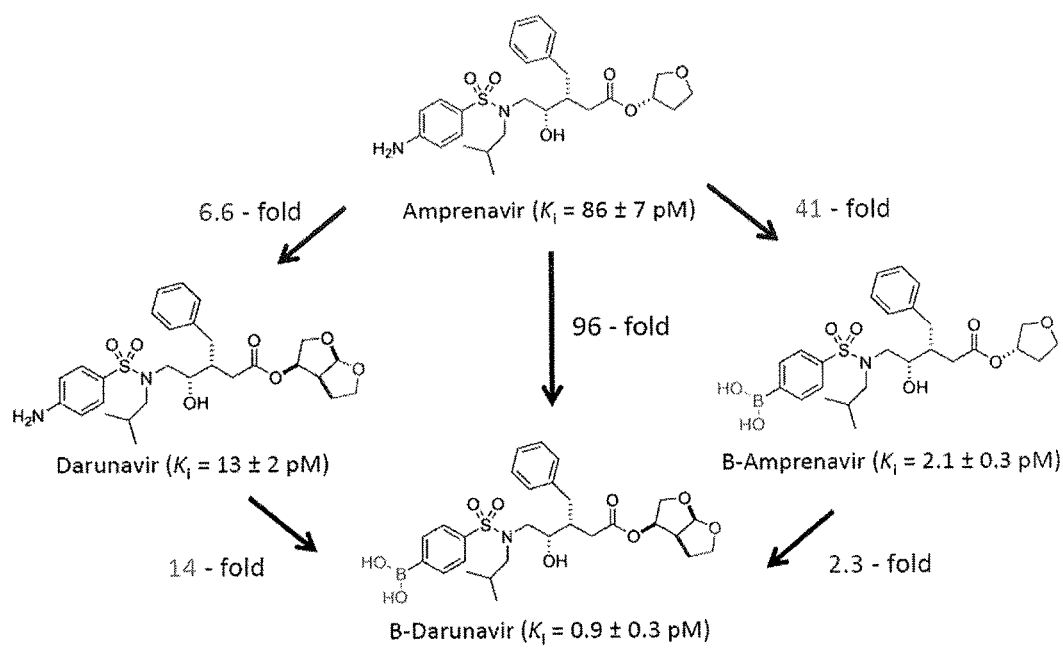
FIG. 2 is a scheme comparing the relative inhibition of the enzymatic activity of HIV-1 protease by amprenavir, darunavir, and the boronated cognates B-amprenavir 6 and B-darunavir 9. The boronated-cognates exhibit more than a 10-fold enhancement in inhibition compared to their non-boronated cognate compounds.
Figure 5A:
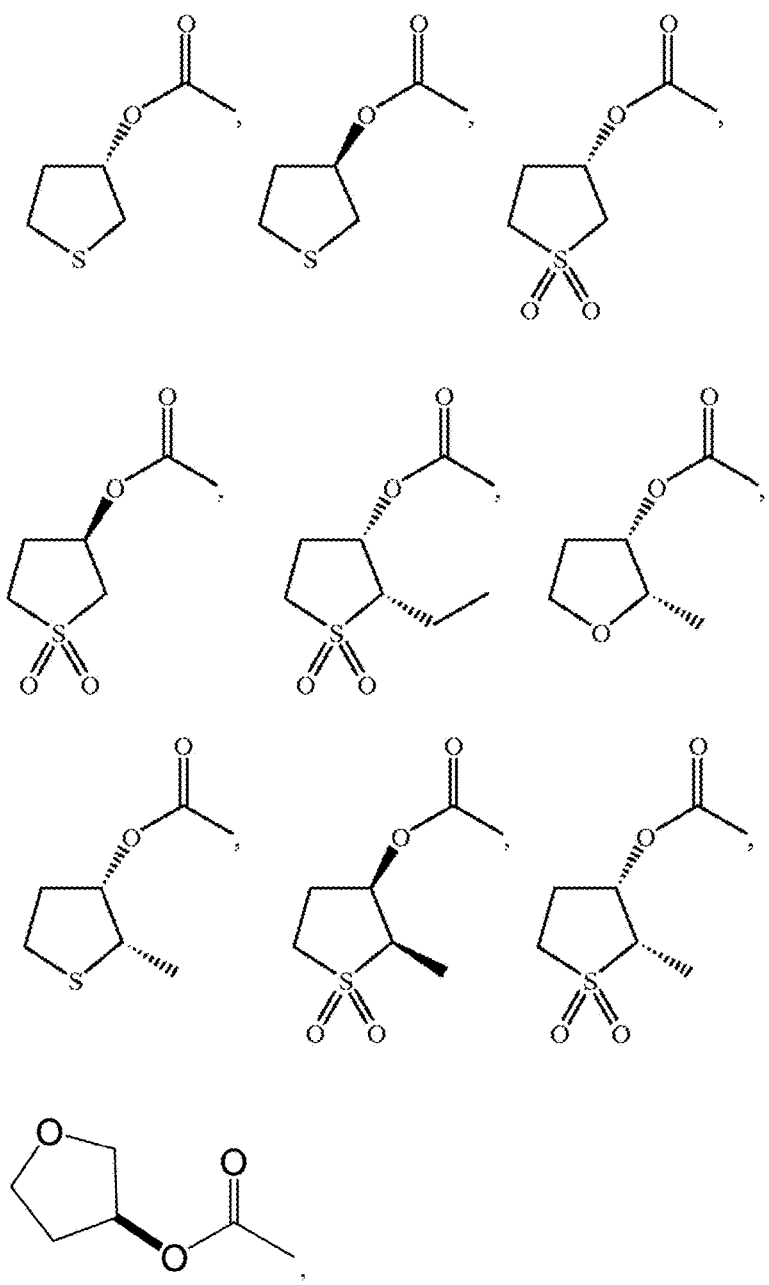
FIGS. 5A-5B list representative P1 groups for compounds of the invention.
Figure 5B:
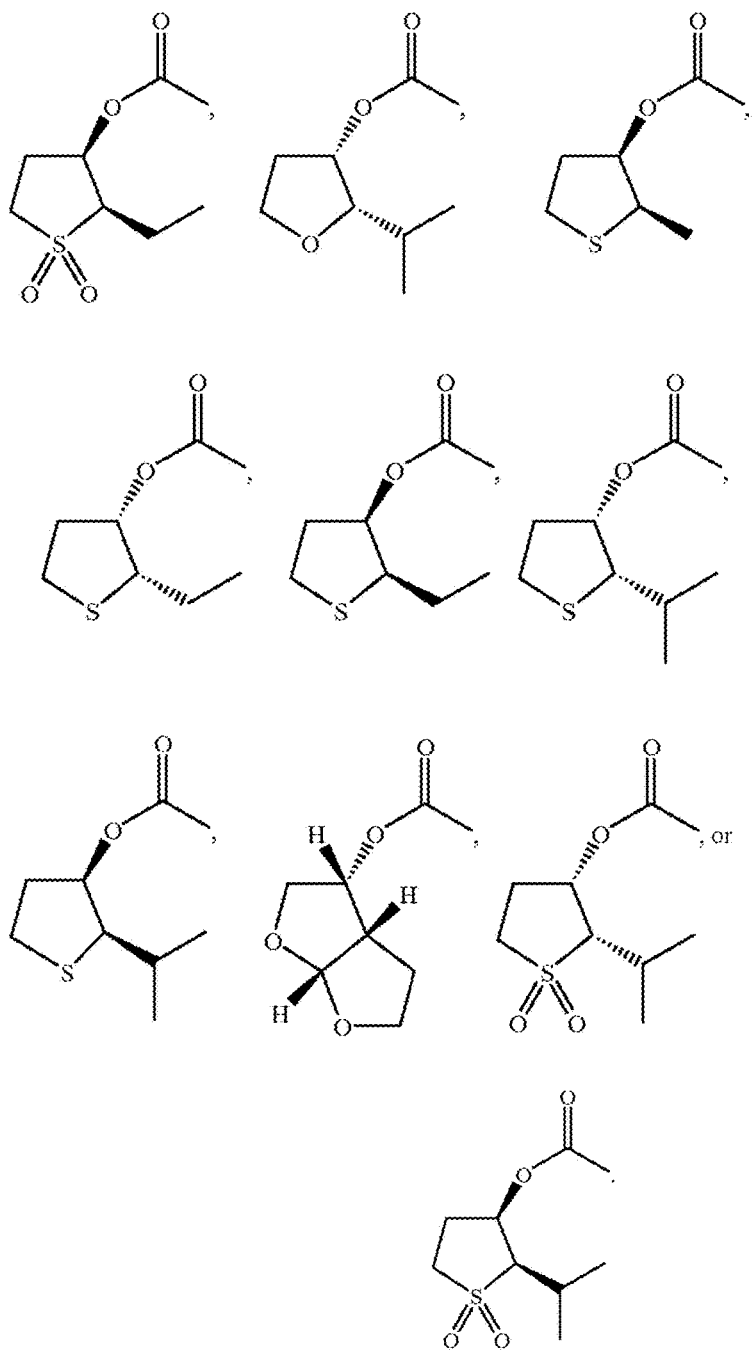
Figure 6A:
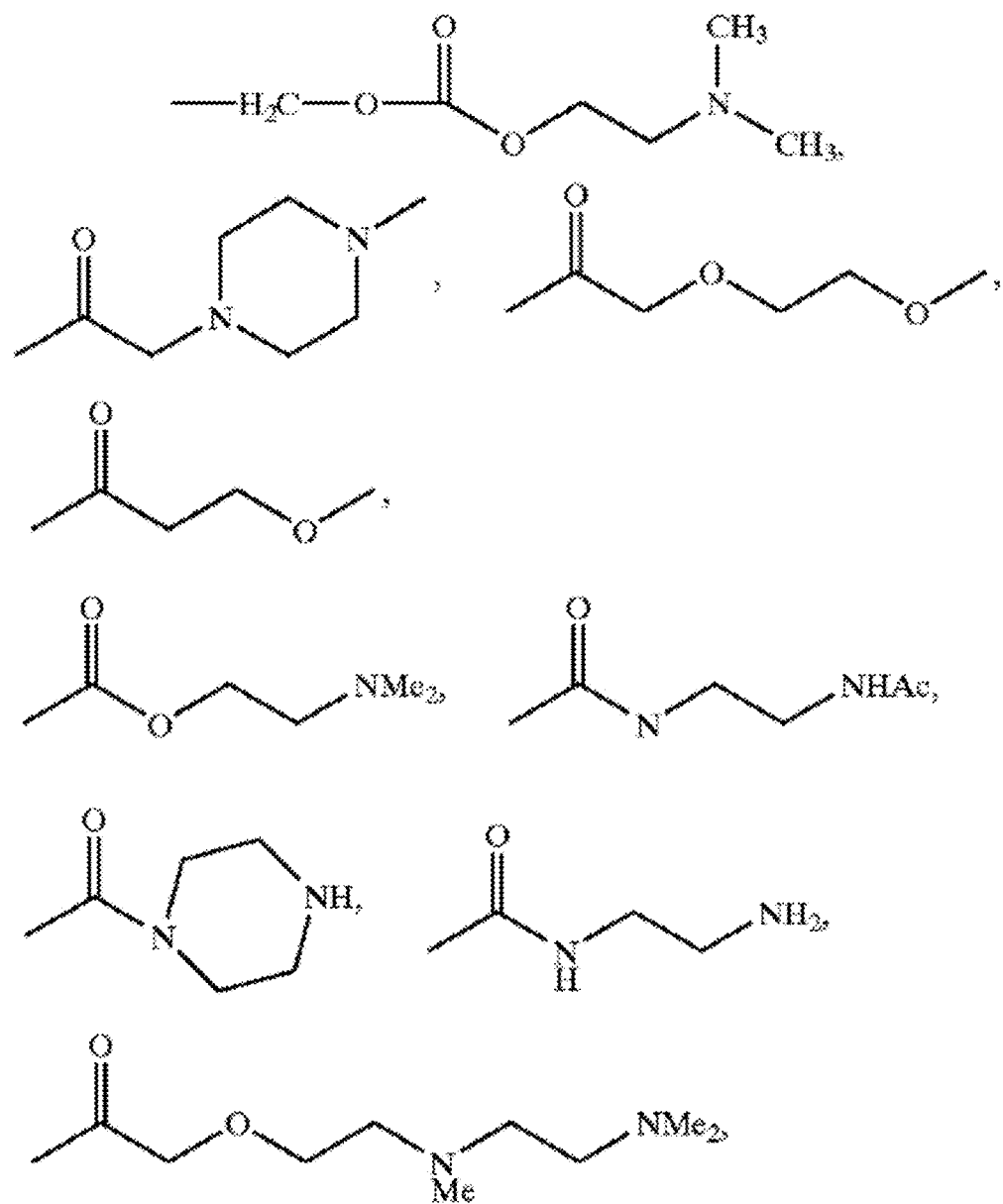
FIGS. 6A-6C list representative R21 and R7 groups for compounds of the invention.
Figure 6B:
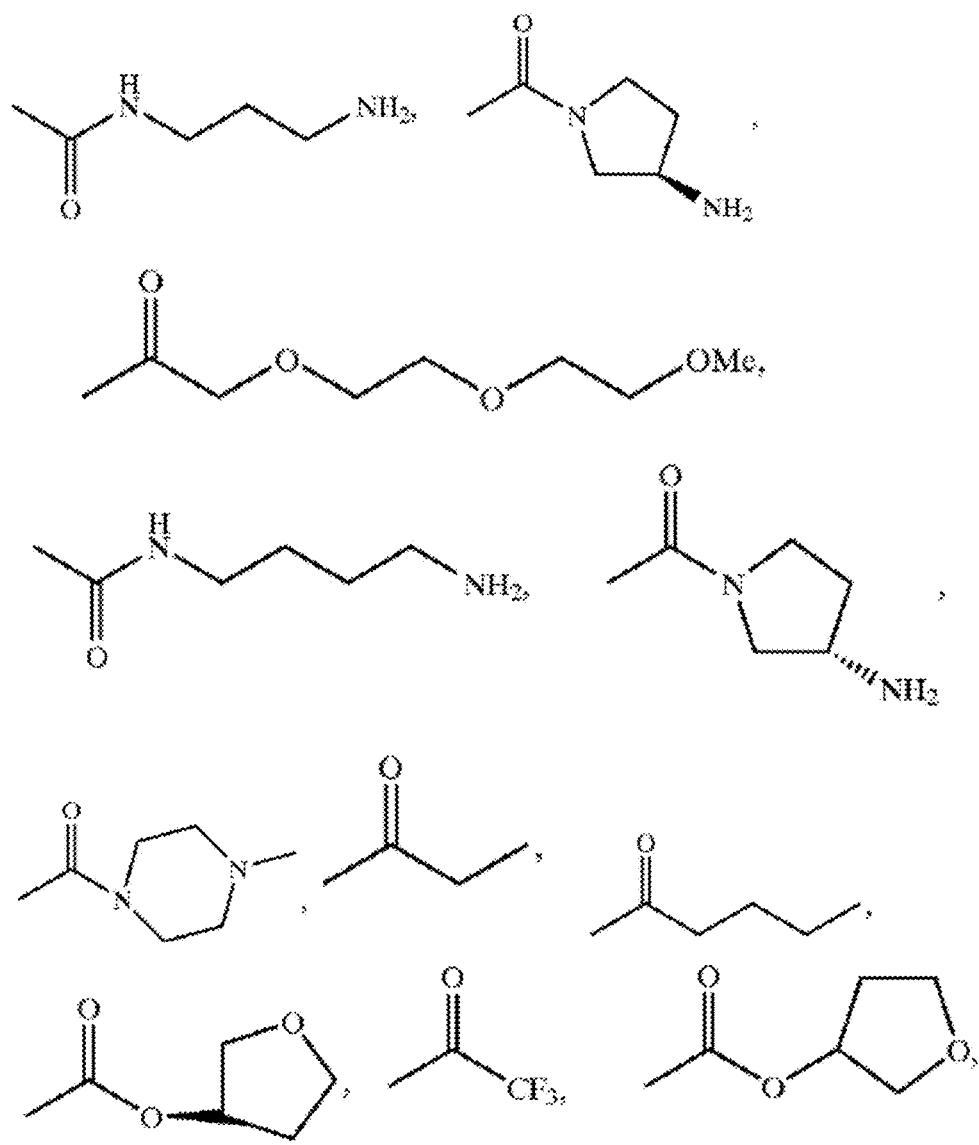
Figure 6C:
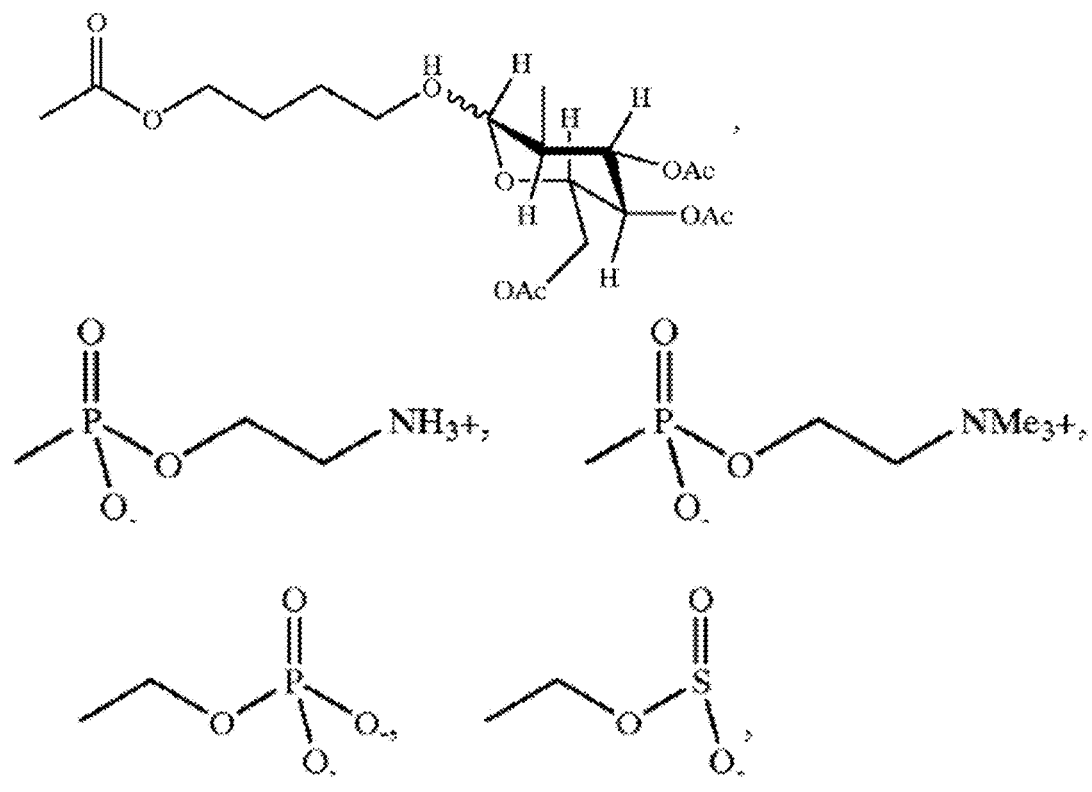

In more specific embodiments, $P^1$ is selected from a heterocyclocarbonyl listed in FIG. 5-1 and 5-2, herein. In more specific embodiments, $R^3$ in the above formula is a $C_1$-$C_4$ alkyl or a $C_1$-$C_4$ alkyl substituted by a $C_3$-$C_7$-cycloalkyl group, or a phenyl group. In preferred embodiments, $R^3$ is butyl or isobutyl. In more specific embodiments, $R^2$ in the above formula is a $C_1$-$C_4$ alkyl substituted with a phenyl or a $C_3$-$C_7$ cycloalkyl. In preferred embodiments, $R^2$ is —CH$_2$-phenyl.

Compounds of the above formulas where variables are as defined in U.S. Pat. Nos. 5,968,942, 6,248,775, 6,646,010, 6,417,387 and 6,924,286, and named formulas VI and VII herein, where $R^4$ is BBB can be prepared, from starting materials and reagents that are commercially available or readily prepared by known methods, or routine adaptations thereof, by one of ordinary skill in the art in view of methods described in U.S. Pat. Nos. 5,968,942, 6,248,775, 6,646,010, 6,417,387 and 6,924,286, in view of methods for introducing phenyl boronates, benzoxaboroles and borono-pyridyl groups as described herein and as are known in the art and in view of synthetic methods that are well known in the art. Compounds herein having a boronate group protected with an N-derivatized iminodiacetic acid (see formula above) can be prepared from starting materials and reagents that are commercially available or readily prepared by known methods, or routine adaptations thereof, by one of ordinary skill in the art, in view of descriptions herein and in U.S. Pat. Nos. 8,318,983, 8,557,980 and 8,722,916 as well as in references 14-16.

U.S. Pat. No. 6,436,989 relates to prodrugs of aspartyl protease inhibitors which are useful as prodrugs of HIV protease inhibitors useful for the prevention and treatment of HIV infection and AIDS. This patent is incorporated by reference herein in its entirety for descriptions of the compounds and salts thereof, for methods of synthesis of these compounds and salts thereof, for pharmaceutical compositions comprising the compounds and salts, for pharmaceutical dosage forms of the compounds and salts and for methods of treatment employing these compounds and salts and methods of administration of these compounds and salts to mammals and particularly to humans. Compounds and salts of these patents include those of formula VIII:

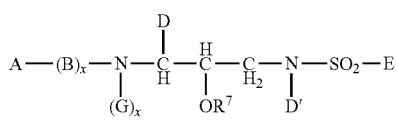

VIII where variables are as defined therein and wherein U.S. Pat. No. 6,436,989 is incorporated herein by reference for the definitions of these variables. In specific embodiments of the patent E is aryl or heteroaryl, among others. It is noted that certain exemplary $R^7$ groups are provided in FIG. 6-1, FIG. 6-2 and FIG. 6-3 herein. In specific embodiments, x is 0, D and D' take values as listed above, x is 0 or 1 and G if present is hydrogen, C1-C4 alkyl, or $R^7$, A is —CO—O-Het, where Het is a 5-7 membered saturated or unsaturated heterocyclic group, containing one or more heteroatoms selected from N, N($R^2$), O, S and S(O)$_n$; heterocyclic group where n is 1 or 2 and $R^2$ is hydrogen or an alkyl group. When G is not present, when x is 0, then the nitrogen to which G is attached is bound directly to the $R^7$ group on —OR$^7$.

The present invention provides compounds and pharmaceutically acceptable derivatives (as defined therein) of formula I therein, where E is BBB BBB which is a phenylboronate group, a benzoxaborole group, a borono-pyridyl group or a protected boronate derivative thereof. In particular BBB is BBB1-BBB11. In particular, BBB is

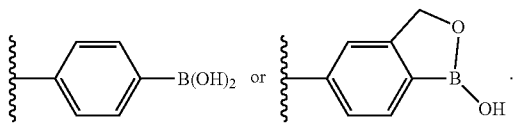 [SMILES: *c1ccc(B(O)O)cc1 ; "or" ; *c1ccc2c(c1)COB2O ; "."]

In a related embodiment, BBB is:

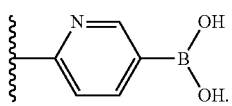

In other embodiments, BBB is BBB9-BBB11.

Compounds of the above formulas I where variables are as defined in U.S. Pat. No. 6,436,989, except that E is BBB can be prepared, from starting materials and reagents that are commercially available or readily prepared by known methods, or routine adaptations thereof, by one of ordinary skill in the art in view of methods described in U.S. Pat. No. 6,436,989, in view of methods for introducing phenyl boronates, benzoxaboroles and boronated pyridyl groups as described herein and as are known in the art and in view of synthetic methods that are well known in the art.

In specific embodiments, the invention provides compounds, salts and prodrugs of formulas X or XI:

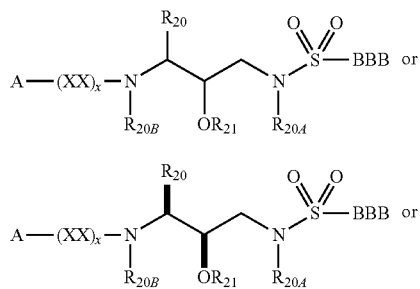

where BBB is a phenylboronate group, a benzoxaborole group, a borono-pyridyl group or a protected boronate derivative thereof, x is 0 or 1 to show the presence or absence of —XX—,
—XX— when present is —O—, —CO—, —S$_2$—, —CO—CO—, —O—CO—, —O—SO$_2$—, —NR$_{10}$—SO$_2$—, —NR$_{10}$—CO— or —NR$_{10}$—CO—CO—; where each R$_{10}$ is independently H, C1-C4 alkyl or C1-C4 alkyl substituted with C$_3$-C$_7$ cycloalkyl;

R$_{20}$, R$_{20A}$ and R$_{20B}$ are independently selected from C$_1$-C$_4$ alkyl, C$_3$-C$_6$ cycloalkyl, C5-C6-cycloalkenyl, phenyl, C1-C4 alkyl substituted with one or more phenyl, or C3-C6 cycloalkyl groups, a C3-C6 cycloalkyl group substituted with or fused to phenyl or a C5-C6 cycloalkyl group substituted with or fused to a phenyl;

R$_{21}$ is selected H; —PO$_3$(R$_3$)$_2$; or —PO$_3$R$_3$H or —PO$_3$H$_2$ or pharmaceutically acceptable salts thereof; or an acyl group (—CO—R$_{22}$), where R$_{22}$ is selected from C1-C4 alkyl, C2-C4 alkenyl, or C2-C10 alkyl wherein one or more —CH$_2$— groups are replaced with —O—; or a C2-C10 alkyl wherein one or more —CH$_2$— groups are replaced with —NH— or one or more —CH$_3$ groups are replaced with —NR$_{23}$, where R$_{23}$ is H or a C1-C4 alkyl; and A is selected from H; Het; C6-C10 aryl; C3-C7 cycloalkyl; C5-C7 cycloalkenyl; C1-C4 alkyl; C2-C4 alkenyl; C1-C4 alkyl substituted with one or more C1-C4 alkoxy, C3-C7 cycloalkyl, C5-C7 cycloalkenyl, C6-C10 aryl, or Het groups, wherein Het is selected from a 5-10 membered saturated, partially saturated or unsaturated cyclic group containing one or more heteroatoms or moieties selected from —N═; —N(R$_{24}$)—; —O—; —S—, —SO—; —SO$_2$—, or —CO—, where R$_{24}$ is selected from H, C1-C4 alkyl, C1-C4 alkyl substituted with a C3-C7 cycloalkyl group, or C1-C4 alkyl substituted with a C6-C10 aryl group; and wherein each R$_{20}$, R$_{22}$, R$_{23}$, R$_{24}$, A or Het group is optionally substituted with one or more oxo, C$_1$-C$_3$-alkoxy, —OH, —C1-C3 alkyl, —CO—R$_{25}$, —N(R$_{25}$)$_2$, —CO$_2$R$_{25}$ (or when R$_{25}$ is H, pharmaceutically acceptable salts thereof), —NR$_{25}$—CO—R$_{25}$, —CO—N(R$_{25}$)$_2$, —(CH$_2$)$_r$—OH (where r is 1 or 2), —CN, —NO$_2$, halo or —CF$_3$, and R$_{25}$ is selected from H or C$_1$-C$_3$ alkyl.

In particular embodiments, BBB is BBB1-BBB11. In particular embodiments, BBB is BBB9-BBB11. In particular embodiments BBB is

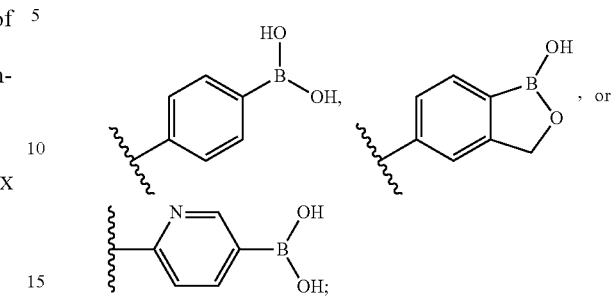

In specific embodiments of formula X, x is 1 and —XX— is present. Preferred —XX— are —O—, —CO—, —SO$_2$—, —O—CO—, and —NR$_{10}$—SO$_2$—. More preferred —XX— is —O—CO—. In specific embodiments, R$_{10}$ is H or —CH$_3$. Preferred R$_{10}$ are H. In specific embodiments, R$_{20B}$ is H or C1-C4 alkyl. Preferred R$_{20B}$ is H. In specific embodiments, R$_{20A}$ is C1-C4 alkyl. In more preferred embodiments, R$_{20A}$ is butyl and isobutyl. In specific embodiments, R$_{20}$ is C1-C4 alkyl substituted with an optionally substitutes phenyl ring. In more specific embodiments, R$_{20}$ is C$_1$-C$_2$ alkyl substituted with unsubstituted phenyl.

In additional embodiments of formulas X and XI, A is selected from unsubstituted Het, unsubstituted C1-C4 alkyl, unsubstituted C2-C4 alkenyl, C6-C10 aryl or a C1-C4 alkyl group substituted with an unsubstituted C6-C10 aryl, or unsubstituted Het group.

In additional embodiments of formulas X and XI, Het is selected from a 5-10 membered saturated cyclic group containing one or two oxygens as ring members or a 5-10 membered saturated or unsaturated group which is optionally substituted with one or two nitrogens as ring members.

In specific embodiment of formulas X and XI, A is a C1-C2 alkyl group substituted with an optionally substituted pyridyl group or a pharmaceutically acceptable salt thereof. In more specific embodiments, A is a C1-C2 alkyl group substituted with a pyrid-2-yl group, a pyrid-3-yl group or a pyrid-4-yl group each of which is unsaturated.

In specific embodiments of formulas X or XI, A is selected from an A group provided in FIG. 4 (pages 1-4). More specifically A is one of A1-A4, or one of A1-A14, or one of A1-A17, or one of A1-A27, or one of A28-A30, or one of A31-A53. In FIG. 4 (pages 1-4), R is H or a C1-C4 alkyl or a C1-C4 alkyl substituted with a C3-C7 cycloalkyl or a phenyl group and is preferably H or —CH$_3$.

In specific embodiments, the invention provides compounds of formulas XXI-XXIV, XXI-N and XXII-N:

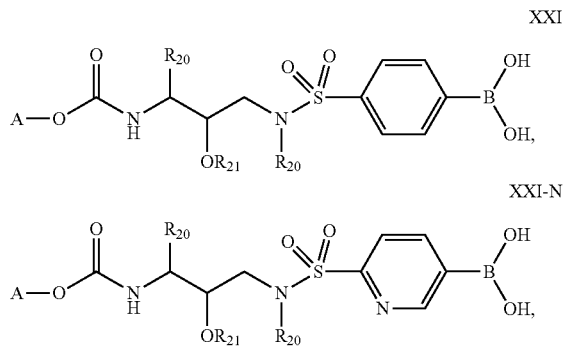

-continued

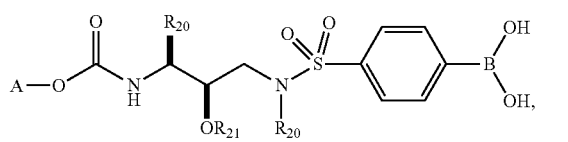
XXII

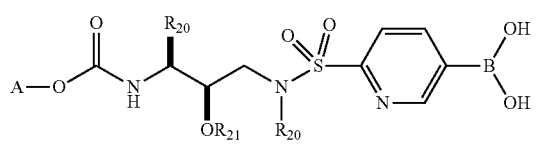
XXII-N

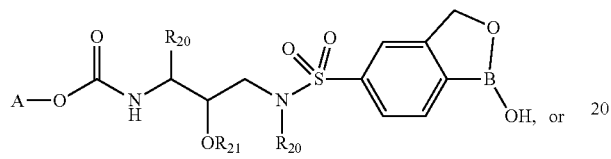
XXIII

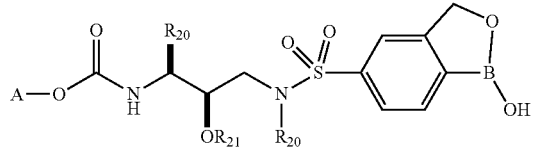
XXIV as well as boronate protected derivatives of formulas XXI, XXI-N, XXII, and XXII-N (see BBB9-BBB11, above) wherein:

each $R_{20}$ is independently selected from C1-C4 alkyl, C3-C6 cycloalkyl, C5-C6-cycloalkenyl, phenyl, C1-C4 alkyl substituted with one or more phenyl, or C3-C6 cycloalkyl groups, a C3-C6 cycloalkyl group substituted with or fused to phenyl or a C5-C6 cycloalkyl group substituted with or fused to a phenyl;

$R_{21}$ is selected H; —$PO_3(R_3)_2$; or —$PO_3R_3H$ or —$PO_3H_2$ or pharmaceutically acceptable salts thereof; or an acyl group (—CO—$R_{22}$), where $R_{22}$ is selected from C1-C4 alkyl, C2-C4 alkenyl, or C2-C10 alkyl wherein one or more —$CH_2$— groups are replaced with —O—; or a C2-C10 alkyl wherein one or more —$CH_2$— groups are replaced with —NH— or one or more —$CH_3$ groups are replaced with —$NR_{23}$, where $R_{23}$ is H or a C1-C4 alkyl; and A is selected from H; Het; C6-C10 aryl; C3-C7 cycloalkyl; C5-C7 cycloalkenyl; C1-C4 alkyl; C2-C4 alkenyl; C1-C4 alkyl substituted with one or more C1-C4 alkoxy, C3-C7 cycloalkyl, C5-C7 cycloalkenyl, C6-C10 aryl, or a Het group, and Het is selected from a 5-10 membered saturated or unsaturated cyclic group containing one or more heteroatoms or moieties selected from —N=; —N($R_{24}$)—; —O—; —S—, —SO—; —$SO_2$—, or —CO—, where $R_{24}$ is selected from H, C1-C3 alkyl, or C1-C3 alkyl substituted with a C6-C10 aryl group; and wherein each $R_{20}$, $R_{22}$, $R_{23}$, $R_{24}$, A or Het group is optionally substituted with one or more oxo, C1-C3-alkoxy, —OH, —C1-C3 alkyl, —CO—$R_{25}$, —N($R_{25}$)$_2$, —$CO_2R_{25}$ (or when $R_{25}$ is H, pharmaceutically acceptable salts thereof), —$NR_{25}$—CO—$R_{25}$, —CO—N($R_{25}$)$_2$, —$(CH_2)_r$—OH (where r is 1 or 2), —CN, —$NO_2$, halo or —$CF_3$, and $R_{25}$ is selected from H or C1-C3 alkyl.

In more specific embodiments, each $R_{20}$, $R_{22}$, $R_{23}$, $R_{24}$, A or Het group is optionally substituted with one of the above recited substituent groups.

In more specific embodiments, each $R_{20}$, $R_{22}$, $R_{23}$, $R_{24}$, A or Het group is optionally substituted with one to three groups selected from oxo, —$OCH_3$, —OH, —C1-C3 alkyl, —COH, —$COCH_3$, —$NH_2$, —$CO_2H$ or salts thereof, —NH—CO—H, —NH—CO—$CH_3$, —CO—$NH_2$, —$CH_2CH_2$—OH, —CN, —$NO_2$, halo or —$CF_3$. In more specific embodiments, each $R_{20}$, $R_{22}$, $R_{23}$, $R_{24}$, A or Het group is optionally substituted with one to three groups selected from —OH, —COH, —$COCH_3$, —$NH_2$, —CO—$NH_2$, —CN, —$NO_2$, halo or —$CF_3$. In more specific embodiments, each $R_{20}$, $R_{22}$, $R_{23}$, $R_{24}$, A or Het group is optionally substituted with one to three groups selected from —OH, —$NH_2$, —$NO_2$, halo or —$CF_3$. In specific embodiments, the two instances of $R_{20}$ are different groups.

In more specific embodiments the compounds have formulas XXVI, XXVII, XXVIII, XXIX, XXVI-N or XXVII-N:

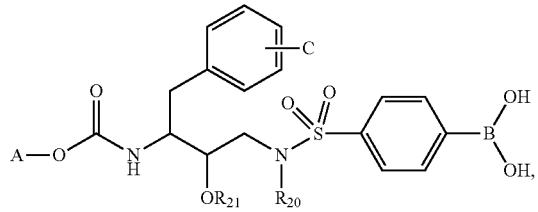
XXVI

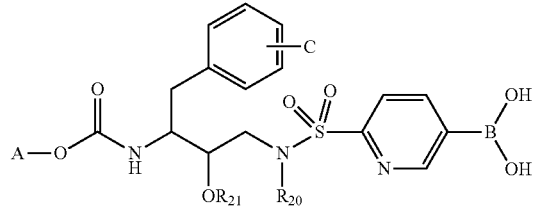
XXVI-N

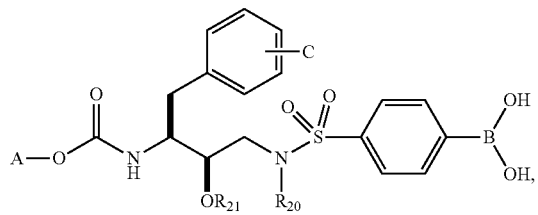
XXVII

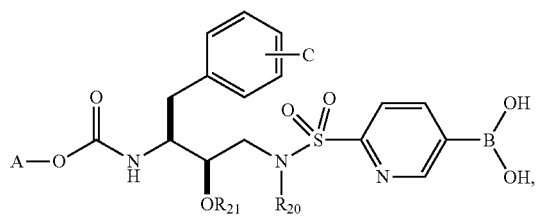
XXVII-N

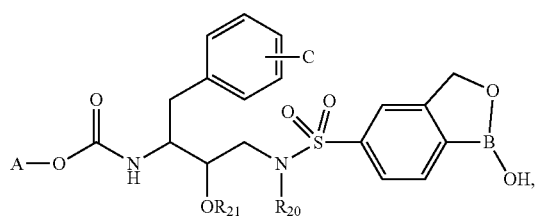
XXVIII

XXIX

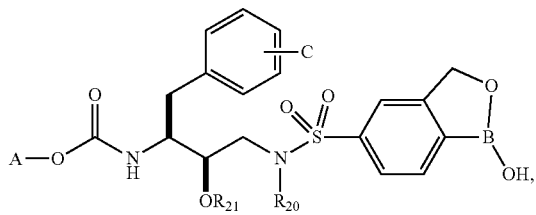

or boronate protected derivatives of compounds of formulas XXVI, XXVI-N, XXVII and XXVII-N (see BBB9-BBB11), where variables are defined for formulas XXI-XXIV and C represents optional substitution of the indicated ring by one or more groups selected from oxo, C1-C3-alkoxy, —OH, —C1-C3 alkyl, —CO—$R_{25}$, —N($R_{25}$)$_2$, —CO$_2R_{25}$, —NR$_{25}$—CO—$R_{25}$, —CO—N($R_{25}$)$_2$, —(CH$_2$)$_r$—OH, —CN, —NO$_2$, halo or —CF$_3$, and $R_{25}$ is selected from H or C1-C3 alkyl. In more specific embodiments, C represents substitution with one to three groups selected from oxo, C1-C3-alkoxy, —OH, —C1-C3 alkyl, —CO—H, —CO—CH$_3$, —NH$_2$, —CO$_2$H, —NR$_{25}$—CO—$R_{25}$, —CO—NH$_2$, —(CH$_2$)—OH, —CN, —NO$_2$, halo or —CF$_3$, and $R_{25}$ is selected from H or C1-C3 alkyl. In more specific embodiments, C represents substitution with one of the listed groups. In more specific embodiments, C represents substitution with one to three groups selected from —OH, —COH, —COCH$_3$, —NH$_2$, —CO—NH$_2$, —CN, —NO$_2$, halo or —CF$_3$. In more specific embodiments, C represents substitution with one to three groups selected from —OH, —NH$_2$, —NO$_2$, halo or —CF$_3$.

In a particular embodiment of formulas XXVI-XXIX, C is —OR$_C$ where R$_C$ is selected from C1-C6 alkyl group, a C1-C6 alkyl substituted with a phenyl group, a C1-C6 group substituted with a C4-C7 cycloalkyl group, a C1-C6 alkyl group substituted with a 5-7 membered saturated, partially saturated or unsaturated heterocyclic group wherein the heterocyclic ring has one or more heteroatom groups in the ring selected from —O—, —N=, —S—, —SO—, —SO$_2$—, or —N(R$_{C5}$)— and/or wherein the heterocyclic ring is substituted with one to four substituents selected from C1-C3 alkyl, —CF$_3$, halo, C1-C3 alkoxy, or phenyl and R$_{C5}$ is H or C1-C3 alkyl. In a specific embodiment, R$_C$ is a C1-C2 alkyl substituted with the 5-7 member heterocyclic ring. In a more specific embodiment, R$_C$ is a C1-C2 alkyl substituted with a 5-member heterocyclic ring as noted above having —O—, —N=, —S—, or —N(R$_{C5}$)— in the ring and being optionally substituted with one or more C1-C3 alkyl groups. In a more specific embodiment —OR$_C$ is:

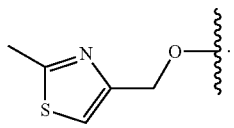 [SMILES: *OCc1csc(C)n1 ; "."]

In additional embodiments of formulas XXI-XXIX, A is selected from unsubstituted Het, unsubstituted C1-C4 alkyl, unsubstituted C2-C4 alkenyl, unsubstituted C6-C10 aryl or a C1-C4 alkyl group substituted with an unsubstituted C6-C10 aryl, or unsubstituted Het group.

In additional embodiments of formulas XX-XXIX, Het is selected from a 5-10 membered saturated cyclic group containing one or two oxygens as ring members or a 5-10 membered saturated or unsaturated group which is optionally substituted with one or two nitrogens as ring members.

In specific embodiment of formulas XXI-XXIX, A is a C1-C2 alkyl group substituted with an optionally substituted pyridyl group or a pharmaceutically acceptable salt thereof. In more specific embodiments, A is a C1-C2 alkyl group substituted with a pyrid-2-yl group, a pyrid-3-yl group or a pyrid-4-yl group each of which is unsaturated.

In specific embodiments of formulas XXI-XXIX, A is selected from an A group provided in FIG. 4 (pages 1-4). More specifically A is one of A1-A4, or one of A1-A14, or one of A1-A17, or one of A1-A27, or one of A28-A30, or one of A31-A53.

In specific embodiments of formulas XXI-XXIX, $R_{20}$ is a benzyl or an C1-C4 alkyl; $R_{21}$ is selected from H; —PO$_3$(R$_{31}$)$_2$; or —PO$_3$R$_{31}$H or —PO$_3$H$_2$ or pharmaceutically acceptable salts thereof; and A is A$_1$ or A$_2$.

In more specific embodiments, the invention provides the compounds of formulas XXXI-XXXIV, XXXI-N and XXXIII-N:

XXXI

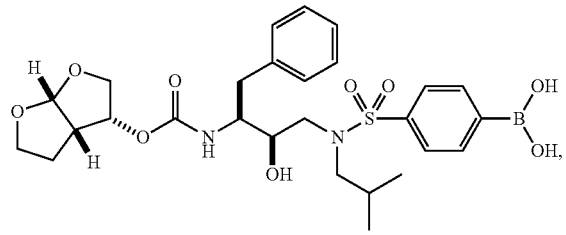

XXXI-N

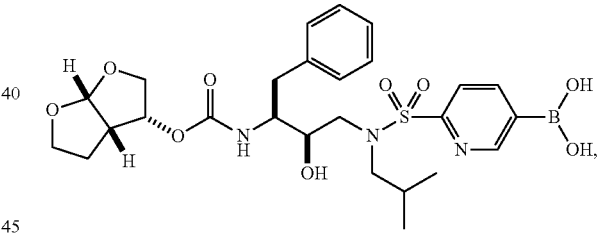

XXXII

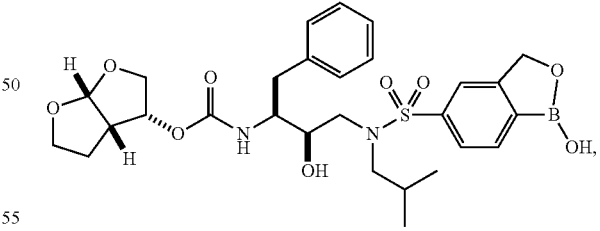

XXXIII

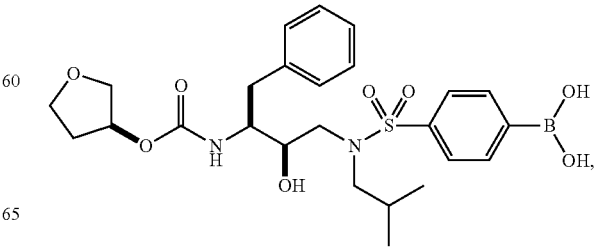

XXXIII-N

XXXIV or boronate protected derivatives of compounds of formulas XXXI, XXXI-N, XXXIII and XXXIII-N (see BBB9-BBB11).

In other embodiments, the invention provides prodrugs of formulas X, XI, XXI-XXIX, XXI-NXXIII-N, XXXI-XXXIV, XXXI-N, XXXIII-N, (above where H is replaced with $R_{21}$) and XLI-XLIV and XLI-N and XLIII-N:

XLI

XLI-N

XLII

XLIII

XLIII-N

XLIV or boronate protected derivatives of compounds of formulas XLI, XLI-N, XLIII and XLIII-N (see BBB9-BBB11), wherein $R_{21}$ is independently selected from groups:

YY1

YY2 wherein:
each x is independently 0 or 1;
Z is —O—, —S—, —N($R_{27}$)— or, when M is absent Z is H;
Y is P or S;
X is O or S;
wherein when Y is S, Z is not S;
—$R_{26}$— is —C($R_{27}$)$_2$—, —O—, or —N($R_{27}$)—;
each $R_{27}$ is independently H; C1-C4 alkyl; or a C1-C4 alkyl substituted with a 3-7 membered saturated, partially saturated or unsaturated carbocyclic group or a 5-7 membered saturated, partially saturated or unsaturated heterocyclic group containing one or more heteroatoms or moieties selected from —O—, —N═, —S—, —SO—, SO$_2$— or —N($R_{28}$)—, where $R_{28}$ is H or a C1-C4 alkyl; and wherein each alkyl group, carbocyclic group or heterocyclic group of $R_{27}$ is optionally substituted with one or more groups selected from oxo, —$OR_{28}$, —C1-C4 alkyl, —$N(R_{28})_2$, —$N(R_{28})$—CO—$R_{28}$, —$(CH_2)_r$OH, (where r is 1-4), —CN, —$CO_2R_{28}$, —CO—$N(R_{28})_2$, halo or —$CF_3$;

each M is independently selected from H, cation having a +1 or +2 charge (e.g., $Li^+$, $Na^+$, $K^+$, $Mg^{2+}$, $Ca^{2+}$, $Ba^{2+}$, —$N(R_{27})_4^+$), C1-C12 alkyl, C2-C12 alkenyl, wherein 1 to 4 —$CH_2$— groups of the alkyl or alkenyl group, other than the —$CH_2$— that is bound to Z, is optionally replaced by a heteroatom group selected from —O—, —S—, —SO—, —$SO_2$—, or —$N(R_{27})$—; or M is $R_{30}$ which is selected from a 5-10 membered saturated, partially saturated or unsaturated carbocyclic or heterocyclic group wherein the heterocyclic groups contains one or more heteroatom groups selected from —O—, —S—, —SO—, —$SO_2$—, or —$N(R_{27})$— and wherein the carbocyclic or heterocyclic groups are optionally substituted with one to four substituents selected from —OH, C1-C4 alkyl, C1-C4 alkoxy, or —O—CO—C1-C4 alkyl; and wherein any hydrogen(s) in said alkyl, alkenyl, carbocyclic or heterocyclic groups of M are optionally replaced with a substituent selected from oxo, —$OR_{28}$, C1-C4 alkyl, C3-C7 cycloalkyl, C5-C6 cycloalkenyl, C6-C10 aryl, C5-C10 heterocyclic, —$N(R_{28})_2$, —$N(R_{28})_3^+$, —$(CH_2)_r$—OH, (where r is 1-4), —CN, —$CO_2R_{28}$, —CO—$N(R_{28})_2$, —$SO_2$—$N(R_{28})_2$, —$N(R_{28})$—CO—$R_{28}$, —CO—$R_{28}$, —SO—$R_{28}$, —$SO_2$—$R_{28}$, —$OCF_3$, —SO—$R_{29}$, —$SO_2$—$R_{29}$, —$N(R_{28})$—$SO_2$—$R_{28}$, halo, —$CF_3$, or —$NO_2$;

$R_{29}$ is selected from a 5-10 membered saturated, partially saturated or unsaturated carbocyclic or heterocyclic group wherein the heterocyclic group contains one or more heteroatom groups selected from —O—, —S—, —SO—, —$SO_2$—, or —$N(R_{27})$— and wherein the carbocyclic or heterocyclic groups are optionally substituted with one to four substituents selected from —OH, C1-C4 alkyl, C1-C4 alkoxy, or —O—CO—C1-C4 alkyl; and wherein any hydrogen(s) in said alkyl, alkenyl, carbocyclic or heterocyclic groups of M are optionally replaced with a substituent selected from oxo, —$OR_{28}$, C1-C4 alkyl, —$N(R_{28})_2$, —$N(R_{28})_3^+$, —$(CH_2)_r$—OH, (where r is 1-4), —CN, —$CO_2$—$R_{28}$, —CO—$N(R_{28})_2$, —$SO_2$—$N(R_{28})_2$, —$N(R_{28})$—CO—$R_{28}$, —CO—$R_{28}$, —SO—$R_{28}$, —$SO_2$—$R_{28}$, —$OCF_3$, —$N(R_{28})$—$SO_2$—$R_{28}$, halo, —$CF_3$, or —$NO_2$; and M' is H, C1-C12-alkyl, C2-C12-alkenyl, or $R_{30}$; wherein 1 to 4 —$CH_2$— groups of the alkyl or alkenyl group are optionally replaced by a heteroatom group selected from —O—, —S—, —SO—, —$SO_2$—, or —$N(R_{27})$—; and wherein any hydrogen(s) in said alkyl, alkenyl, or $R_{30}$ are optionally replaced with a substituent selected from oxo, —$OR_{28}$, C1-C4 alkyl, —$N(R_{28})_2$, —$N(R_{28})_3^+$, —$(CH_2)_r$OH, (where r is 1-4), —CN, —$CO_2R_{28}$, —CO—$N(R_{28})_2$, —$SO_2$—$N(R_{28})_2$, —$N(R_{28})$—CO—$R_{28}$, —CO—$R_{28}$, —SO—$R_{28}$, —$SO_2$—$R_{28}$. —$OCF_3$, —SO—$R_{29}$, —$SO_2$—$R_{29}$, —$N(R_{28})$—$SO_2(R_{28})$, halo, —$CF_3$, or —$NO_2$.

Those of ordinary of skill in the art will understand that M or M' in YY1 and YY2 have a covalent, a covalent/zwitterionic, or an ionic bonding relationship with $R_{26}$ or Z depending upon the selection of $R_{26}$, Z, M or M'. For example, when M or M' is hydrogen, alkyl, alkenyl, or $R_{30}$, M or M' is covalently bound to $R_{26}$ or Z. If M is a mono- or divalent metal cation or other positively charged species (e.g., $NH_4^+$), there is an ionic bonding interaction between M and Z and the resulting compound is a salt. When x is 0 in (M)x (formula YY1), M is not present and Z may be a charged species. In this case the other M in this formula may be oppositely charged to produce a net zero charge on the molecule. Alternatively, the counter ion may located elsewhere in the molecule.

In specific embodiments, M is a pharmaceutically acceptable cation.

In specific embodiments, $R_{21}$ is selected from a group illustrates in FIG. 5 (pages 1-3).

In specific embodiments of formulas X, XI, XXI-XXIX and XLI-XLIV and boronate protected derivatives thereof, $R_{21}$ is selected from H; —$PO_3(R_{31})_2$; or —$PO_3R_{31}$H or —$PO_3H_2$ or pharmaceutically acceptable salts thereof; or an acyl group (—CO—$R_{22}$), where $R_{22}$ is selected from C1-C4 alkyl, C2-C4 alkenyl, or C2-C10 alkyl wherein one or more —$CH_2$— groups are replaced with —O—; or a C2-C10 alkyl wherein one or more —$CH_2$— groups are replaced with —NH— or one or more —$CH_3$ groups are replaced with —$NR_{23}$, where $R_{23}$ is H or a C1-C4 alkyl and wherein $R_{31}$ is selected from H, Het, C6-C10 aryl, C1-C6 alkyl, C2-C6 alkenyl, C3-C6 cycloalkyl, or C5-C6 cycloalkenyl, wherein any group of $R_{31}$ is optionally substituted with one or more —$OR_{32}$, —CO—NH—$R_{32}$, —SO—$N(R_{32})_2$, —$SO_2$—$N(R_{32})_2$, Ht, —CN, —$SR_{32}$, —$CO_2R_{32}$, —$NR_{32}$—CO—$R_{32}$, where $R_{32}$ is H, C1-C4 alkyl or C1-C4 alkyl substituted with a 3-7 membered saturated, partially saturated or unsaturated carbocyclic group; or a 5-7 membered saturated, partially saturated or unsaturated heterocyclic group containing one or more heteroatom groups selected from —O—, —N=, —S—, —SO—, —$SO_2$—, or —$N(R_{32})$—, wherein the carbocyclic or heterocyclic group is optionally substituted with one or more groups selected from oxo, —$OR_{32}$, C1-C4 alkyl, —$N(R_{32})_2$, —$N(R_{32})$—CO—$R_{32}$, —$(CH_2)_r$—OH (where r is 1-4), —CN, —$CO_2R_{32}$, —CO—$N(R_{32})_2$, halo or —$CF_3$.

In more specific embodiments of formulas X, XI, XXI-XXIX and XLI-XLIV, and boronate protected derivatives thereof, $R_{21}$ is selected from acyl groups, particularly —COH and acetyl groups. In more specific embodiments, $R_{21}$ is selected from acyl groups derived from amino acids (bonded through the carboxy), particularly those of L-amino acids, including seryl, lysyl, tyrosyl, valyl, histidyl, α-aspartyl, γ-glutamyl, β-aspartyl, β-glutamyl, pyridylalanyl, γ-alkyl-α-aspartyl (e.g., C1-C4-alkyl-O—CO—$CH_2$—CH($NH_2$)—CO—).

In more specific embodiments of formulas X, XI, XXI-XXIX and XLI-XLIV, and boronate protected derivatives thereof, $R_{21}$ is selected from —$SO_3^{2-}$, and —$CH_2$—$OSO_3^{2-}$ and pharmaceutically acceptable salts thereof, particularly sodium, potassium, calcium, magnesium and ammonium salts thereof.

In more specific embodiments of formulas X, XI, XXI-XXIX and XLI-XLIV, and boronate protected derivatives thereof, $R_{21}$ is selected from H; —$PO_3(R_{31})_2$; or —$PO_3R_{31}$H or —$PO_3H_2$ or pharmaceutically acceptable salts thereof wherein $R_{31}$ is H, optionally substituted C1-C6 alkyl, or optionally substituted C6-C10 aryl. In more specific embodiments, $R_{31}$ is H; C1-C6 alkyl optionally substituted with one or more, —C1-C4 alkoxy, —OH, —$NH_2$, or —N(C1-C4 alkyl); a C1-C4 alkyl optionally substituted with a phenyl group or a phenyl group wherein said phenyl groups are optionally substituted with one or more —C1-C4 alkoxy, —OH, —$NH_2$, or —N(C1-C4 alkyl).

In more specific embodiments of formulas X, XI, XXI-XXIX and XLI-XLIV, and boronate protected derivatives thereof, $R_{21}$ is selected from —$PO_3H_2$, —$PO_3H^-$, —$PO_3^{2-}$, —$CH_2$—$OPO_3H_2$, —$CH_2$—$OPO_3H^-$, —$CH_2$—$OPO_3^{2-}$ and pharmaceutically acceptable salts thereof, including in particular sodium, potassium, calcium, magnesium and ammonium salts thereof.

The invention specifically provides prodrugs which are compounds or pharmaceutically acceptable salts of formulas XXXVI-XXXIX and XXXVI-N and XXXVIII-N:

XXXVI

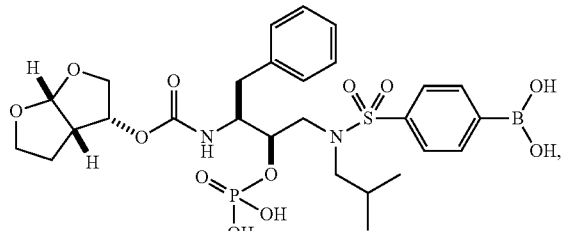

XXXVI-N

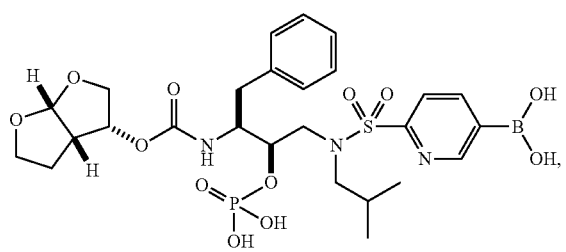

XXXVII

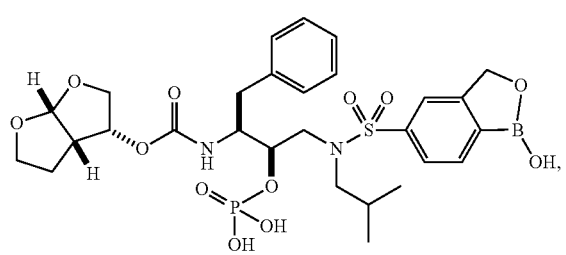

XXXVIII

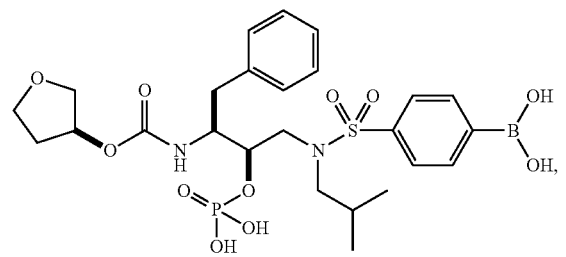

XXXVIII-N

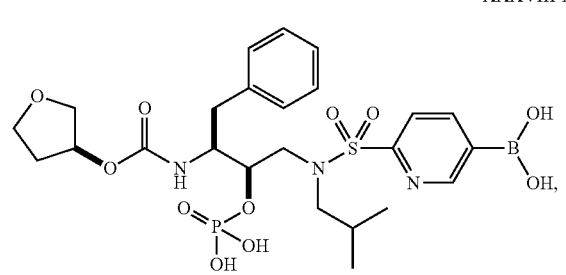

XXXIX

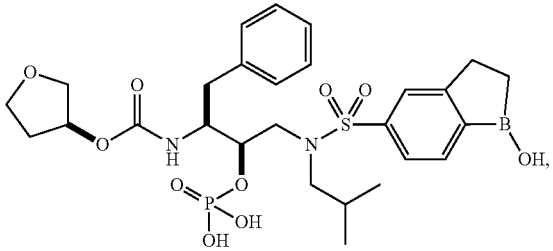

or boronate protected derivatives of compounds of formulas XXXVI, XXXVI-N, XXXVIII and XXXVIII-N (see BBB9-BBB11).

In specific embodiments of salts of formulas XXXVI-XXXIX and of boronate protected derivatives of formulas XXXVI, XXXVI-N, XXXVIII and XXXVIII-N are sodium, potassium, magnesium or calcium salts.

U.S. Pat. Nos. 5,852,195 and 6,169,181 describe HIV protease inhibitors having an aryl sulfonamide group. Each of these patents is incorporated by reference herein in its entirety for the description therein of such compounds and salts thereof and methods of synthesizing such compounds.

Among the compounds in these patents are compounds of formulas therein:

IB

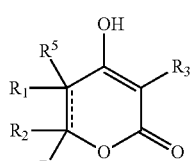

IIB

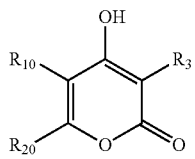

wherein $R^3$ is the moiety of formula VB or XB:

VB

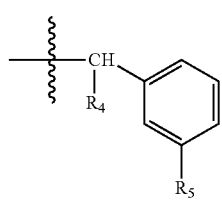

XB

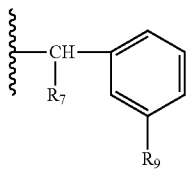

where $R_5$ and $R_9$ are, among other groups, an $-NR_{12}-SO_2$-phenyl group, where the other variables are as defined in U.S. Pat. Nos. 5,852,195 and 6,169,181. The present invention includes compounds and salts thereof as described in U.S. Pat. Nos. 5,852,195 and 6,169,181 wherein the aryl group linked to $-SO_2-$ in such $R_5$ and $R_9$ groups as described therein is replaced with a phenyl boronate, benzoxaborole group, a borono-pyridyl group, or an analogous boronate protected group, particularly as in $R_3$ groups as defined therein which have formula V/X-boronate, V/X benzboronate and V/X borono-pyridyl:

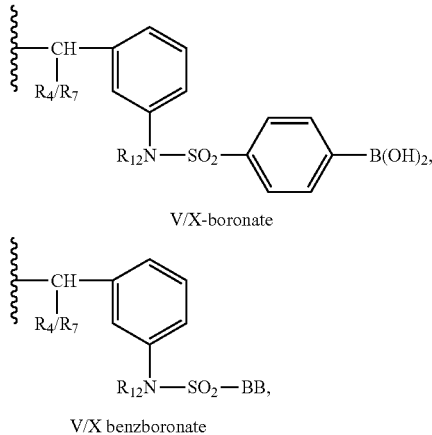

V/X-boronate

V/X benzboronate where BB is:

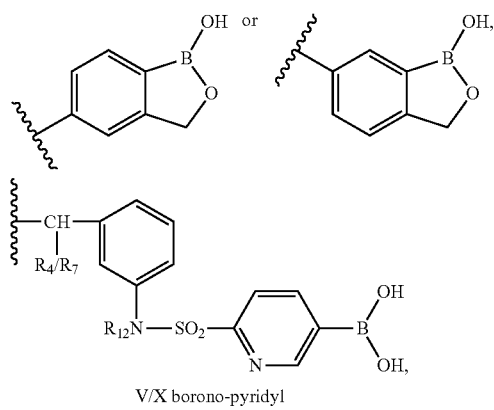

V/X borono-pyridyl or
boronate protected derivatives of V/X-boronate or V/X-boronopyridyl,
where $R_4$, $R_7$ and $R_{12}$ are as defined in U.S. Pat. Nos. 5,852,195 and 6,169,181. In specific embodiments, the compounds of this invention have structures IAA or IBB:

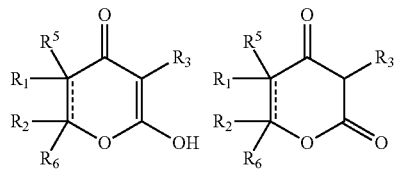

or
structure VIBB:

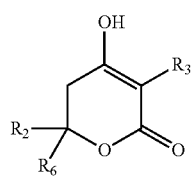

where variables other than $R_3$ are as defined in U.S. Pat. Nos. 5,852,195 and 6,169,181. Compounds of the present invention include those of formulas I, IA, IB, II and VI as defined in U.S. Pat. Nos. 5,852,195 and 6,169,181 where $R_3$ is the formula V/X-boronate, the formula V/X benzoxaborole, the formula V/X borono-pyridinyl above or protected boronate derivatives thereof.

In specific embodiments of formulas I, IAA, IBB, IIBB and VIBB above $R_2$ and $R_6$ are independently selected from C3-C5 alkyl; C2-C6 haloalkyl; C1-C12 alkyl substituted with halo, —$N_3$, phenyl, C3-C7 cycloalkyl, C5-C6 cycloalkenyl, Het, —$NH_2$—$SO_2$—Het; phenyl, substituted with one or more halo, C1-C4 alkyl, C1-C4 haloalkyl, C3-C7 cycloalkyl, C5-C6 cycloalkenyl, Het, or —$NH_2$—$SO_2$—Het; C3-C12 alkyl wherein one or more —$CH_2$— groups are replaced with —O— and/or one or more —$CH_3$ are replaced with —OH; C2-C12 alkyl wherein one or more —$CH_2$— groups are replaced with —$NR_{41}$— and/or one or more —$CH_3$ are replaced with —$N(R_{41})_2$, where $R_{41}$ is H or C1-C4 alkyl; C3-C12 alkyl wherein one or more —$CH_2$— groups are replaced with —O— or —$NR_{41}$— and/or one or more —$CH_3$ are replaced with —OH or —$N(R_{41})_2$, where $R_{41}$ is H or C1-C4 alkyl; C2-C12 alkyl wherein one or more —$CH_2$— groups are replaced with —CO— or —$NR_{41}$— and/or one or more —$CH_3$ are replaced with —$N(R_{41})_2$, —OH, —COOH, or —$SO_3H$, where $R_{41}$ is H or C1-C4 alkyl; or -Het-CO—NH—C1-C3-alkyl;

$R_4/R_7$ is C1-C4 alkyl; and $R_{12}$ is H or C1-C4 alkyl.

In preferred embodiments, $R_2$ and $R_6$ are different groups. In preferred embodiments, $R_4/R_7$ is ethyl, t-butyl or cyclopropyl. In preferred embodiments, $R_{12}$ is H. In preferred embodiments, the compound of this invention is a compound of formula VI as defined in U.S. Pat. Nos. 5,852,195 and 6,169,181, with the exception that $R_3$ is the group of formula V/X-boronate, the group of formula V/X benzoxaborole, the group of the formula of V/X-boronated pyridyl, or protected boronate derivatives thereof.

In specific embodiments, invention provides compounds of formula L, LI, LI-N, LII, LIII or LIII-N:

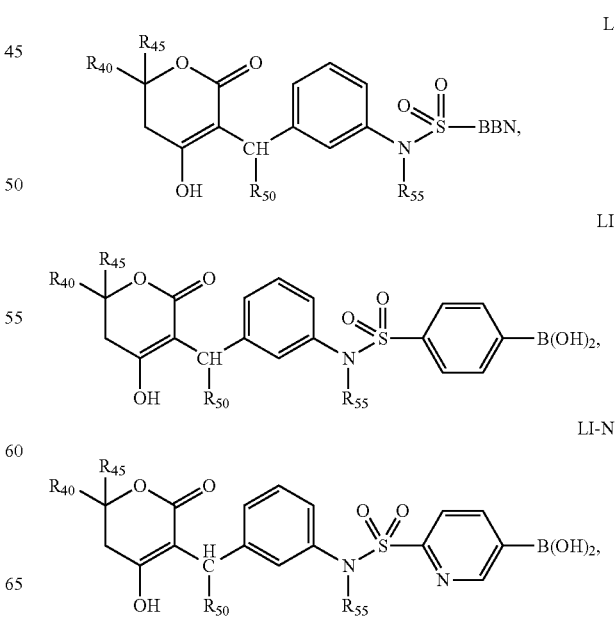

LII

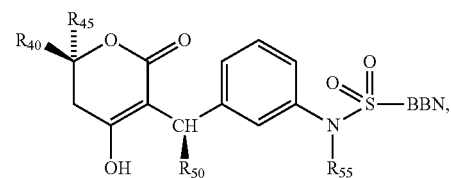

LIII

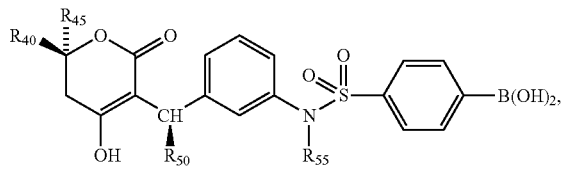

LIII-N

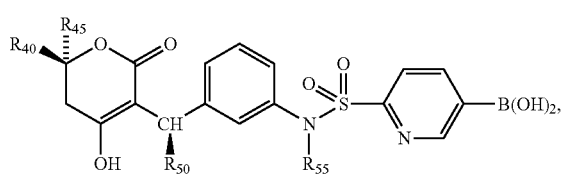

or
boronate protected derivatives of compounds of formulas LI, LI-N, LIII and LIII-N (see BBB9-BBB11),
where, $R_{40}$ and $R_{45}$ are independently selected from C3-C5 alkyl; C2-C6 haloalkyl; C1-C12 alkyl substituted with halo, —$N_3$, phenyl, C3-C7 cycloalkyl, C5-C6 cycloalkenyl, Het, —$NH_2$—$SO_2$-Het;
phenyl, substituted with one or more halo, C1-C4 alkyl, C1-C4 haloalkyl, C3-C7 cycloalkyl, C5-C6 cycloalkenyl, Het, or —$NH_2$—$SO_2$—Het; C3-C12 alkyl wherein one or more —$CH_2$— groups are replaced with —O— and/or one or more —$CH_3$ are replaced with —OH; C2-C12 alkyl wherein one or more —$CH_2$— groups are replaced with —$NR_{41}$— and/or one or more —$CH_3$ are replaced with —$N(R_{41})_2$, where $R_{41}$ is H or C1-C4 alkyl; C3-C12 alkyl wherein one or more —$CH_2$— groups are replaced with —O— or —$NR_{41}$— and/or one or more —$CH_3$ are replaced with —OH or —$N(R_{41})_2$, where $R_{41}$ is H or C1-C4 alkyl; C2-C12 alkyl wherein one or more —$CH_2$— groups are replaced with —CO— or —$NR_{41}$— and/or one or more —$CH_3$ are replaced with —$N(R_{41})_2$, —OH, —COOH, or —$SO_3H$, where $R_{41}$ is H or C1-C4 alkyl; or -Het-CO—NH—C1-C3-alkyl;
$R_{50}$ is C1-C4 alkyl; and
$R_{55}$ is H or C1-C4 alkyl.

In preferred embodiments, $R_{40}$ and $R_{45}$ are different groups. In preferred embodiments, $R_{50}$ is ethyl, t-butyl or cyclopropyl. In preferred embodiments, $R_{55}$ is H.

In preferred embodiments, $R_{40}$ and $R_{45}$ are independently selected from $R_{42}$—$(CH_2)n$-$CH(R_{43})$— where n is 0, 1 or 2; $CH_3$—$[O(CH_2)_2]_2$—$CH_2$—, C3-C5 alkyl, phenyl-$(CH_2)_2$—, Het-$SO_2NH$—$(CH_2)_2$—, $(HOCH_2)_3C$—NH—CO—NH—$(CH_2)_3$—, (HO—CO)($NH_2$)CH—$(CH_2)_2$—CO—NH—$(CH_2)_3$—, piperazin-1-yl-CO—NH—$(CH_2)_3$—, $HO_3S$—$(CH_2)_2$—N($CH_3$)—CO—$(CH_2)_6$—CO—NH—$(CH_2)_3$—, cyclopropyl-$(CH_2)_2$—, F-phenyl-$(CH_2)_2$—, Het-$SO_2NH$-phenyl-, or $CF_3$—$(CH_2)_2$—, wherein $R_{42}$ is selected from phenyl, Het, cyclopropyl, $CH_3$—$[O(CH_2)_2]_2$—, Het-$SO_2NH$—, Br—, $N_3$—, or $HO_3S(CH_2)_2$—N($CH_3$)—CO—$(CH_2)_6$—CO—NH—; and $R_{43}$ is selected from ethyl, or —$CH_2$-cyclopropyl;

In more preferred embodiments, one of $R_{40}$ or $R_{45}$ is C3-C5 alkyl and the other is phenyl-$(CH_2)_2$—, cyclopropyl-$(CH_2)_2$—, F-phenyl-$(CH_2)_2$—, Het-$SO_2NH$-phenyl-, or $CF_3$—$(CH_2)_2$—. In more preferred embodiments, $R_{45}$ is C3-C5 alkyl and $R_{40}$ is phenyl-$(CH_2)_2$—, cyclopropyl-$(CH_2)_2$—, F-phenyl-$(CH_2)_2$—, or Het-$SO_2NH$-phenyl-. In yet more preferred embodiments, $R_{45}$ is n-propyl and $R_{40}$ is phenyl-$(CH_2)_2$—.

In specific embodiments of formulas L and LI, $R_{50}$ is ethyl, $R_{55}$ is H, $R_{45}$ is C3-C5 alkyl and R40 is C1-C2 alkyl substituted with phenyl. In other specific embodiments of formulas L and LI, $R_{50}$ is ethyl, $R_{55}$ is H, $R_{45}$ is n-propyl and $R_{40}$ is —$(CH_2)_2$-phenyl.

Compounds of formulas I, IA, IB, II, VI, L and LI where $R_3$ is the group of formula V/X-boronate, X/V benzoxaborole or X/V borono-pyridinyl can be prepared, from starting materials and reagents that are commercially available or readily prepared by known methods, by one of ordinary skill in the art in view of methods described in U.S. Pat. Nos. 5,852,195 and 6,169,181, in view of methods for introducing phenyl boronates, benzoxaboroles and borono-pyridyl as described herein and as are known in the art and in view of synthetic methods that are well known in the art. Compounds herein having a boronate group protected with an N-derivatized iminodiacetic acid (see formula above) can be prepared from starting materials and reagents that are commercially available or readily prepared by known methods, or routine adaptations thereof, by one of ordinary skill in the art, in view of descriptions herein and in U.S. Pat. Nos. 8,318,983, 8,557,980 and 8,722,916 as well as in references 14-16.

U.S. published application 20100093811, published Apr. 15, 2010, describes HIV protease inhibitors having an aryl sulfonamide group. This published patent application describes compounds of formula LL and provides definition of the variables of this formula. The patent application further describes the compounds and salts thereof and methods of synthesizing such compounds and salts. This published patent application is incorporated by reference herein in its entirety for these descriptions as well as for applications and pharmaceutical compositions containing these compounds and salts. The compounds therein designated lysine sulfonamides have formula (designated formula I therein) and designated formula LL herein:

LL

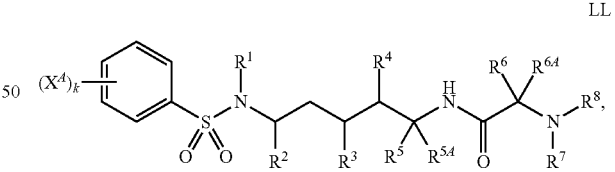

where the definitions of the formula variables are incorporated by reference herein from U.S. published application 20100093811.

In embodiments,
$R^1$ is C1-6 alkyl, C1-6 fluoroalkyl, C3-6 cycloalkyl, or C1-6 alkyl substituted with C3-6 cycloalkyl;
$R^2$ is CH($R^J$)—Z, and Z is OH, NH2, or $OR^P$;
$R^J$ is H, C1-6 alkyl, C1-6 fluoroalkyl, or C1-6 alkyl substituted with C3-5 cycloalkyl;
$R^P$ is P(O)(OH)$_2$, P(O)(OM)$_2$, or C(O)$R^Q$;
M is an alkali metal or an alkaline earth metal;
$R^Q$ is C1-6 alkyl, C3-6 cycloalkyl, C1-6 alkyl substituted with C3-6 cycloalkyl, O—C1-6 alkyl, O—C1-6 alkyl substituted with O—C1-6 alkyl, O—C1-6 fluoroalkyl, C(O)—C1-6 alkyl, C(O)—C1-6 alkylene-N(H)—C1-6 alkyl, C(O)—C1-6 alkylene-N(—C1-6 alkyl)₂, C1-6 alkyl substituted with C(O)O—C1-6 alkyl, C1-6 alkyl substituted with C(O)OH, C1-6 alkyl substituted with C(O)—C1-6 alkyl, N(H)—C1-6 alkyl, N(—C1-6 alkyl)₂, C1-6 alkyl substituted with NH₂, N(H)—C1-6 alkyl, or N(—C1-6 alkyl)₂, AryA, C1-6 alkyl substituted with AryA, O—C1-6 alkyl substituted with AryA, HetA, C1-6 alkyl substituted with HetA, O—C1-6 alkyl substituted with HetA, HetB, or O-HetB;

R³ is H, C1-6 alkyl, C1-6 fluoroalkyl, or C1-6 alkyl substituted with C3-6 cycloalkyl;

R⁴ is H, C1-6 alkyl, C1-6 fluoroalkyl, or C1-6 alkyl substituted with C3-6 cycloalkyl;

R⁵ is H, C1-6 alkyl, C1-6 fluoroalkyl, C1-6 alkyl substituted with OH, C2-6 alkenyl, C2-6 alkynyl, C3-6 cycloalkyl, or C1-6 alkyl substituted with C3-6 cycloalkyl;

R⁵ᴬ is H or C1-6 alkyl;

alternatively, R⁵ and R⁵ᴬ together with the carbon atom to which they are both attached form C3-6 cycloalkyl;

R⁶ is

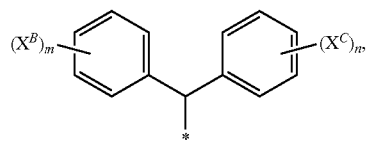

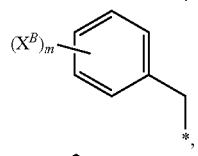

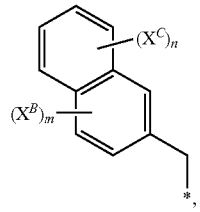

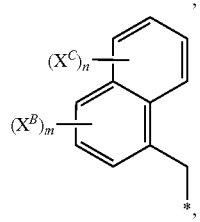

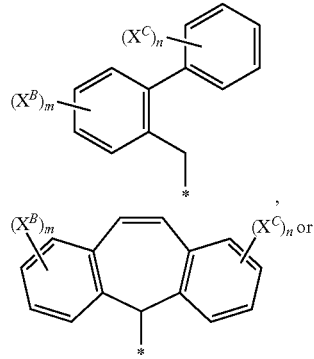

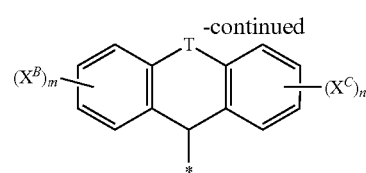

wherein the asterisk (*) denotes the point of attachment to the rest of the compound;

R⁶ᴬ is H or C1-6 alkyl;

alternatively, R⁶ and R⁶ᴬ together with the carbon to which they are attached form a C3-6 cycloalkyl which is optionally substituted with phenyl, wherein the phenyl is optionally substituted with from 1 to 3 X^B.

each X^B and each X^C are independently selected from the group consisting of:
C1-6 alkyl, C3-6 cycloalkyl, C1-6 haloalkyl, OH, O—C1-6 alkyl, O—C1-6 haloalkyl, O—C3-6 cycloalkyl, SH, S—C1-6 alkyl, S—C1-6 haloalkyl, S—C3-6 cycloalkyl, halo, CN, NO₂, NH₂, N(H)—C1-6 alkyl, N(—C1-6 alkyl)2, N(H)C(O)—C1-6 alkyl, N(H)CH(O), CH(O), C(O)—C1-6 alkyl, C(O)OH, C(O)O—C1-6 alkyl, SO₂H, SO₂—C1-6 alkyl; and C1-6 alkyl substituted with: C1-6 haloalkyl, OH, O—C1-6 alkyl, O—C1-6 halo alkyl, O—C3-6 cycloalkyl, SH, S—C1-6 alkyl, halo, CN, NO₂, NH₂, N(H)—C1-6 alkyl, N(—C1-6 alkyl)2, C(O)—C1-6 alkyl, C(O)OH, C(O)O—C1-6 alkyl, or SO₂—C1-6 alkyl;

T is O, S, S(O), or SO₂;

m is an integer equal to 0, 1, 2, or 3;

n is an integer equal to 0, 1, 2, or 3;

R⁷ is H, C1-6 alkyl, C3-6 cycloalkyl, C1-6 alkyl substituted with C3-6cycloalkyl, or C(O)—R^K;

R⁸ is H or C1-6 alkyl;

R^K is: C1-6 alkyl, C3-6 cycloalkyl, C1-6 alkyl substituted with C3-6 cycloalkyl, O—C1-6 alkyl, O—C1-6 alkyl substituted with O—C1-6 alkyl, O—C1-6 fluoro alkyl, C(O)O—C1-6 alkyl, C1-6 alkyl substituted with C(O) O—C1-6 alkyl, C1-6 alkyl substituted with C(O)OH, C1-6 alkyl substituted with C(O)—C1-6 alkyl, N(H)—C1-6 alkyl, N(—C1-6 alkyl)₂, C1-6 alkyl substituted with NH₂, N(H)—C1-6 alkyl, or N(—C1-6alkyl)₂, AryA, C1-6 alkyl substituted with AryA, O—C1-6 alkyl substituted with AryA, HetA, C1-6 alkyl substituted with HetA, O—C1-6 alkyl substituted with HetA, HetB, O-HetB, or O—C1-6 alkyl substituted with HetB;

each AryA is an aryl which is independently phenyl or naphthyl, wherein the phenyl or naphthyl is optionally substituted with from 1 to 4 Y^B wherein each Y^B independently has the same definition as X^B;

each HetA is a heteroaryl which is independently (i) a 5- or 6-membered heteroaromatic ring containing from 1 to 3 heteroatoms independently selected from N, O and S, or (ii) is a heterobicyclic ring selected from quinolinyl, isoquinolinyl, and quinoxalinyl; wherein the heteroaromatic ring (i) or the bicyclic ring (ii) is optionally substituted with from 1 to 4 Y^C wherein each Y^C independently has the same definition as X^B; and each HetB is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or S(O)₂, and wherein the saturated or unsaturated heterocyclic ring is optionally substituted with from 1 to 4 substituents each of which is independently halogen, CN, C1-6 alkyl, OH, oxo, O—C1-6 alkyl, C1-6 haloalkyl, O—C1-6 haloalkyl, C(O)NH$_2$, C(O)N(H)—C1-6 alkyl, C(O)N(—C1-6 alkyl)$_2$, C(O)H, C(O)—C1-6 alkyl, CO$_2$H, CO$_2$—C1-6 alkyl, SO$_2$H, or SO$_2$—C1-6 alkyl.

The present invention includes compounds and salts thereof as described therein wherein the aryl group linked to —SO$_2$— is replaced with a phenyl boronate, a benzoxaborole group or a borono-pyridyl group, or analogous boronate protected groups particularly as in formula LV, LVI, LVII and LVIII:

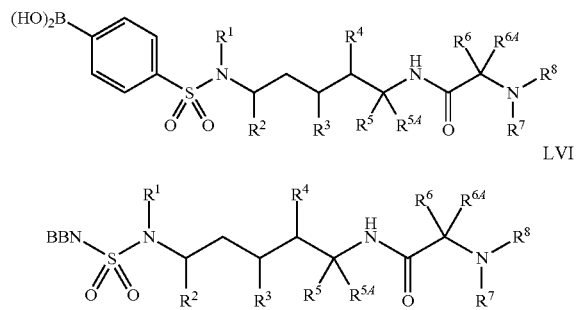

where BBN is defined above, or
boronate protected derivatives of compounds of formulas LVI, or LVII (see BBB9-BBB11),
where BBN is as defined above,
and other variables are defined as in U.S. published application 20100093811 and in embodiments as described above. In specific embodiments $R^6$ and $R^{6A}$ are both phenyl groups. In specific embodiments, $R^2$ is C1-C4 alkyl substituted with an —OH, —NH$_2$, —PO(OH)$_2$ or pharmaceutically acceptable salts thereof, or a —COR$^Q$ group where $R^Q$ is C1-C6 alkyl, C3-C6 cycloalkyl or C1-C6 alkyl substituted with C3-C6 cycloalky or phenyl. In other specific embodiments, $R^2$ is —CH(RJ)-Z where Z is —OH, —NH$_2$, —PO(OH)$_2$ or pharmaceutically acceptable salts thereof, or a —COR$^Q$ group where $R^Q$ is C1-C6 alkyl, C3-C6 cycloalkyl or C1-C6 alkyl substituted with C3-C6 cycloalky or phenyl. In specific embodiments, $R^2$ is —CH$_2$—Z where Z is —OH, —NH$_2$, —PO(OH)$_2$ or pharmaceutically acceptable salts thereof. In specific embodiments, $R^1$ is H or C1-C4 alkyl. In specific embodiments, $R^3$, $R^4$, $R^5$ and $R^{5A}$ are H or C1-C4 alkyl. In specific embodiments, $R^8$ is an acyl group, and in particular is —COR$^K$, where $R^K$ is a phenyl, C1-C4 alkyl, or a C1-C4 alkyl substituted with C3-C7 cycloalkyl, C1-C6 alkoxy or a phenyl. In other specific embodiments, $R^7$ is H or C1-C4 alkyl.

In more specific embodiments, the present invention provides compounds and salts thereof of formulas LVIV-LVVII:

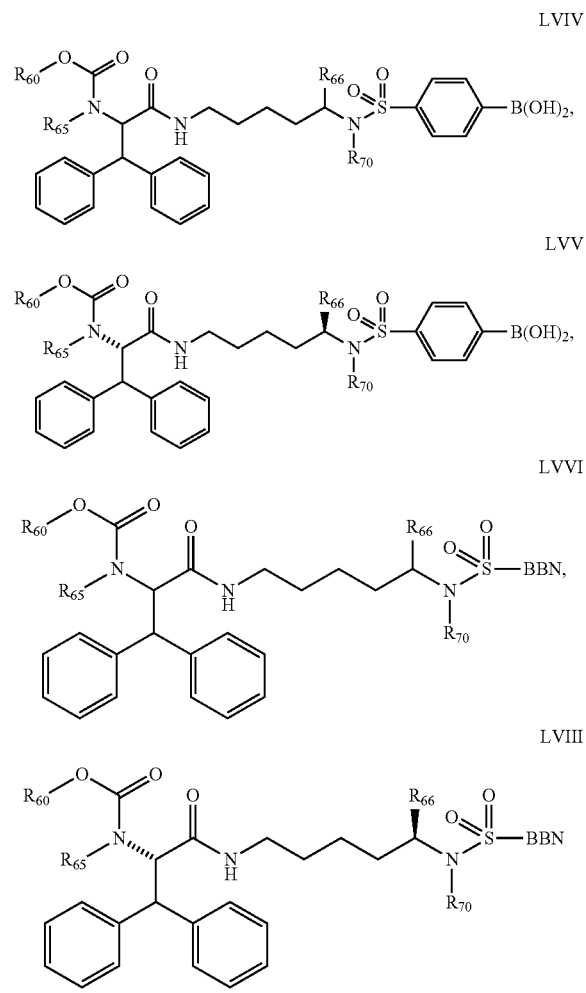

or
boronate protected derivatives of compounds of formulas LVIV and LVV (see BBB9-BBB11),
where:
BBN is as defined above;
$R_{60}$ is an acyl group, —CO—$R_{61}$ where $R_{61}$ is H, C1-C6 alkyl, C3-C7 cycloalkyl or C1-C6 alkyl substituted with C3-C7 cycloalky or phenyl;
$R_{65}$ is hydrogen of C1-C4 alkyl;
$R_{66}$ is —C1-C4 alkyl substituted with Z where Z is —OH, —NH$_2$, —PO(OH)$_2$ or pharmaceutically acceptable salts thereof, or a —COR$^Q$ group where $R^Q$ is C1-C6 alkyl, C3-C6 cycloalkyl or C1-C6 alkyl substituted with C3-C6 cycloalky or phenyl, more preferably $R_{66}$ is —CH$_2$—Z, and yet more preferably Z is —CH$_2$—OH; and
$R_{70}$ is H or C1-C6 alkyl and is preferably C1-C6 alkyl, more preferably butyl and yet more preferably —CH$_2$—CH$_2$(CH$_3$)$_2$.

Lysine sulfonamides of the forgoing formulas can be prepared, from starting materials and reagents that are commercially available or readily prepared by known methods, by one of ordinary skill in the art in view of methods described in U.S. published application 20100093811, in view of methods for introducing phenyl boronate groups, benzoxaborole groups and borono-pyridyl groups as described herein and as are known in the art and in view of synthetic methods that are well known in the art. Compounds herein having a boronate group protected with an N-derivatized iminodiacetic acid (see formula above) can be prepared from starting materials and reagents that are commercially available or readily prepared by known methods, or routine adaptations thereof, by one of ordinary skill in the art, in view of descriptions herein and in U.S. Pat. Nos. 8,318,983, 8,557,980 and 8,722,916 as well as in references 14-16.

U.S. Pat. No. 7,981,929 relates to HIV protease inhibitors having a benzofuran sulfonamide group which have structural features in common with darunavir. Compounds of this patent include brecanavir which has been studied for the treatment of HIV infection, but which was discontinued for problems in formulation. This patent is incorporated by reference herein in its entirety for the description therein of such compounds and salts thereof and methods of synthesizing such compounds. Compounds of this patent have structure of formula MM:

MM

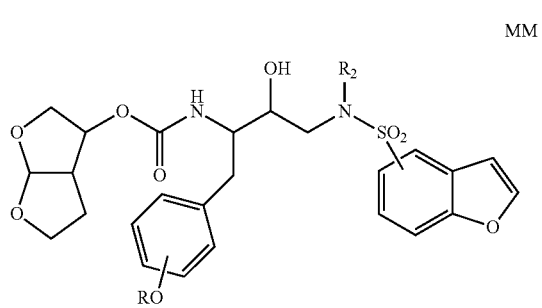

where the definitions of the formula variables are incorporated by reference herein from the patent. The patent also describes prodrugs thereof where the OH group is replaced with —OE where E is defined in the patent. Prodrugs as described are hydrolyzed to the compound of formula MM in vivo.

The present invention includes compounds, salts and any prodrugs thereof as described therein wherein the benzofuran group linked to —SO₂— of formula MM is replaced with a phenyl boronate, a benzoxaborole or a borono-pyridyl group, particularly as in formula M-MV:

M

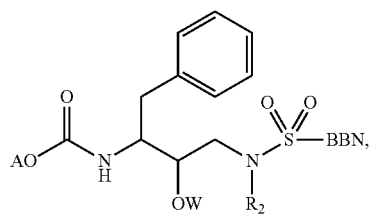

MI

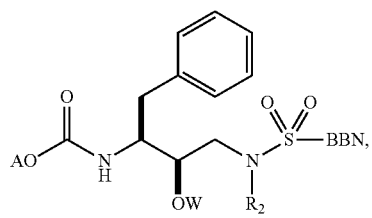

MII

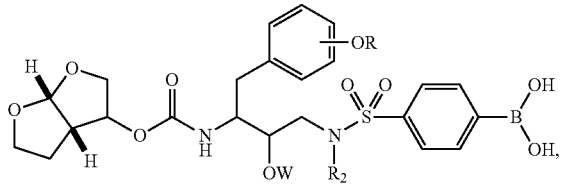

MIII

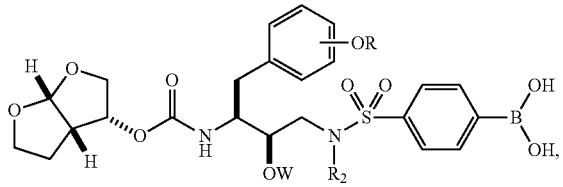

MIV

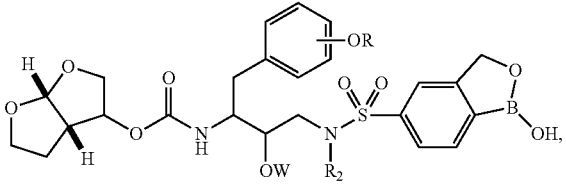

MV

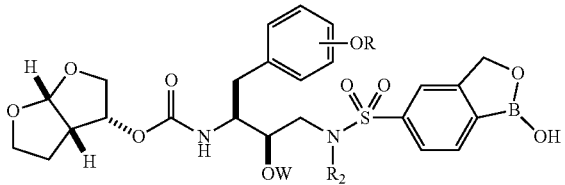

or
boronate protected derivates of compounds of formula M, MI, MII or MIII,
where
BBN is a phenyl boronate group, a benzoxaborole group or a boronated pyridyl group and more specifically is selected from:

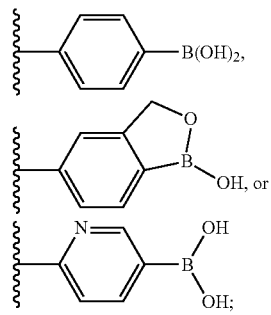

W is H or E, where E, R and R₂ are as defined in U.S. Pat. No. 7,981,929. This patent is incorporated by reference herein in its entirety for descriptions of compounds and variables therein.

In specific embodiments, R₂ is C1-C6 alkyl, C1-C6 alkoxy, C2-C6 alkenyl, C2-C6 alkenyloxy, and C1-C6 alkyl substituted with phenyl or with a C3-C7 cycloalkyl, each of which is optionally substituted with one or more of oxo, halo, —CF₃. C1-C3 alkoxy, —(CH₂)ᵣ—[O—(CH₂)ᵣ—]ₛ—CH₃, where each r and s can be 0, 1, 2 or 3, where at least one r is not zero. In a more preferred embodiment R₂ is butyl and yet more preferred is isobutyl. In specific embodiments, W is H. In specific embodiments, OE is a phosphate, phosphonate or carboxylate ester. In specific embodiments E is selected from H; —PO₃(R₃₁)₂; or —PO₃R₃₁H or —PO₃H₂ or pharmaceutically acceptable salts thereof. In specific embodiments, R is a C1-C6 alkyl group, a C1-C6 alkyl group substituted with a 5-7 membered saturated, partially saturated or unsaturated heterocyclic group or a C1-C6 alkoxly group substituted with a 5-7 membered saturated, partially saturated or unsaturated heterocyclic group, wherein the heterocyclic ring has one or more heteroatom groups in the ring selected from —O—, —N=, —S—, —SO—, —SO₂—, or —N(R₅)— and/or wherein the heterocyclic ring is substituted with one to four substituents selected from C1-C3 alkyl, —CF₃, halo, C1-C3 alkoxy, or phenyl. R₅ is as defined in U.S. Pat. No. 7,981,929, but R₅ is more specifically H or C1-C3 alkyl. In a specific embodiment, R is a C1-C2 alkoxy substituted with the 5-7 member heterocyclic ring. In a more specific embodiment, R is a C1-C2 alkoxy substituted with a 5-member heterocyclic ring as noted above having —O—, —N=, —S—, or —N(R₅)— in the ring and being optionally substituted with one or more C1-C3 alkyl groups. In a more specific embodiment R is:

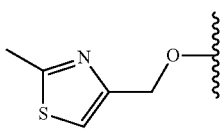 [SMILES: *OCc1csc(C)n1]

In a more specific embodiment, the invention provides compounds and pharmaceutically acceptable salts of formula MV:

MVI

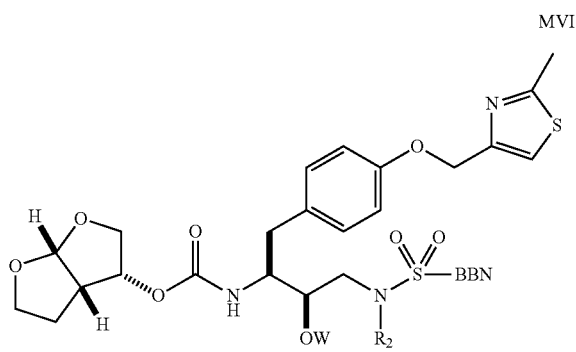

where BBN is a phenylboronate group, a benzoxaborole group, or a borono-pyridyl groups particularly:

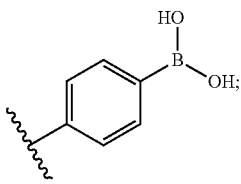

-continued

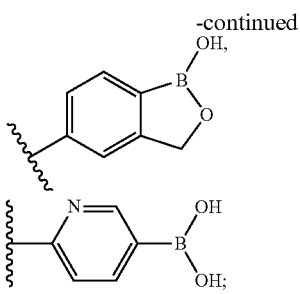

or boronate protected groups there of,

R₂ is butyl and particularly isobutyl. In specific embodiments, W is H. In specific embodiments, W is W where OE is a phosphate, phosphonate or carboxylate ester. In specific embodiments E is selected from H; —PO₃(R₃₁)₂; or —PO₃R₃₁H or —PO₃H₂ or pharmaceutically acceptable salts thereof.

Compounds, salts and any prodrugs thereof of formulas M, MI, MII, MIII, MV, and MM wherein the aryl group bonded to the sulfonamide is replaced with the BBB group can be prepared from starting materials and reagents that are commercially available or readily prepared by known methods, by one of ordinary skill in the art in view of methods described in U.S. Pat. No. 7,981,929 in view of methods for introducing phenyl boronate groups, benzoxaborole groups, and borono-pyridyl groups as described herein and as are known in the art and in view of synthetic methods that are well known in the art. Compounds herein having a boronate group protected with an N-derivatized iminodiacetic acid (see formula above) can be prepared from starting materials and reagents that are commercially available or readily prepared by known methods, or routine adaptations thereof, by one of ordinary skill in the art, in view of descriptions herein and in U.S. Pat. Nos. 8,318,983, 8,557,980 and 8,722,916 as well as in references 14-16

More generally compounds, prodrugs, salts and esters of this invention which have phenyl boronate or benzoxaborole groups, can be prepared from starting materials and reagents that are commercially available or readily prepared by known methods, by one of ordinary skill in the art in view of methods described in one or more of U.S. patents:

U.S. Pat. Nos. 5,196,438; 5,413,999; 5,484,801; 5,484,926; 5,585,397; 5,585,397; 5,744,481; 5,786,483; 5,843,946; 5,849,911; 5,852,195; 5,852,195; 5,856,353; 5,914,332; 5,968,942; 6,060,476; 6,169,181; 6,248,775; 6,248,775; 6,372,778; 6,417,387; 6,436,989; 6,472,407; 6,500,832; 6,646,010; 6,924,286; 7,608,632; 7,981,929; 8,318, 983, 8,557,980, 8,722,916 or U.S. published application 20100093811 in view of methods for introducing phenyl boronates, benzoxaboroles, borono-pyridyl groups as described herein and as are known in the art and in view of synthetic methods that are well known in the art and in addition in view of known methods for protecting boronate groups, particularly with N-substituted iminodiacetate.

The number of carbons in a given group is designated herein using the terminology CX—CY, where X and Y are integers representing the lowest number and the highest number of carbons in the references group, as in C1-C4 alkyl which refers to an alkyl group having 1-4 carbon atoms. In a number of the formulas of this invention reference is made to the definition of variables in a given patent or patents or published U.S. patent application. In these instances, the variable definition from the patent document listed applies.

In other cases, formula variables are specifically defined in the present specification and the definitions of such variables is defined herein or employs the broadest definition in the art of a given chemical moiety or group.

The terms alkyl or alkyl group, alone or in combination, refer to a monoradical of a straight chain or branched saturated hydrocarbon. Alkyl groups include straight-chain and branched alkyl groups. Unless otherwise indicated alkyl groups have 1-12 carbon atoms (C1-C12 alkyl groups) and preferred are those that contain 1-6 carbon atoms (C1-C6 alkyl groups) and more preferred are those that contain 1-4 carbon atoms (C1-C4 alkyl groups) and those that contain 1-3 carbon atoms (C1-C3 alkyl groups). Unless otherwise indicated alkyl groups are optionally substituted with one or more non-hydrogen substituents as described herein. However any alkyl group designated herein can be unsubstituted. The designation of an alkyl group having a range of carbon atoms includes all isomers having that number of carbon atoms. Exemplary alkyl groups include methyl, ethyl, n-propyl, iso-propyl, n-butyl, s-butyl, t-butyl, n-pentyl, branched pentyl, n-hexyl, branched hexyl, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl.

The term alkoxy refers to an —O-alkyl group, where alkyl is as defined above. Alkoxy groups include among others methoxy, ethoxy, n-propoxy, isopropoxy, n-butoxy, isobutoxy, sec-butoxy, and tert butoxy. Alkoxy groups are optionally substituted.

The term cycloalkyl, alone or in combination, means an alkyl radical which contains at least one carbon ring. These groups may be monocyclic, bicyclic or tricyclic. Unless otherwise indicated a cycloalkyl contains from 3 to 12 carbons and the carbon ring contains 3-10 carbons and more preferably 3-7 carbon atoms. Examples of such cycloalkyl groups include cyclopropyl, cyclobutyl, cyclopentyl, and cyclohexyl. Cycloalkyl groups are optionally substituted.

The term alkenyl, alone or in combination, refers to a straight-chain or branched-chain mono-, di- or poly-unsaturated aliphatic hydrocarbon radical containing the specified number of carbon atoms, or where no number is specified, preferably from 2-10 carbon atoms, more preferably, from 2-6 carbon atoms and also from 2-4 carbon atoms. Unless specifically stated, all isomers of the given number of carbon atoms are included. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z hexadienyl. Alkenyl groups are optionally substituted.

The term alkenoxy refers to an —O-alkenyl group, where alkenyl is defined above. Alkenoxy groups are optionally substituted.

The term cycloalkenyl means an alkyl radical which contains at least one carbon ring and at least one double bond. These groups may be monocyclic, bicyclic or tricyclic. Unless otherwise indicated a cycloalkyl contains from 3 to 12 carbons and the carbon ring contains 3-10 carbons and more preferably 3-7 carbon atoms. Examples of such cycloalkenyl groups include cyclopentenyl, cyclohexenyl, cycloheptenyl and cyclooctenyl. Cycloalkenyl groups are optionally substituted.

An acyl group is an R'—CO group where R' in general is a hydrogen, an alkyl, alkenyl or alkynyl, aryl or heteroaryl group as described above. In specific embodiments, acyl groups have 1-20, 1-12, or 1-6 carbon atoms and optionally 1-3 heteroatoms, optionally one double bond or one triple bond. In specific embodiments, R is a C1-C6 alkyl, alkenyl group. cyclic configuration or a combination thereof, attached to the parent structure through a carbonyl functionality. Examples include acetyl, benzoyl, propionyl, isobutyryl, or oxalyl. The R' group of acyl groups are optionally substituted as described herein. When R' is hydrogen, the group is a formyl group. An acetyl group is a $CH_3$—CO— group. Another exemplary acyl group is a benzyloxy group.

The term "aryl," alone or in combination, refers to a carbocyclic aromatic radical (such as phenyl or naphthyl) containing the specified number of carbon atoms. If not specified aryl groups contain from 6-15 carbon atoms, preferably from 6-10 carbon atoms, and particularly contain from 6-10 ring carbons. Aryl groups unless otherwise stated are optionally substituted among others with one or more substituents selected from alkyl, alkoxy, nitro, halogen, (for example chloro), amino, carboxylate and hydroxy. In specific embodiments, aryl group are optionally substituted phenyl groups. Aryl groups may contain two rings that re fused (naphthyl) or two rings which are bonded together by a C—C bond (biphenyl). Examples of aryl groups include, among others, phenyl, p-tolyl, 4-hydroxyphenyl, 1-naphthyl, 2-naphthyl, indenyl, indanyl, azulenyl, fluorenyl, and anthracenyl.

The term heterocyclyl or heterocyclic refers to monoradical having a ring of a specified number of ring atoms, where the ring atoms include one or more heteroatoms (N, O, S) or heteroatom groups (e.g., —NH—, or —N(alkyl)-. More specifically, the term includes groups having a stable 3-7 membered monocyclic heterocyclic ring or a 8-11 membered bicyclic heterocyclic ring. The ring can be saturated, or partially unsaturated, and which may be optionally benzofused if monocyclic and which is optionally substituted unless otherwise stated on one or more carbon atoms by halogen, alkyl, alkoxy, oxo (═O) or on a secondary nitrogen atom by alkyl, phenyl or phenylalkyl. A number of heterocyclic groups are exemplified in the specification. Each heterocycle consists of one or more carbon atoms and from one to four heteroatoms selected from the group consisting of nitrogen, oxygen and sulfur and oxidized forms thereof. Heterocycles include 5-7 membered monocyclic heterocycles and 8-10 membered bicyclic heterocycles.

The term "heteroaryl" refers to a group having at least one aromatic ring wherein the ring contains at least one heteroatom or heteroatom group, as defined above. More specifically, the term refers to stable 5-6 membered monocyclic or 8-11 membered bicyclic aromatic hetero cycles where heterocycles is as defined above. Non-limiting examples of such groups include imidazolyl, quinolyl, isoquinolyl, indolyl, indazolyl, pyridazyl, pyridyl, pyrrolyl, pyrazolyl, pyrazinyl, quinoxolyl, pyranyl, pyrimidinyl, furyl, thienyl, triaZolyl, thiaZolyl, carbolinyl, tetrazolyl, benzofuranyl, thiamorpholinyl sulfone, oxazolyl, benzoxazolyl, benzimidazolyl, benZthiaZolyl, oxopiperidinyl, oxoppyrrolidinyl, oxoazepinyl, azepinyl, isoxazolyl, isothiazolyl, furazanyl, thiazolyl, thiadiazolyl, and oxathiolyl.

A carbocyclyl group is a group having one or more saturated or unsaturated carbon rings. Carbocyclyl groups, for example, contain one or two double bonds. One or more carbons in a carbocyclic ring can be —CO— groups. Carbocyclyl groups include those having 3-12 carbon atoms, and optionally replacing 1 or 2 carbon atoms with a —CO— group and optionally having 1, 2 or 3 double bonds. Carbocyclyl groups include those having 5-6 ring carbons. Carbocyclyl groups can contain one or more rings each of which is saturated or unsaturated. Carbocyclyl groups include bicyclic and tricyclic groups. Preferred carbocyclic groups have a single 5- or 6-member ring. Carbocyclyl groups are optionally substituted as described herein. Specifically, carbocyclic groups can be substituted with one or more alkyl groups. Carbocyclyl groups include among others cycloalkyl and cycloalkenyl groups.

Groups herein are optionally substituted most generally alky, alkenyl, and aryl, heteroaryl, and heterocyclyl groups can be substituted, for example, with one or more oxo group, thioxo group, halogen, nitro, cyano, cyanate, azido, thiocyano, isocyano, isothiocyano, sulfhydryl, hydroxyl, alkyl, alkoxy, alkenyl, alkenyloxy, alkynyl, alkynyloxy, aryl, aryloxy, heteroaryl, heteroaryloxy, carbocyclyl, carbocyclyloxy, heterocyclyl, heterocyclyloxy, alkylthio, alkenylthio, alkynylthio, arylthio, thioheteroaryl, thioheteroaryl, thiocarbocyclyl, thioheterocyclyl, —COR, —COH, —OCOR, —OCOH, —CO—OR, —CO—OH, —CO—O—CO—R, —CON(R)$_2$, —CONHR, —CONH$_2$, —NR—COR, —NH-COR, —NHR, —N(R)$_2$, —O—SO$_2$—R, —SO$_2$—R, —SO$_2$—NHR, —SO$_2$—N(R)$_2$, —NR—SO$_2$—R, —NH—SO$_2$—R, —NRCO—N(R)$_2$, —NH—CO—NHR, —O—PO(OR)$_2$, —O—PO(OR)(N(R)$_2$), —O—PO(N(R)$_2$)$_2$, where each R independently is an organic group and more specifically is an alkyl, cyclolkyl, alkenyl, cycloalkenyl, aryl, heteroaryl, or heterocyclyl group or two R within the same substitutent can together form a carbocyclic (containing only carbon ring members) or heterocyclic ring having 3 to 10 ring atoms. Organic groups of non-hydrogen substituents are in turn optionally substituted with one or more halogens, nitro, cyano, isocyano, isothiocyano, hydroxyl, sulfhydryl, haloalkyl, hydroxyalkyl, amino, alkylamino, dialkylamino, arylalkyl, unsubstituted alkyl, unsubstituted alkenyl, unsubstituted alkynyl alkylalkenyl, alkylalkynyl, haloaryl, hydroxylaryl, alkylaryl, unsubstituted aryl, unsubstituted carbocylic, halo-substituted carbocyclic, hydroxyl-substituted carbocyclic, alkyl-substituted carbocyclic, unsubstituted heterocyclic, unsubstituted heteroaryl, alkyl-substituted heteroaryl, or alkylsubstitued heterocyclic. In specific embodiments, R groups of substituents are independently selected from alkyl groups, haloalkyl groups, phenyl groups, benzyl groups and halosubstituted phenyl and benzyl groups. In specific embodiments, non-hydrogen substituents have 1-10 carbon atoms, 1-7 carbon atoms, 1-5 carbon atoms or 1-3 carbon atoms. In specific embodiments, non-hydrogen substituents have 1-10 heteroatoms, 1-6 heteroatoms, 1-4 heteroatoms, or 1, 2, or 3 heteroatoms. Heteroatoms preferably are O, N or S.

In specific embodiments, optional substitution is substitution with 1, 2, 3, 4 or 5 non-hydrogen substituents. In specific embodiments, optional substitution is substitution with 1 or 2 nonhydrogen substituents. In specific embodiments, optional substitution is substitution with 1 nonhydrogen substituents. In specific embodiments, optional substitution is substitution by one or more halogen, hydroxy group, cyano group, oxo group, thioxo group, unsubstituted C1-C6 alkyl group or unsubstituted aryl group. The term oxo group refers to substitution of a carbon atom with a =O[—CO-(carbonyl)] group.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Compounds of the invention may contain chemical groups (acidic or basic groups) that can be in the form of salts. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The invention provides methods for treating or preventing HIV infection and the symptoms and disorders associated therewith. The invention provides pharmaceutical compositions comprising a pharmaceutically effective amount of one or more compounds and/or salts of the invention and a pharmaceutically acceptable carrier or excipient. The compounds and salts thereof of the invention can be used to prepare medicaments for the treatment and prevention of HIV infection and the symptoms and disorders associated therewith.

The term "pharmaceutically effective amount" refers to an amount effective in treating a virus infection, as symptom or complication thereof, for example an HIV infection, in a patient (human or other mammal) either by administration of a single compound or salt thereof or in combination with other agents. The pharmaceutically effective amount of a given compound when administered as the only active ingredient may differ from its pharmaceutically effective amount when administered with other active ingredients. It will be appreciated that the pharmaceutically effective amount of a compound may differ from that of a salt of the same compound. Treating includes the alleviation of symptoms of a particular disorder in a patient or a measurable improvement of a parameter associated with a particular disorder. Treating includes treatment to prevent viral infection and to delay the progress of an infection. The term "prophylactically effective amount" refers to an amount of a compound or salt of the invention effective in preventing a virus infection, for example an HIV infection, in a patient. The compounds of the present invention are useful in the treatment of individuals infected by HIV and for the prophylaxis of these individuals. It will be appreciated in the art, that individuals at risk for HIV infection can be treated employing one or more of the compounds or salts of the invention to prevent or delay infection. The compounds and salts of present invention are useful in the treatment of conditions associated with HIV infection, including AIDS, AIDS-related complex (ARC), progressive generalized lymphadenopathy (POL), as well as chronic CNS diseases caused by retroviruses, such as, for example HIV mediated dementia and multiple sclerosis. In general, the compounds and salts of the invention can be employed for treatment as is known in the art for other HIV protease inhibitors as described in one or more of the patent documents cited herein and as is known in the art.

As used herein, the term "patient" refers to a mammal, including a human.

Compounds of the invention may contain chemical groups (acidic or basic groups) that can be in the form of salts. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-Dglucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Salts of the invention include "pharmaceutically acceptable salts" which refers to those salts which retain the biological effectiveness and properties of the free bases or free acids, and which are not biologically or otherwise undesirable. Pharmaceutically acceptable salts comprise pharmaceutically-acceptable anions and/or cations.

Compounds of the invention can be administered in the form of pharmaceutically acceptable salts which include the following non-limiting examples: alkali metal salts, such as those of lithium, potassium and sodium; alkali earth metal salts, such as those of barium, calcium and magnesium; transition metal salts, such as those of zinc; and other metal salts, such as those of aluminum, sodium hydrogen phosphate and disodium phosphate; salts of nitrates, borates, methanesulfonates, benzene sulfonates, toluenesulfonates, salts of mineral acids, such as those of hydrochlorides, hydrobromides, hydroiodides and sulfates; salts of organic acids, such as those of acetates, trifuoroacetates, maleates, oxalates, lactates, malates, tartrates, citrates, benzoates, salicylates, ascorbates, succinates, butyrates, valerates and fumarates, amine salts, such as those of N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane.

Pharmaceutically acceptable salts can be derived from inorganic or organic acids or can be derived from inorganic or organic bases as is known in the art.

Basic amino acids useful for salt formation include arginine, lysine and ornithine. Acidic amino acids useful for slat formation include aspartic acid and glutamic acid.

Compound of the invention can be administered in the form of pharmaceutically acceptable esters which include, among others, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids and boronic acids.

Those of ordinary skill in the art will appreciate that many organic compounds, including salts, can form complexes with solvents in which they are reacted or from which they are precipitated or crystallized. These complexes are known as "solvates". For example, a complex with water is known as a "hydrate". Solvates, and more particularly hydrates, of the boronated compounds of the invention are within the scope of the invention. Pharmaceutically acceptable solvates and hydrates are complexes of a compound of the invention with one or more solvent or water molecules, or 1 to about 100, or 1 to about 10, or one to about 2, 3 or 4, solvent or water molecules.

Compounds and salts of the invention in the form of pharmaceutical compositions or dosage forms the invention can be administered by any known route that is appropriate for the patient being treated and for the treatment or prophylaxis that is desired. Specifically administration can be orally or non-orally in the form of, for example, granules, powders, tablets, capsules, syrup, suppositories, injections, emulsions, elixir, suspensions or solutions, by mixing these effective components, individually or simultaneously, with pharmaceutically acceptable carriers, excipients, binders, diluents or the like.

A solid formulation for oral administration can comprise one or more of the compounds or salts of the invention alone or in appropriate combination with other active ingredients. Solid formulations can be in the form of powders, granules, tablets, pills and capsules. In these cases, the instant compounds can be mixed with at least one additive, for example, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. These formulations can contain, as in conventional cases, further additives, for example, an inactive diluent, a lubricant such as magnesium stearate, a preservative such as paraben or sorbic acid, an anti-oxidant such as ascorbic acid, tocopherol or cysteine, a disintegrator, a binder, a thickening agent, a buffer, a sweetener, flavoring agent and/or a perfuming agent. Tablets and pills can also be prepared with enteric coating. Standard methods of formulation can be applied to preparation of formulations of the compounds and salts of the invention.

Non-oral administration includes subcutaneous injection, intravenous injection, intramuscular injections, intraperitoneal injection or instillation. Injectable preparations, for example, sterile injectable aqueous suspensions or oil suspensions can be prepared by known methods.

The instant pharmaceutical compositions may be formulated as known in the art for nasal aerosol or inhalation and may be prepared as solutions in saline, and benzyl alcohol or other suitable preservatives, absorption promoters, fluorocarbons, or solubilizing or dispersing agents.

Rectal suppositories can be prepared by mixing the drug with a suitable vehicle, for example, cocoa butter and polyethylene glycol, which is in the solid state at ordinary temperatures, in the liquid state at temperatures in intestinal tubes and melts to release the drug.

Examples of liquid preparations for oral administration include pharmaceutically acceptable emulsions, syrups, elixirs, suspensions and solutions, which may contain an inactive diluent, for example, pharmaceutically acceptable water.

The pharmaceutical composition can be formulated for topical administration with a suitable ointment containing one or more of the compounds or salts of the invention suspended or dissolved in a carrier, which include mineral oil, liquid petroleum, white petroleum, propylene glycol, polyoxyethylene polyoxypropylene compound, emulsifying wax and pharmaceutically acceptable water. In addition, topical formulations can be formulated with a lotion or cream containing the active compound suspended or dissolved in a carrier. Suitable carriers include mineral oil, sorbitan monostearate, polysorbate 60, cetyl esters wax, cetearyl alcohol, 2-octyldodecanol, benzyl alcohol and pharmaceutically acceptable water.

As is understood in the art, dosages of the instant compounds are dependent on age, body weight, general health conditions, sex, diet, dose interval, administration routes, excretion rate, combinations of drugs and conditions of the diseases treated. While taking these and other necessary factors into consideration, generally, dosage levels of between about 10 pg per day to about 5000 mg per day, preferably between about 100 mg per day to about 1000 mg per day of the compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier or excipient materials to produce a single dosage form will vary depending upon the patient/individual treated and the particular mode of administration. A typical preparation will contain from about 5% to about 95% active compound (W/W). Preferably, such preparations contain from about 20% to about 80% active compound.

While these dosage ranges can be adjusted by a necessary unit base for dividing a daily dose, as described above, such doses are decided depending on the diseases to be treated, conditions of such diseases, the age, body weight, general health conditions, sex, diet of the patient then treated, dose intervals, administration routes, excretion rate, and combinations of drugs. While taking these and other necessary factors into consideration, for example, a typical preparation will contain from about 0.05% to about 95% active compound (W/W). Preferably, such preparations contain from about 10% to about 80% active compound. The desired unit dose of the composition of this invention is administered once or multiple times daily.

A preferred embodiment of the instant invention are compositions and formulations comprising one or more of the instant compounds in combination with one or more other HIV protease inhibitors, reverse transcriptase inhibitors, or non-nucleoside reverse transcriptase inhibitors.

The compounds of this invention may be administered to an uninfected or HIV-infected patient either as a single agent or in combination therapy with other anti-viral agents which interfere with the replication cycle of HIV in order to increase the therapeutic effect of these compounds.

The invention relates to compositions comprising one or more compound of the present invention, and another antiretroviral compound as a combined preparation for simultaneous, separate or sequential use in treatment of retroviral infections, in particular, in the treatment of infections.

To treat HIV infection and disease associated with HIV infections, such as Acquired Immunodeficiency Syndrome (AIDS) or AIDS Related Complex (ARC), the compounds of this invention may be co-administered in combination with, binding inhibitors, fusion inhibitors; coreceptor binding inhibitors, RT inhibitors, nucleoside RTIs, nucleotide RTIs, NNRTIs, RNAse H inhibitors, TAT inhibitors, integrase inhibitors, protease inhibitors, such as, for example, amprenavir and fosamprenavir, ritonavir, nelfnavir, saquinavir, indinavir, lopinavir, palinavir, atazanavir, tipranavir, and/or glycosylation inhibitors.

The compounds of the present invention may also be administered in combination with immunomodulators, antibiotics, cytokines, modulators of cytokines, chemokines or the receptors thereof or hormones to treat, ameliorate, or eliminate HIV infection and its symptoms. Such combination therapy in different formulations may be administered simultaneously, separately or sequentially. Alternatively, such combination may be administered as a single formulation, where the active ingredients are released from the formulation simultaneously or separately.

The compounds and salts of the present invention may be administered in combination, for example, with ritonavir. As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. A number of prodrugs of HIV inhibitors are known in the art and the present description provides a description of a number of such prodrugs.

As used herein, prodrugs include phosphonates and include compounds in which the boronate groups of the boronated aryl or boronated heteroaryl group is protected with a protecting group such as that of an N-substituted iminodiacetic acid and more specifically of with the protecting group N-methyliminodiacetic acid.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately.

When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein. Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1

Materials and Methods

Commercial reagents were used without further purification. (2S,3S)-1,2-epoxy-3-(boc-amino)-4-phenylbutane was from Sigma-Aldrich (St. Louis, Mo.). All glassware was oven- or flame-dried, and reactions were performed under $N_2(g)$ unless stated otherwise. Dichloromethane was dried over a column of alumina. Triethylamine was dried over a column of alumina and purified further by passage through an isocyanate scrubbing column. Flash chromatography was performed with columns of 40-63 Å silica, 230-400 mesh (Silicycle, Québec City, Canada). Thin-layer chromatography (TLC) was performed on plates of EMD 250-μm silica 60-$F_{254}$. The term "concentrated under reduced pressure" refers to the removal of solvents and other volatile materials using a rotary evaporator at water aspirator pressure (<20 torr) while maintaining the water-bath temperature below 40° C. Residual solvent was removed from samples at high vacuum (<0.1 torr). The term "high vacuum" refers to vacuum achieved by a mechanical belt-drive oil pump. NMR spectra were acquired at ambient temperature with a Bruker DMX-400 Avance spectrometer at the National Magnetic Resonance Facility at Madison (NMRFAM) and referenced to TMS or residual protic solvent. Electrospray ionization (ESI) mass spectrometry was performed with a Micromass LCT at the Mass Spectrometry Facility in the Department of Chemistry at the University of Wisconsin-Madison.

Example 2

Synthesis of B-Amprenavir (6)

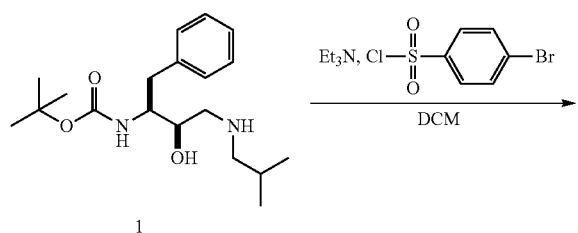

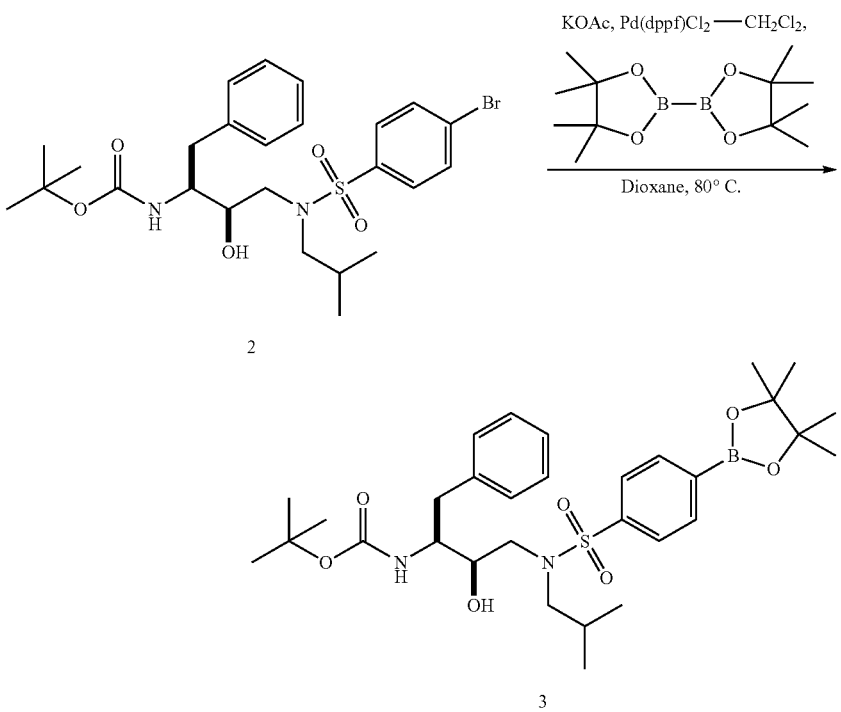

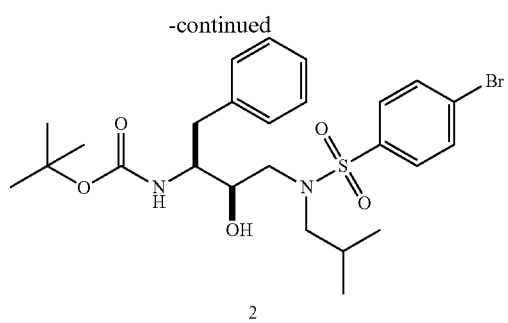

A. A round-bottom flask containing 1 (synthesized as described previously, [1]1.791 g, 5.323 mmol) was dissolved in 60 mL of dichloromethane, and the resulting solution was cooled to 0° C. Triethylamine (1.2 mL, 8.6 mmol) and 4-bromobenzenesulfonyl chloride (1.362 g, 5.330 mmol) were then added, and the reaction mixture was left to stir overnight under an atmosphere of dry $N_2(g)$. After 16 h, the reaction mixture was concentrated under reduced pressure, and the product was purified by column chromatography (silica, 30% v/v EtOAc in hexanes), resulting in 2 as a white solid (2.543 g, 86%).

$^1$H NMR (400 MHz, CDCl$_3$) δ=7.67-7.62 (m, 4H), 7.33-7.22 (m, 5H), 4.64 (d, J=8.4 Hz, 1H), 3.87-3.76 (m, 3H), 3.11 (d, J=6.1 Hz, 1H), 3.03-2.84 (m, 4H), 1.91-1.81 (m, 1H), 1.36 (s, 9H), 0.91 (d, J=6.6 Hz, 3H), 0.88 (d, J=6.6 Hz, 3H); $^{13}$C NMR (100 MHz, CDCl$_3$) δ=156.2, 137.8, 137.7, 132.5, 129.6, 128.9, 128.6, 127.9, 126.6, 79.9, 72.7, 58.4, 54.9, 53.4, 35.6, 28.4, 27.2, 20.2, 20.0; HRMS (ESI) calculated for [C$_{25}$H$_{35}$BrN$_2$O$_5$SNa]$^+$ (M+Na$^+$) requires m/z=577.1343. found 577.1364.

B. Compound 2 (0.262 g, 0.472 mmol), KOAc (0.139 g, 1.416 mmol), bis(pinacolato)diboron (0.708 g, 0.180 mmol), and Pd(dppf)Cl$_2$—CH$_2$Cl$_2$ (34.54 mg, 0.0472 mmol) were placed in a dry Schlenk tube. The reaction flask was then evacuated and backfilled with $N_2(g)$ five times. Freshly degassed 1,4-dioxane (5 mL) was then added, and the reaction mixture was heated to 80° C. and stirred for 24 h under a $N_2(g)$ atmosphere. After 24 h, the reaction mixture was vacuum-filtered through a pad of Celite and concentrated under reduced pressure, and the product was purified by column chromatography (silica, 30% v/v EtOAc in hexanes), giving 3 as a white solid (0.253 g, 89%).

$^1$H NMR (400 MHz, CDCl$_3$) δ=7.94 (d, J=8.2 Hz, 2H), 7.75 (d, J=8.2 Hz, 2H), 7.31-7.28 (m, 2H), 7.25-7.21 (m, 3H), 4.67 (d, J=8.6 Hz, 1H), 3.93-3.91 (m, 1H), 3.84-3.81 (m, 1H), 3.78-3.74 (m, 1H), 3.13-3.06 (m, 2H), 3.01-2.81 (m, 4H), 1.89-1.81 (m, 1H), 1.36 (s, 12H), 1.35 (s, 9H), 0.89 (d, J=6.6 Hz, 3H), 0.86 (d, J=6.6 Hz, 3H); $^{13}$C NMR (100 MHz, CDCl$_3$) δ=156.1, 140.6, 137.9, 135.5, 129.7, 128.6, 126.5, 126.4, 84.6, 79.8, 72.8, 58.6, 54.9, 53.7, 35.5, 29.8, 28.4, 27.2, 25.0, 20.2, 20.0; HRMS (ESI) calculated for [C$_{31}$H$_{47}$BN$_2$O$_7$SNa]$^+$ (M+Na$^+$) requires m/z=624.3126. found 624.3151.

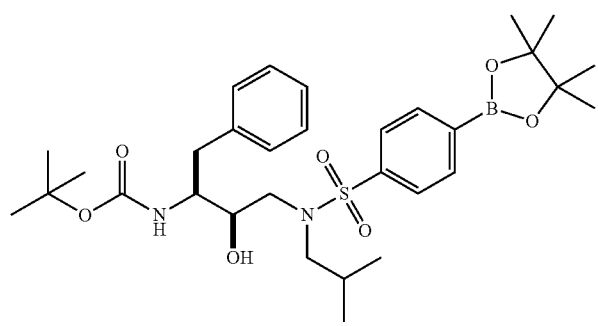 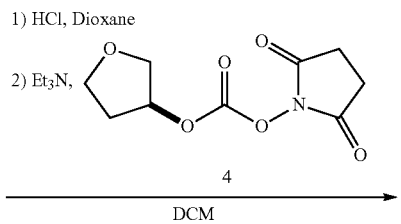

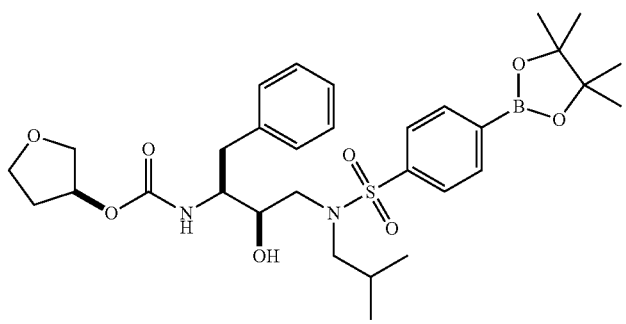

C. To a round-bottom flask containing compound 3 (0.150 g, 0.249 mmol) was added 10 mL of 4.0 M HCl in dioxane. After stirring for 4 h, the reaction mixture was purged with $N_2(g)$ to remove excess HCl(g). Once the evolution of HCl(g) ceased, the reaction mixture was concentrated under reduced pressure and dried overnight under high vacuum. The residue was then dissolved in 6 mL of DCM (dichloromethane) and placed under an inert atmosphere. Triethylamine (0.17 mL, 1.2 mmol) and 4 (synthesized as described previously, [1] 0.086 g, 0.374 mmol) were then added, and the reaction mixture was stirred at room temperature overnight. After reacting for 16 h, the reaction mixture was concentrated under reduced pressure, and the product was purified by column chromatography (silica, 5% v/v MeOH in), yielding 5 as a white solid (0.121 g, 79%).

$^1$H NMR (400 MHz, CDCl$_3$) δ=7.94 (d, J=7.8 Hz, 2H), 7.74 (d, J=7.8 Hz, 2H), 7.32-7.28 (m, 2H), 7.25-7.21 (m, 3H), 5.12 (s, 1H), 4.85 (d, J=8.7 Hz, 1H), 3.86-3.76 (m, 5H), 3.71-3.61 (m, 2H), 3.16-3.10 (m, 1H), 3.01-2.86 (m, 4H), 2.83-2.78 (m, 1H), 2.13-2.05 (m, 1H), 1.96-1.88 (m, 1H), 1.85-1.78 (m, 1H), 1.36 (s, 12H), 0.91 (d, J=6.6 Hz, 3H), 0.86 (d, J=6.6 Hz, 3H); $^{13}$C NMR (100 MHz, CDCl$_3$) δ=156.1, 140.4, 137.6, 135.5, 129.6, 128.7, 126.7, 126.4, 84.6, 76.7, 75.5, 73.4, 72.6, 67.0, 58.8, 55.2, 53.8, 35.5, 32.9, 27.3, 25.0, 20.2, 20.0; HRMS (ESI) calculated for $[C_{31}H_{49}BN_3O_8S]^+$ (M+NH$_4^+$) requires m/z=633.3365. found 633.3386.

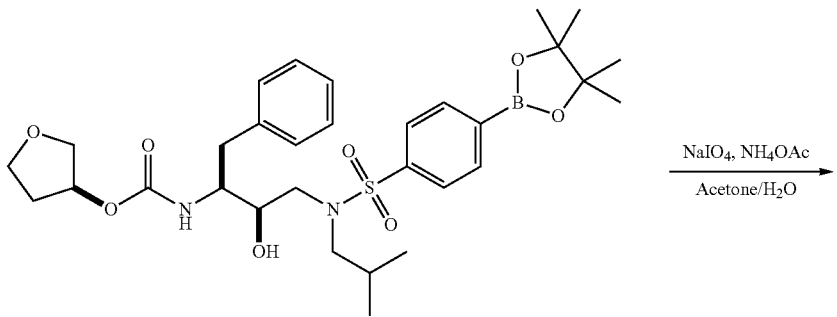

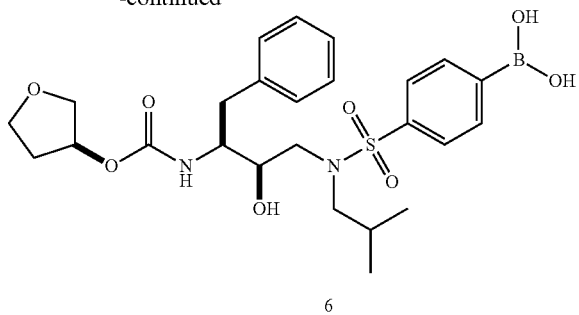

D. A round-bottom flask was charged with compound 5 (0.121 g, 0.196 mmol), which was then dissolved in acetone (10 mL) and H₂O (10 mL). The resulting solution was placed under an atmosphere of dry N$_2$(g), and sodium periodate (0.168 g, 0.784 mmol) and ammonium acetate (60.4 mg, 0.784 mmol) were added. After stirring for 12 h, the reaction mixture was concentrated under reduced pressure, and the product was purified by column chromatography (silica, 20% v/v MeOH in DCM), giving 6 as an off-white solid (75.42 mg, 72%). An analytically pure sample of 6 was obtained by reverse-phase HPLC using a preparatory C18 column and a linear gradient of 10-80% v/v acetonitrile (0.1% v/v TFA) in water (0.1% v/v TFA) over 45 min. 6 eluted at 36 min and, after lyophilization, was isolated as a white powder.

¹H NMR (400 MHz, Methanol-d₄) δ=7.80 (s, 4H), 7.27-7.22 (m, 3H), 7.19-7.15 (m, 1H), 7.00 (d, J=9.4 Hz, 1H), 5.01-4.98 (m, 1H), 3.85-3.68 (m, 5H), 3.47-3.43 (m, 2H), 3.15-3.08 (m, 2H), 2.98 (dd, J=15.1, 8.7 Hz, 1H), 2.90 (dd, J=13.7, 6.7 Hz, 1H), 2.55 (dd, J=13.8, 10.7 Hz, 1H), 2.13-1.94 (m, 3H), 0.94 (d, J=6.6 Hz, 3H), 0.86 (d, J=6.6 Hz, 3H); ¹³C NMR (100 MHz, Methanol-d₄) δ=158.2, 140.1, 135.2, 135.1, 130.5, 129.2, 127.4, 127.2, 76.4, 74.2, 74.1, 67.9, 58.7, 57.5, 53.8, 37.2, 33.6, 28.0, 20.5, 20.4; HRMS (ESI) calculated for [C₂₈H₄₂BN₂O₉S]⁻ (M+OMe⁻) requires m/z=592.2745. found 592.2721.

Example 3

B-Darunavir (9)

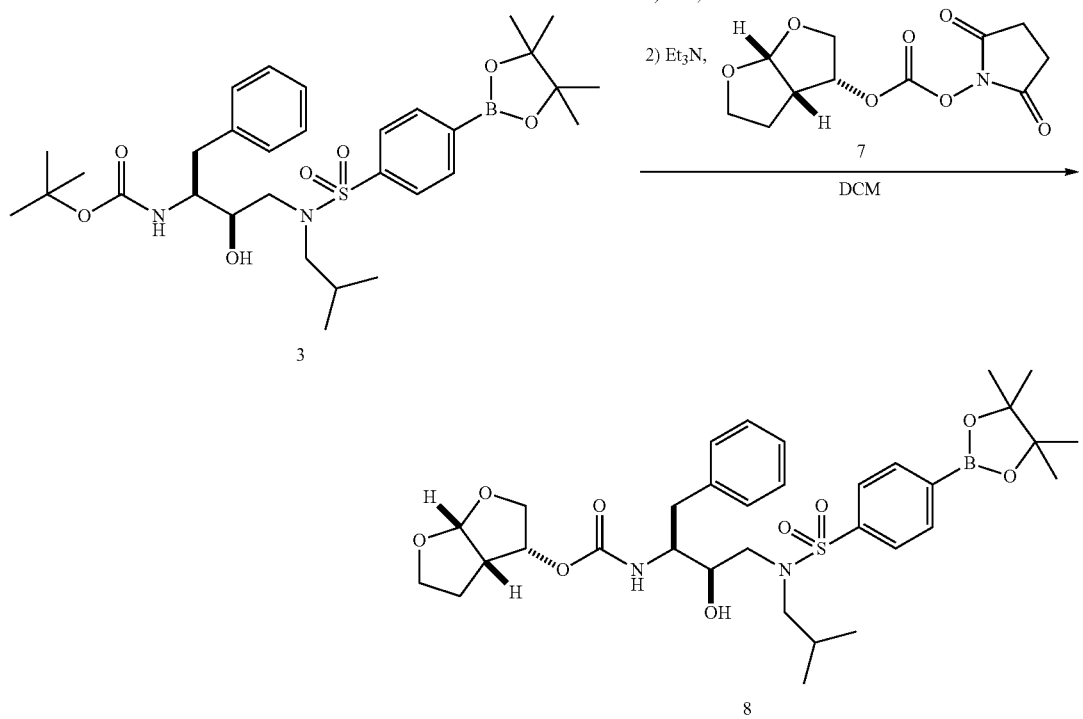

A. To a round-bottom flask containing compound 3 (0.327 g, 0.543 mmol) was added 15 mL of 4.0 M HCl in dioxane. After stirring for 4 h, the reaction mixture was purged with N$_2$(g) to remove excess HCl(g). Once the evolution of HCl(g) ceased, the reaction mixture was concentrated under reduced pressure and dried overnight under high vacuum. The residue was then dissolved in 10 mL of DCM and placed under an inert atmosphere. Triethylamine (0.38 mL, 2.7 mmol) and compound 7 (synthesized as described previously, [1] 0.147 g, 0.543 mmol) were then added, and the reaction mixture was stirred at room temperature overnight. After reacting for 16 h, the reaction was concentrated under reduced pressure, and the product was purified by column chromatography (silica, 5% v/v MeOH in DCM), yielding 8 as a white solid (0.293 g, 82%).

$^1$H NMR (400 MHz, CDCl$_3$) δ=7.94 (d, J=7.6 Hz, 2H), 7.75 (d, J=7.6 Hz, 2H), 7.30-7.26 (m, 2H), 7.22-7.20 (m, 3H), 5.65 (d, J=5.1 Hz, 1H), 5.04-4.99 (m, 1H), 4.95-4.92 (m, 1H), 3.96 (t, J=8.2 Hz, 1H), 3.88-3.83 (m, 3H), 3.72-3.68 (m, 2H), 3.63-3.59 (1H), 3.20-3.14 (m, 1H), 3.09-3.05 (m, 1H), 3.02-2.97 (m, 2H), 2.93-2.87 (m, 1H), 2.83-2.78 (m, 2H), 1.87-1.79 (m, 1H), 1.49-1.43 (m, 1H), 1.36 (s, 12H), 1.26-1.24 (m, 1H), 0.93 (d, J=6.5 Hz, 3H), 0.87 (d, J=6.5 Hz, 3H); $^{13}$C NMR (100 MHz, CDCl$_3$) δ=155.4, 140.1, 137.5, 135.4, 129.3, 128.6, 126.6, 126.3, 109.3, 84.5, 73.4, 72.7, 70.7, 69.6, 58.0, 55.1, 53.7, 45.3, 35.6, 27.3, 25.8, 24.9, 24.8, 20.1, 19.8; HRMS (ESI) calculated for [C$_{33}$H$_{51}$BN$_3$O$_9$S]$^+$ (M+NH$_4^+$) requires m/z=676.3431. found 676.3440.

2.99-2.84 (m, 3H), 2.53 (dd, J=14.3, 10.4 Hz, 1H), 2.07-1.99 (m, 1H), 1.54-1.46 (m, 1H), 1.37-1.32 (m, 1H), 0.94 (d, J=6.6 Hz, 3H), 0.88 (d, J=6.6 Hz, 3H); $^{13}$C NMR (100 MHz, Methanol-d$_4$) δ=157.7, 140.3, 135.2, 135.1, 130.5, 129.3, 127.4, 127.2, 110.8, 74.6, 74.5, 72.1, 70.6, 58.9, 57.4, 53.9, 46.9, 37.2, 28.0, 27.0, 20.5, 20.4; HRMS (ESI) calculated for [C$_{30}$H$_{44}$BN$_2$O$_{10}$S]$^-$ (M+OMe$^-$) requires m/z=635.2814. found 635.2821.

Example 4

Synthesis of Non-Boronated Analog Compound 11

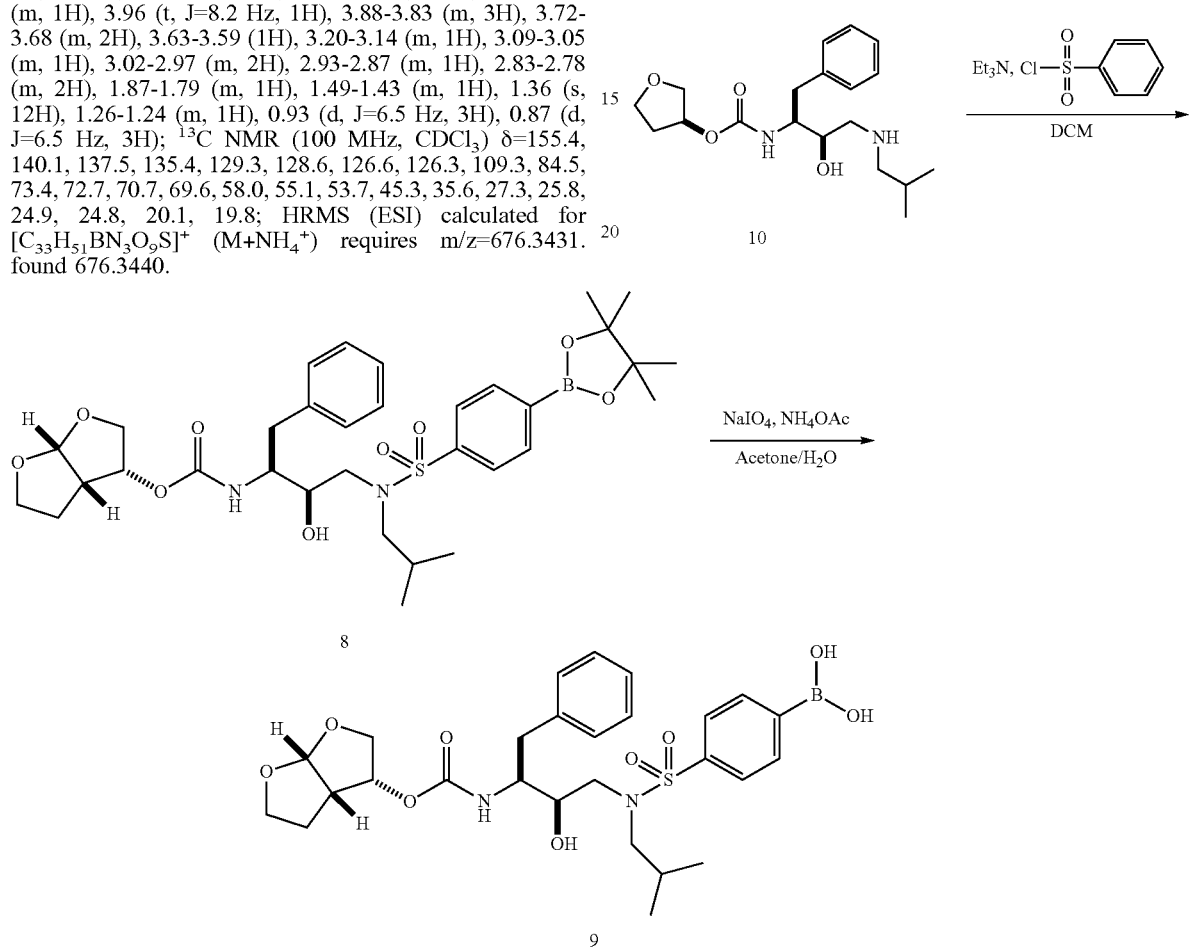

B. A round-bottom flask was charged with compound 8 (0.150 g, 0.228 mmol), which was then dissolved in acetone (10 mL) and H$_2$O (10 mL). The resulting solution was placed under an atmosphere of dry N$_2$(g), and sodium periodate (0.195 g, 0.911 mmol) and ammonium acetate (70.2 mg, 0.911 mmol) were added. After stirring for 12 h, the reaction mixture was concentrated under reduced pressure, and the product was purified by column chromatography (silica, 20% v/v MeOH in DCM), giving rise to 9 as an off-white solid (0.113 g, 86%). An analytically pure sample of 9 was obtained by reverse-phase HPLC using a preparatory C18 column and a linear gradient of 10-80% v/v acetonitrile (0.1% v/v TFA) in water (0.1% v/v TFA) over 45 min. Compound 9 eluted at 38 min and, after lyophilization, was isolated as a white powder.

$^1$H NMR (400 MHz, Methanol-d$_4$) δ=7.81 (s, 4H), 7.26-7.21 (m, 4H), 7.20-7.15 (m, 1H), 5.59 (d, J=5.0 Hz, 1H), 4.93 (q, J=6.4 Hz, 1H), 3.93 (dd, J=9.9, 6.2 Hz, 1H), 3.84-3.65 (m, 5H), 3.46-3.43 (m, 1H), 3.21-3.10 (m, 2H), -continued

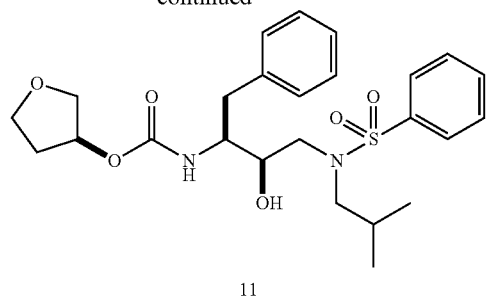

A round-bottom flask containing compound 10 (synthesized as described previously, [2]2.662 g, 7.595 mmol) was dissolved in 80 mL of dichloromethane, and the resulting solution was cooled to 0° C. Triethylamine (3.2 mL, 22.7 mmol) and benzenesulfonyl chloride (1.476 g, 8.355 mmol) were then added, and the reaction mixture was left to stir overnight under an atmosphere of dry $N_2(g)$. After 16 h, the reaction mixture was concentrated under reduced pressure, and the product was purified by column chromatography (silica, 30% v/v EtOAc in hexanes), resulting in 11 as a white solid (3.316 g, 89%).

$^1$H NMR (400 MHz, CDCl$_3$) δ=7.78 (d, J=7.6 Hz, 2H), 7.60 (t, J=7.6 Hz, 1H), 7.52 (t, J=7.6 Hz, 2H), 7.31-7.27 (m, 2H), 7.24-7.20 (m, 3H), 5.13-5.10 (m, 1H), 4.95 (d, J=8.6 Hz, 1H), 3.87-3.75 (m, 6H), 3.62 (d, J=10.5 Hz, 1H), 3.15 (dd, J=15.2, 8.3, 1H), 3.05-2.96 (m, 3H), 2.86 (td, J=14.3, 6.7 Hz, 2H), 2.12-2.05 (m, 1H), 1.95-1.89 (m, 1H), 1.85-1.80 (m, 1H), 0.91 (d, J=6.6 Hz, 3H), 0.87 (d, J=6.6 Hz, 3H); $^{13}$C NMR (100 MHz, CDCl$_3$) δ=156.2, 138.4, 137.6, 133.0, 129.6, 129.3, 128.7, 127.4, 126.7, 75.5, 73.3, 72.6, 67.0, 58.8, 55.2, 53.7, 35.5, 32.9, 27.3, 20.2, 20.0; HRMS (ESI) calculated for $[C_{25}H_{38}N_3O_6S]^+$ $(M+NH_4^+)$ requires m/z=508.2476. found 508.2471.

Example 5

Synthesis of a Prodrug of Compound 6

Phosphorylation is carried out essentially as in [9] under a $N_2$ atmosphere. Titanium tetrachloride (2 mol % with respect to compound 5) is added with stirring to THF (2 mL). Compound 5 (0.12 g, 0.2 mmol), triethylamine (0.3 mmol), THF (2 mL) diphenylchlorophosphate (0.3 mmol) and THF (2 mL) are then added to the stirred solution at room temperature. The reaction mixture is allowed to stir for 1 hour after which water (2 mL) is added. Solvents are removed under reduced pressure and the crude intermediate is treated as described [10] in 1 M LiOH/dioxane at room temperature and at 95° C. to remove a phenyl group. The product is treated with hydrogenolysis over Adams' catalyst in EtOH/H$_2$O (8:2 v:v) containing a trace of AcOH followed by heating at 95 C in 80% HOAc for 1 hr. The crude product is treated as in Example 2, step D to remove the boronate protecting group. The reaction mixture is concentrated under reduced pressure, and the product is purified by column chromatography (silica, 20% v/v MeOH in DCM), giving compound 12. Compound 12 is further purified by reverse-phase HPLC using a preparatory C18 column and a linear

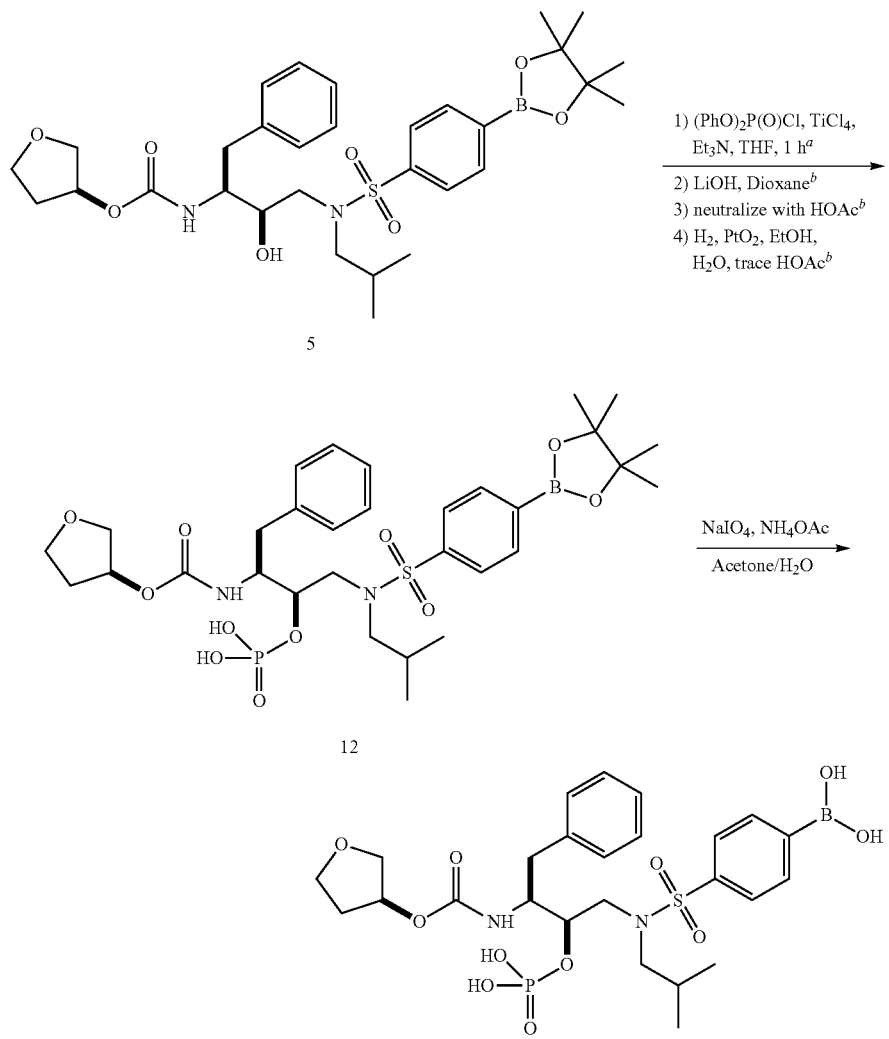

$^a$Jones, S., Selitsianos, D. *Org Lett.* 2002, 4, 3671-3673
$^b$Plourde, R.; d'Alarcao, M. *Tetrahedron Lett.* 1990. 31, 2693-2696 gradient of 10-80% v/v acetonitrile (0.1% v/v TFA) in water (0.1% v/v TFA), sample is collected and lyophilized.

It will be appreciated by one of ordinary skill that various means for phosphorylation of compounds 5 and/or 8 can be employed. For example, U.S. Pat. No. 6,436,989 provides methods for phosphorylation that can be employed to form prodrugs of the compounds of this invention.

Example 6

Benzoxaborole-Substituted Amprenavir (18)

Figure 7:
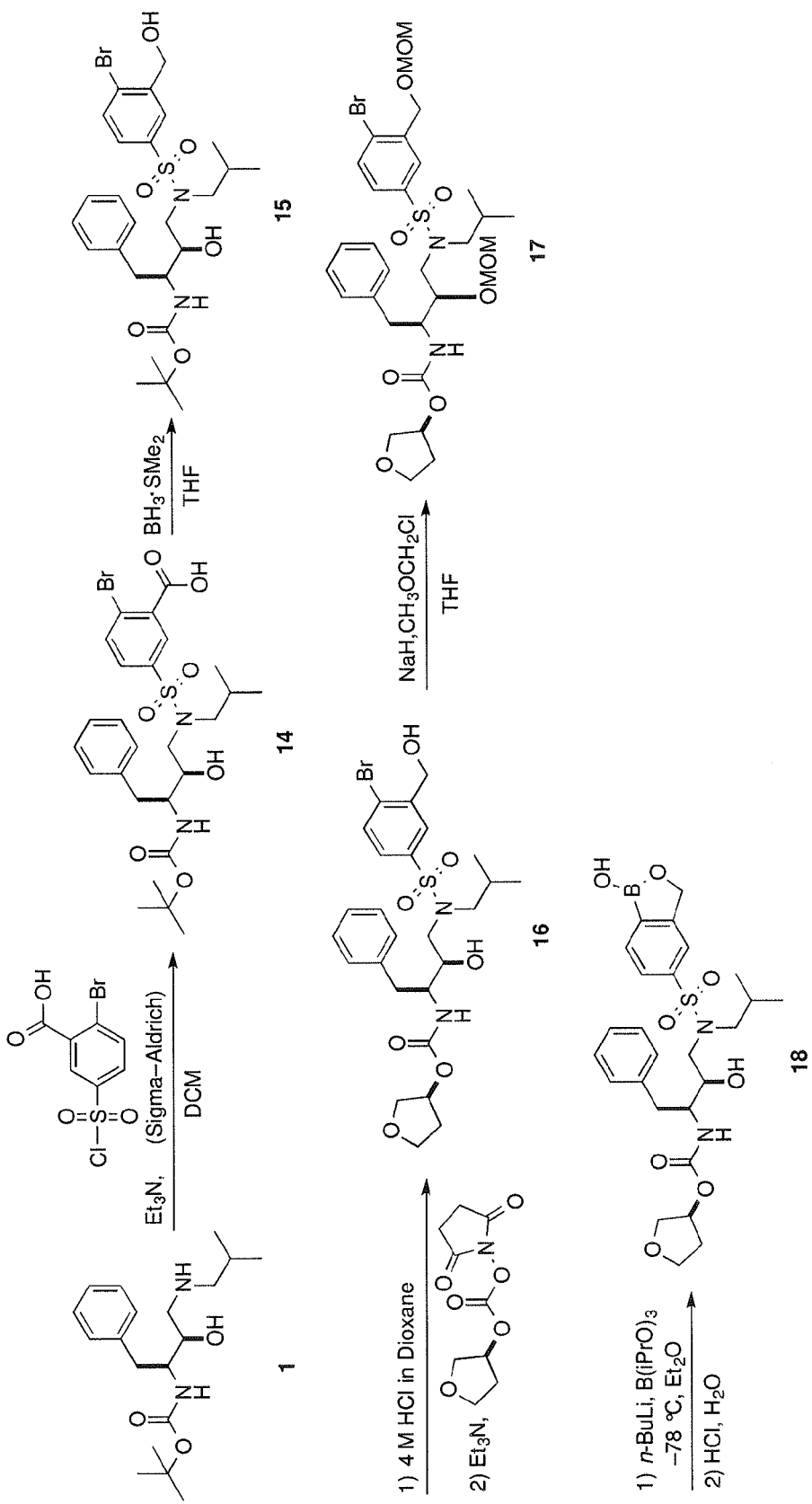
FIG. 7 is a chemical scheme for an exemplary method for the introduction of a benzoxaborole group into HIV protease inhibitors of this invention which are sulfonamide.

FIG. 7 provides a chemical scheme for an exemplary method for the introduction of a benzoxaborole group into HIV protease inhibitors of this invention which are sulfonamide. Benzoxaborole HIV protease inhibitors, prodrugs, esters and salts thereof of this invention can be prepared by one of ordinary skill in the art in view of this example and what is well-known in the art. The synthetic methods herein can be readily combined with those described in the patent documents incorporated by reference herein to prepare the compounds of the invention and prodrugs thereof, salts thereof and esters thereof.

Example 7

Boronated Tipranavir (22)

Figure 8:
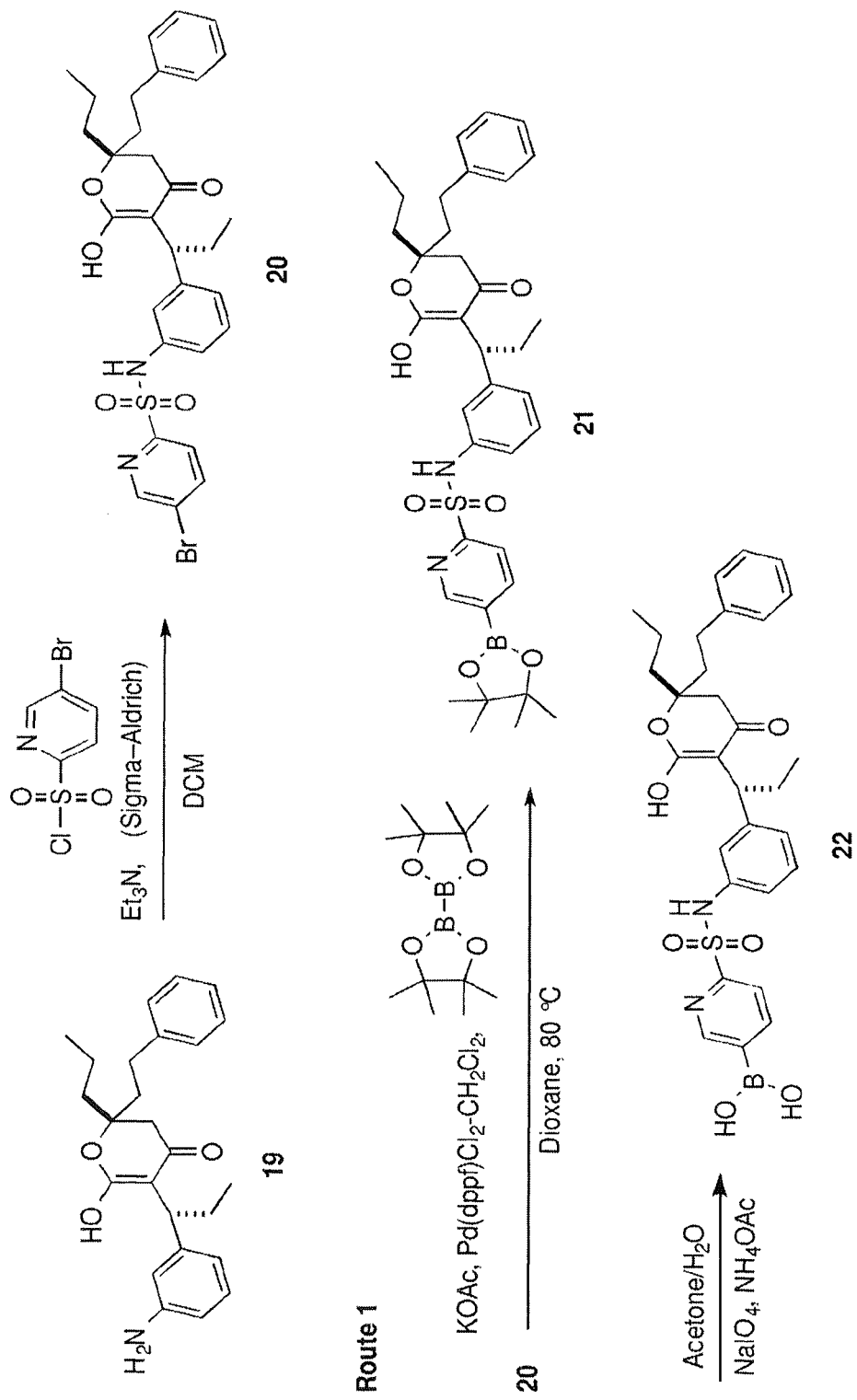
FIG. 8 is a first chemical scheme for an exemplary method for boronation of HIV protease inhibitors which are sulfonamide where a heteroaryl group is attached to the —SO$_2$— group, specifically where the heteroaryl group is a pyridyl.
Figure 9:
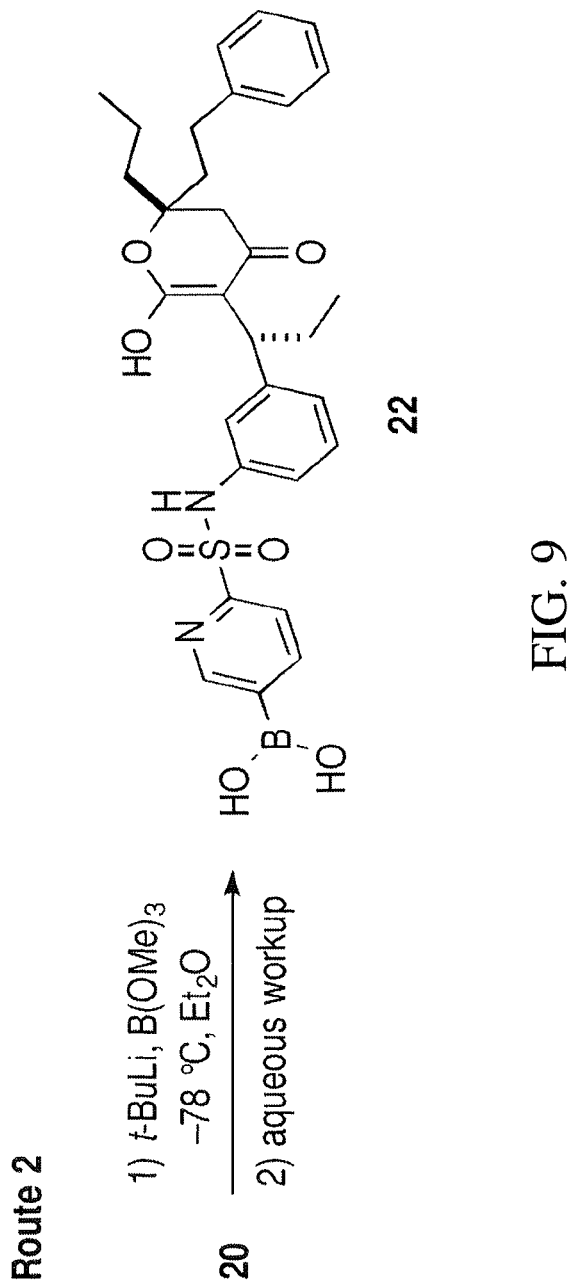
FIG. 9 is a second chemical scheme for an exemplary method for boronation of HIV protease inhibitors which are sulfonamide where a heteroaryl group is attached to the —SO₂— group, specifically where the heteroaryl group is a pyridyl.

FIGS. 8 and 9 provide exemplary methods for boronation of HIV protease inhibitors of this invention which are sulfonamide where a heteroaryl group is attached to the —SO$_2$— group, specifically where the heteroaryl group is a pyridyl. Tipranavir carries a pyridyl group. These methods introduce a —B(OH)$_2$ group on the pyridyl group. Formally, the resultant compound 22 carries a

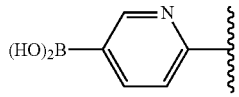

group, a 5-borono-pyrid-2-yl group.

HIV protease inhibitors, prodrugs, esters and salts thereof of this invention carrying a 5-borono-pyrid-2-yl group can be prepared by one of ordinary skill in the art in view of this example and what is well-known in the art. The synthetic methods herein can be readily combined with those described in the patent documents incorporated by reference herein to prepare compounds of the invention and prodrugs thereof, salts thereof and esters thereof wherein the sulfonamide group is:

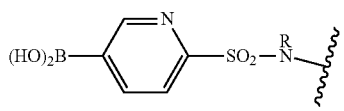

where R can take any definition of any of the sulfonamides of the formulas herein. In specific embodiments, R is C1-C4 alkyl, C1-C4 alkyl substituted with a C3-C7 cycloalkyl group or a phenyl group. In specific embodiments R is a butyl group or an isobutyl group.

Example 8

Preparation of an Expression Plasmid for HIV Protease

Double-stranded, linear DNA encoding HIV-1 protease with Q7K/L33I/L63I/C67A/C95A substitutions [3] and an N-terminal self-cleavable 8×His tag, and flanked by regions complementary to the T7 promoter T7 terminator regions in a pET32b vector from Novagen (Madison, Wis.) was obtained from IDT (Coralville, Iowa). Linear pET32b was prepared by PCR using primers that were the reverse-complement to the termini of the DNA sequence encoding HIV protease. Gene and plasmid fragments were joined covalently by using Gibson assembly [4] to generate the pET32b-HIV protease plasmid.

Example 9

Production and Purification of HIV Protease

A single colony of *Escherichia coli* strain BL21-Codon-Plus (DE3)-RIL from Stratagene (La Jolla, Calif.) was transformed with the pET32b-HIV protease plasmid and used to inoculate 1.00 L of Luria-Bertani medium containing ampicillin (200 μM) in a Fernbach flask. The flask was shaken at 37° C. When the culture reached saturation ($OD_{600}$=2.8-3.4), expression was induced by adding IPTG (isopropyl β-D-1-thiogalactopyranoside) to 2 mM, and the flask was shaken for an additional hour.

HIV protease was purified and folded as described previously, [5] with modifications. Cells (typically, 3 g per liter of culture) were pelleted, resuspended in 20 mM Tris-HCl buffer, pH 7.4, containing EDTA (1 mM) with a Potter-Elvehjem homogenizer, and lysed by a single pass through a cell disruptor from Constant Systems (Kennesaw, Ga.) at 18 kPSI. Inclusion bodies were isolated by centrifugation at 20 g for 20 min. The inclusion bodies were washed with the resuspension buffer containing urea (1.0 M) and Triton X-100 (1% v/v), and again with resuspension buffer. The inclusion bodies were collected again by centrifugation, and lyophilized.

The lyophilized inclusion bodies were dissolved in aqueous acetic acid (50% v/v) at 5 mg/mL by sonication. Unfolded HIV protease was clarified by centrifugation and applied to a Superdex 75 gel-filtration column from General Electric (Fairfield, Conn.) that had been pre-equilibrated with aqueous acetic acid (50%). Unfolded HIV protease, which eluted as a major peak near the column-volume, was pooled and lyophilized. Unfolded HIV protease (0.1 mg/mL) was folded in 100 mM sodium acetate buffer, pH 5.5, containing ethylene glycol (5% v/v) and glycerol (10% v/v) at 4° C. The folded protease was clarified by centrifugation and concentrated in a stirred-cell concentrator with a 10-kDa molecular weight cutoff membrane from EMD Millipore (Darmstadt, Germany). The concentrated solution of HIV protease was applied again to a Superdex 75 gel-filtration column that had been pre-equilibrated with folding buffer. A new major peak observed at ~0.75 column-volumes was pooled and concentrated. The folding buffer was exchanged with 1 mM sodium acetate buffer, pH 5.0, containing NaCl (2 mM) using a PD-10 desalting column from General Electric. The solution of purified HIV protease was flash-frozen in liquid nitrogen and stored at −80° C.

Example 10

Assay of the Catalytic Activity of HIV Protease

A peptide of sequence R-E(Edans)-SGIFLETS-K(Dabcyl)-R was designed and synthesized by Biomatik (Cambridge, Ontario, Canada). This peptide was used as a fluorogenic substrate for HIV protease by monitoring the fluorescence of the Edans group (5-((2-aminoethyl)amino) naphthalene-1-sulfonic acid) upon substrate hydrolysis and separation from the quenching Dabcyl group (4-((4-(dimethylamino)phenyl)azo)benzoic acid, succinimidyl ester. [6] Substrate was dissolved at 1 mM by sonication in DMF containing TFA (0.1% v/v). Stock solutions of each putative HIV protease inhibitor were generated by dissolving the inhibitor in DMF to a concentration of 50 mM and diluting in DMF to ~100×stocks of the final assay concentrations. Assays were performed in 50 mM sodium acetate buffer, pH 5.0, containing NaCl (100 mM). Wells in a microtiter plate were charged initially with inhibitor (various concentrations) and substrate (final concentration: 10 μM). HIV protease was then added (final concentration: 50-150 μM). Reaction velocities in the assay solutions (total volume: 200 μL) were measured in quadruplicate at 7-9 inhibitor concentrations including no-inhibitor and no-enzyme controls. Multiple assays were conducted in parallel with an M1000 Pro plate reader from Tecan (Maennedorf, Switzerland) in flat-black coming non-binding 96-well plate by exciting at 340 nm and monitoring fluorescence at 490 nm at ~30-s intervals. Initial velocities were obtaining by a linear fit of the data at <10% substrate conversion after equilibration (~5 min) using the program Microsoft Excel from Microsoft (Redmond, Wash.). The concentration of HIV protease was determined by active-site titration using darunavir as a titrant. Michaelis-Menten and Morrison's $K_i$ analysis were determined with the program Prism 7 from GraphPad Software (San Diego, Calif.). Results of the assay are shown in FIG. 1 (graphs A and B, where the and values of $K_i$ are listed in Table 1.

TABLE 1

Values of $K_i$ for HIV-1 protease inhibitors. Values (±SE) were determined by non-linear regression analysis of wild-type HIV-1 protease inhibition data using Morrison's equation.

| Compound | Experimental (pM) | Literature (pM) |
|---|---|---|
| Amprenavir | 86 ± 7 | 100 [7] |
| Darunavir | 13 ± 2 | 14 [8] |
| B-Amprenavir (6) | 2.1 ± 0.3 | — |
| B-Darunavir (9) | 0.9 ± 0.3 | — |

Example 11

Inhibition of HIV Cytopathic Toxicity by B-Darunavir

Figure 3:
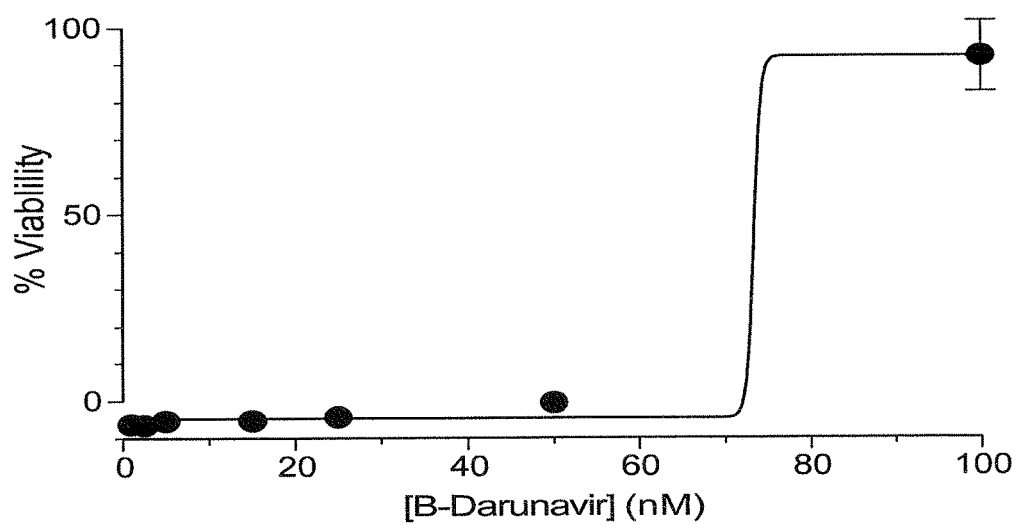
FIG. 3 is a graph illustrating the inhibition of HIV cytopathic toxicity by B-darunavir.
Figure 4A:
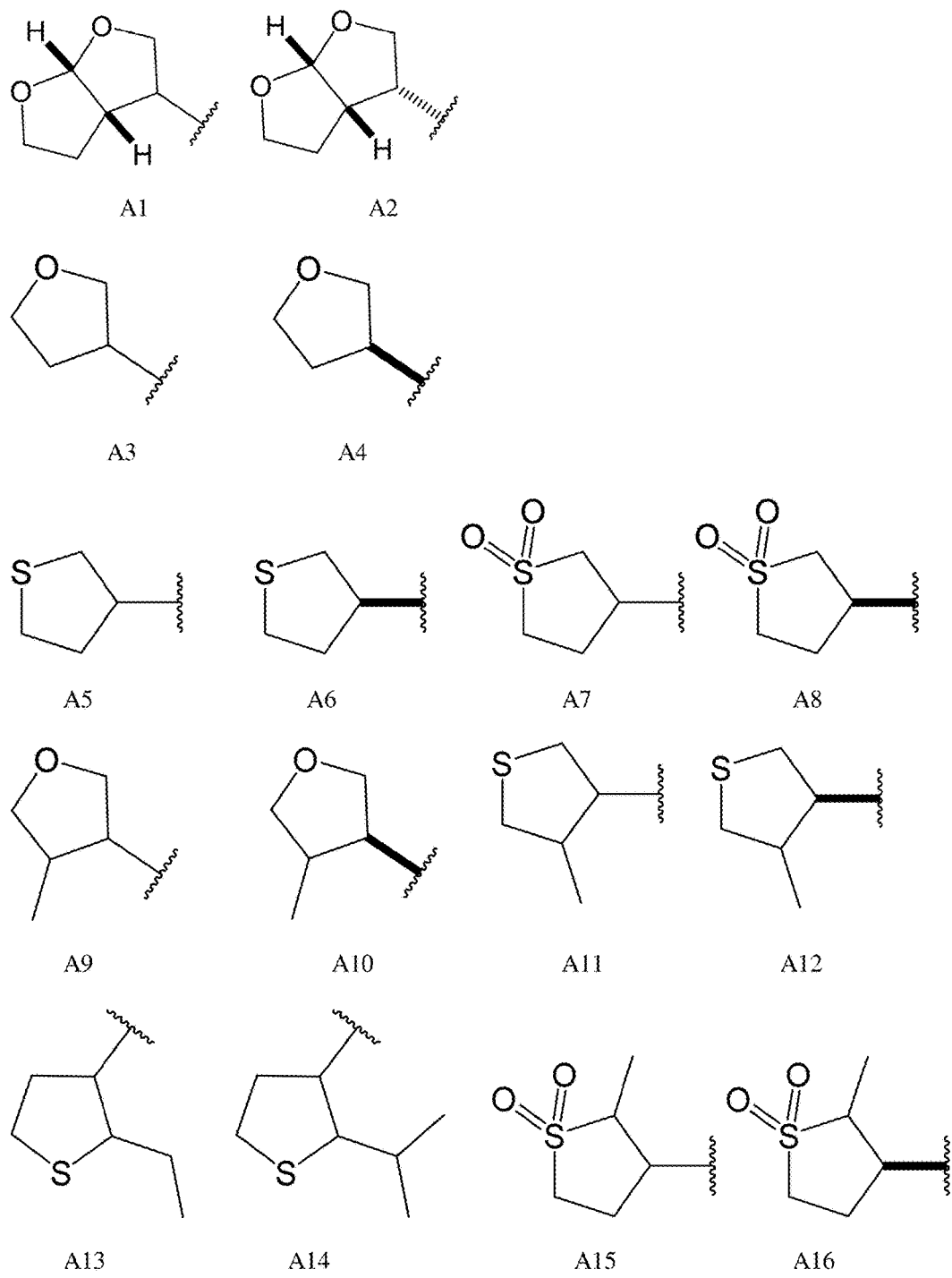
FIGS. 4A-4D list representative A groups for compounds of the invention including A1-A53.
Figure 4B:
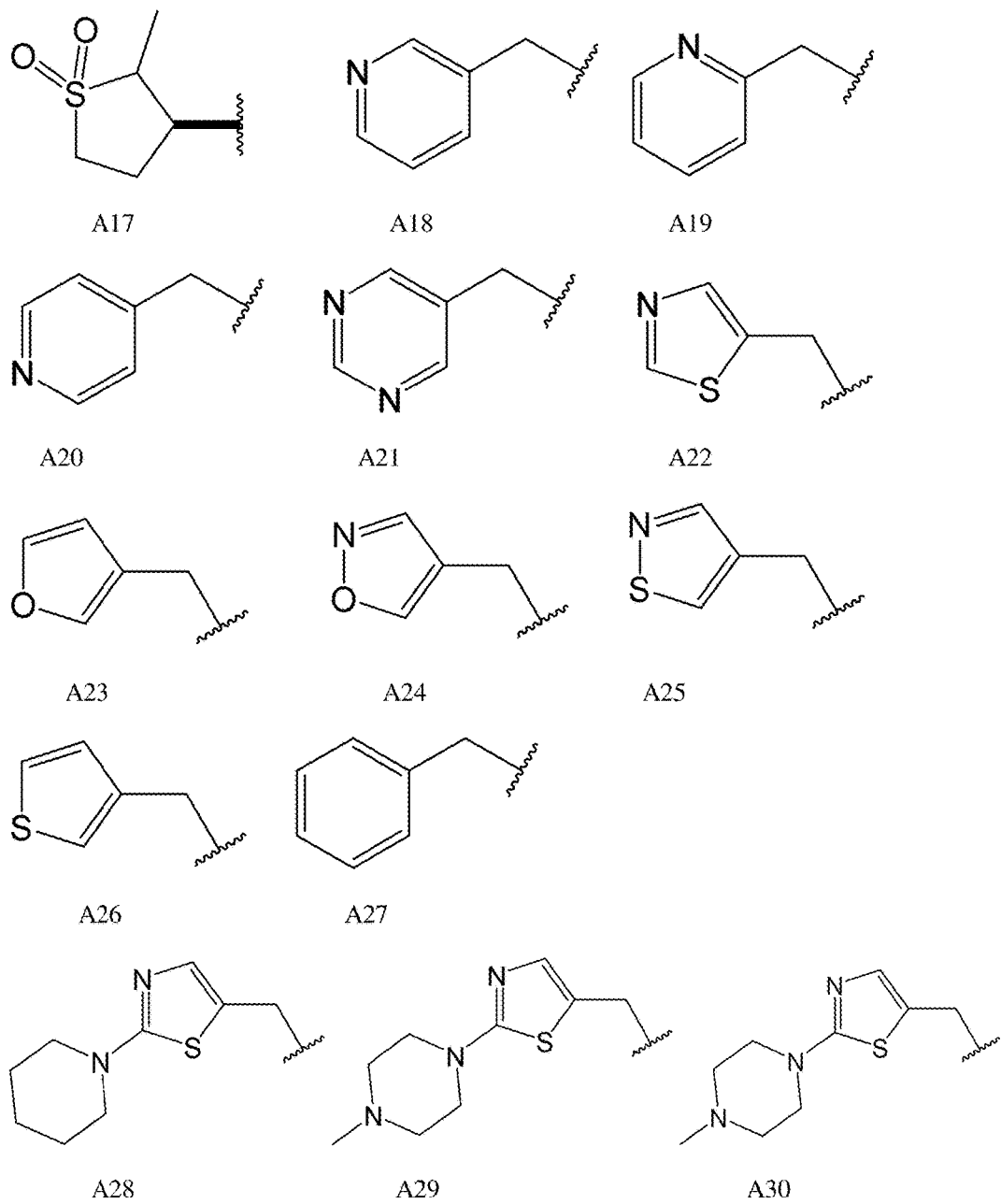
Figure 4C:
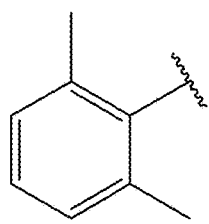
Figure 4C:
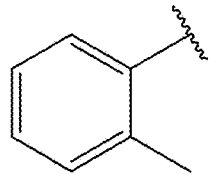
Figure 4C:
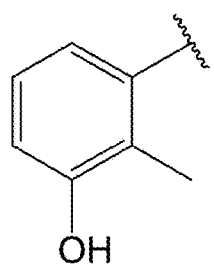
Figure 4C:
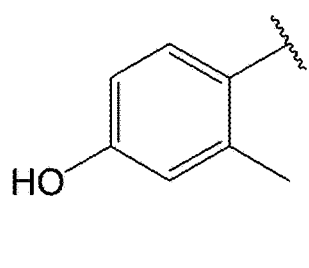
Figure 4C:
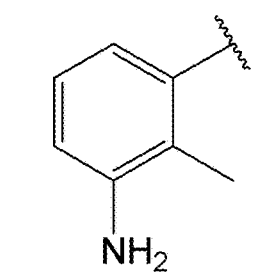
Figure 4C:
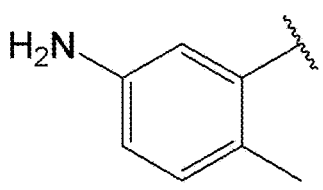
Figure 4C:
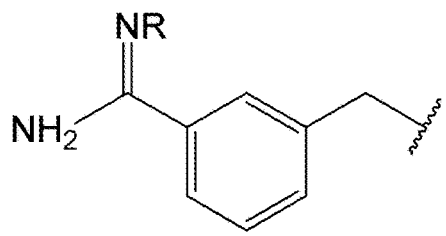
Figure 4C:
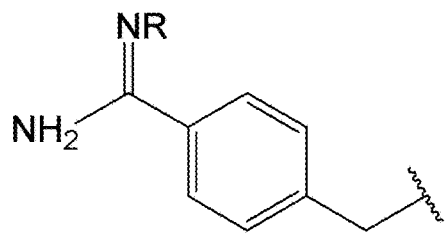
Figure 4C:
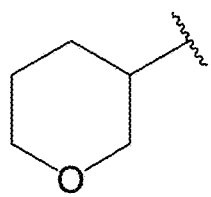
Figure 4C:
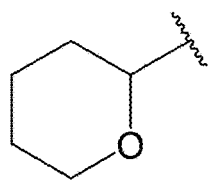
Figure 4C:
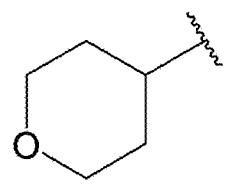
Figure 4C:
Figure 4D:
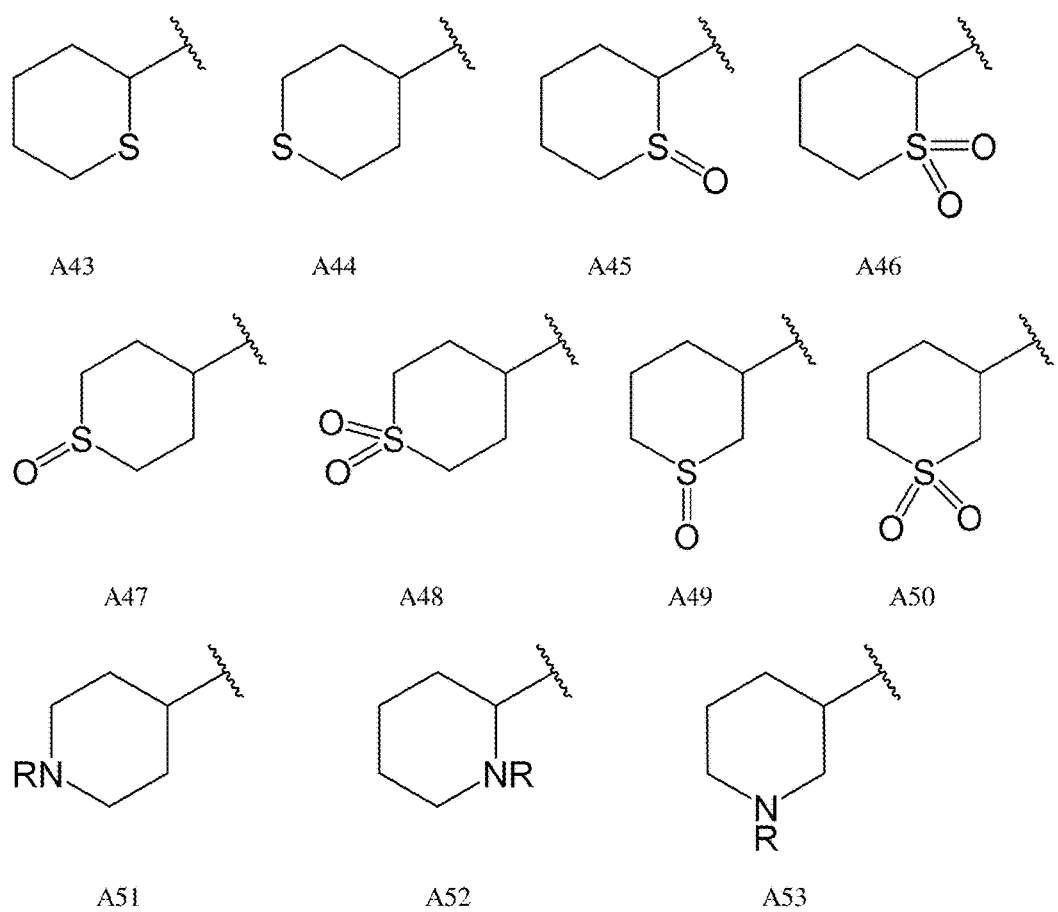

The ability of B-darunavir to inhibit the cytopathic toxicity of HIV was determined by standard methods (11). Briefly, both human lymphocyte cell line MT-4 and plasmid pNL4-3, which directs the production of infectious virions (12), were obtained from the NIH AIDS Reagent Program. Prior to viral studies, the toxicity of B-darunavir for MT-4 cells was evaluated, and B-darunavir was found not to cause a significant inhibition of the growth of MT-4 cells at concentrations up to 1 mM. Then, MT-4 cells were transfected with plasmid pNL4-3. Maximal virus production was detected on Day 6 post-transfection. Viral inhibition assays were conducted with 25,000 MT-4 cells in 200 μL of RPMI medium containing fetal bovine serum (10% v/v). Infections were conducted with virus at 100×TCID$_{50}$ by resuspending pelleted cells in 500 μL of virus-containing medium and incubating for 4 h prior to plating with B-darunavir. After 7 days, the loss of HIV cytopathic toxicity was assessed by measuring cell viability using the MTS assay from Promega (Madison, Wis.). The results show that B-darunavir at a concentration of ≥100 nM inhibits the toxicity of HIV for human lymphocytes (FIG. 3).

REFERENCES

1. Surleraux, D. L., Tahri, A., Verschueren, W. G., Pille, G. M., de Kock, H. A., Jonckers, T. H., Peeters, A., De Meyer, S., Azijn, H., Pauwels, R., de Bethune, M. P., King, N. M., Prabu-Jeyabalan, M., Schiffer, C. A., Wigerinck, P. B. *J. Med. Chem.* 2005, 48, 1813-1822.
2. Honda, Y., Katayama, S., Kojima, M., Suzuki, T., Kishibata, N., Izawa, K. *Org. Biomol. Chem.* 2004, 2, 2061-2070.
3. Tie, Y., Boross, P. I., Wang, Y.-F., Gaddis, L., Hussain, A. K., Leshchenko, S., Ghosh, A. K., Louis, J. M., Harrison, R. W., Weber, I. T. *J. Mol. Biol.* 2004, 338, 341-352.
4. Gibson, D. G., Young, L., Chuang, R., Venter, J. C., Hutchison III, C. A., Smith, H. A. *Nat. Meth.* 2009, 6, 343-345
5. Hui, J. O., Tomasselli, A. G., Reardon, I. M., Lull, J. M., Brunner, D. P., Tomich, C. C., Heinrikson, R. L. *J. Protein Chem.* 1993, 3, 323-327.
6. Matayoshi, E. D., Wang, G. T., Krafft, G. A., Erickson, J. *Science.* 1990, 247, 954-958
7. Altman, M. D., Ali, A., Reddy, G. S., Nalam, M. N., Anjum, S. G., Cao, H., Chellappan, S., Kairys, V., Fernandes, M. X., Gilson, M. K., Schiffer, C. A., Rana, T. M., Tidor, B. *J. Am. Chem. Soc.* 2008, 130, 6099-6113.
8. Ghosh, A. K., Sridhar, P. R., Leshchenko, S., Hussain, A. K., Li, J., Kovalevsky, A. Y., Walters, D. E., Wedekind, J. E., Grum-Tokars, V., Das, D., Koh, Y., Maeda, K., Gatanaga, H., Weber, I. T., Mitsuya, H. *J. Med. Chem.* 2006, 49, 5252-5261.
9. Jones, S. and Selitsianos, D. "A Simple and Effective Method for Phosphoryl Transfer Using TiCl$_4$ Catalysis" Organic Letts 2002, 4 (21), 3671-3673.
10. Plourde, R., d'Alarcao, M. "Synthesis of a Potentially Insulin-Mimetic Phosphodissaccharide" Tetrahedron Letts, 31(19), 2693-2696.
11. Yoshimura, K.; Kato, R.; Kavlick, M. F.; Nguyen, A.; Maroun, V.; Maeda, K.; Hussain, K. A.; Ghosh, A. K.; Gulnik, S. V.; Erickson, J. W.; Mitsuya, H. A potent human immunodeficiency virus type 1 protease inhibitor, UIC-94003 (TMC-126), and selection of a novel (A28S) mutation in the protease active site. J. Virol. 2002, 76, 1349-1358.
12. Adachi, A; Gendelman, H. E.; Koenig, S.; Folks, T.; Willey, R.; Rabson, A.; Martin, M. A. Production of acquired immunodeficiency syndrome-associated retrovirus in human and nonhuman cells transfected with an infectious molecular clone. J. Virol. 1986, 59, 284-291.
13. T. Mancilla, R. Contreras and B. Wrackmeyer, J. Organomet. Chem. 1986, 307, 1â€"6
14. E. P. Gillis and M. D. Burke (2007) "A Simple and Modular Strategy for Small Molecule Synthesis: Iterative Suzuli-Miyaura Coupling of B-Protected Haloboroanic Acid Building Blocks," J. Am. Chem. Soc.: 129, 6716-6717.
15. E. P. Gillis and M. D. Burke (2009) "Iterative Cross-Coupling with NIDA Boronates: towards a General Strategy for Small-Molecule Synthesis," Aldrichimica Acta: 42, 17-27.
16. D. M. Knapp, E. P. Gillis and M. D. Burke (2009) "A General Solution for Unstable Boronic Acids: Slow-Release Cross-Coupling from Air-Stable MIDA Boronates", J. Am. Chem. Soc. 2009, 131, 6961-6963.

We claim:
1. A compound of formula:

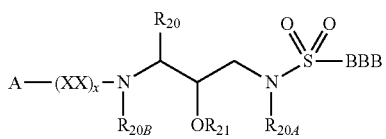

or a pharmaceutically acceptable salt, ester, or solvate thereof,
wherein:
x is 0 or 1 to show the presence or absence of —XX—; —XX—, when present, is —O—, —CO—, —SO$_2$—, —CO—CO—, —O—CO—, —O—SO$_2$—, —NR$_{10}$—SO$_2$—, —NR$_{10}$—CO— or —NR$_{10}$—CO—CO—, where each R$_{10}$ is independently H, C1-C4 alkyl or C1-C4 alkyl substituted with C3-C7 cycloalkyl;
R$_{20}$, and R$_{20A}$ are independently selected from C1-C4 alkyl, C3-C6 cycloalkyl, C5-C6-cycloalkenyl, phenyl, C1-C4 alkyl substituted with one or more phenyl, or substituted with one or more C3-C6 cycloalkyl groups, a C3-C6 cycloalkyl group substituted with or fused to a phenyl, and a C5-C6 cycloalkyl group substituted with or fused to a phenyl; R$_{20B}$ is independently selected from hydrogen, C1-C4 alkyl, C3-C6 cycloalkyl, C5-C6-cycloalkenyl, phenyl, C1-C4 alkyl substituted with one or more phenyl, or substituted with one or more C3-C6 cycloalkyl groups, a C3-C6 cycloalkyl group substituted with or fused to a phenyl, and a C5-C6 cycloalkyl group substituted with or fused to a phenyl;
R$_{21}$ is selected from H, —PO$_3$H$_2$, —PO$_3$H$^-$, —PO$_3{}^{2-}$, —CH$_2$—OPO$_3$H$_2$, —CH$_2$—OPO$_3$H$^-$, —CH$_2$—OPO$_3{}^{2-}$, —PO$_3$(R$_{31}$)$_2$, —PO$_3$R$_{31}$H, and pharmaceutically acceptable salts thereof, where R$_{31}$ is optionally substituted C1-C6 alkyl or optionally substituted C6-C10 aryl, and —CO—R$_{22}$, where R$_{22}$ is selected from C1-C4 alkyl, C2-C4 alkenyl, C2-C10 alkyl, wherein one or more —CH$_2$— groups are replaced with —O—, and a C2-C10 alkyl, wherein one or more —CH$_2$— groups are replaced with —NH— or one or more —CH$_3$ groups are replaced with —NR$_{23}$, where R$_{23}$ is H or a C1-C4 alkyl; and
A is selected from H, Het, C6-C10 aryl, C3-C7 cycloalkyl, C5-C7 cycloalkenyl, C1-C4 alkyl, C2-C4 alkenyl, and C1-C4 alkyl substituted with one or more C1-C4 alkoxy, C3-C7 cycloalkyl, C5-C7 cycloalkenyl, C6-C10 aryl, or Het group,
wherein Het is a 5-10 membered saturated, partially saturated or unsaturated cyclic group containing one or more heteroatoms or moieties selected from —N=, —N(R$_{24}$)—, —O—, —S—, —SO—, —SO$_2$—, and —CO—, where R$_{24}$ is selected from H, C1-C4 alkyl, C1-C4 alkyl substituted with a C3-C7 cycloalkyl group, and C1-C4 alkyl substituted with a C6-C10 aryl group;

wherein each R$_{20}$, R$_{22}$, R$_{23}$, R$_{24}$, R$_{31}$, A or Het group is optionally substituted with one or more oxo, C1-C3 alkoxy, —OH, C1-C3 alkyl, —CO—R$_{25}$, —N(R$_{25}$)$_2$, —CO$_2$R$_{25}$, —NR$_{25}$—CO—R$_{25}$, —CO—N(R$_{25}$)$_2$, —(CH$_2$)$_r$—OH, where r is 1 or 2, —CN, —NO$_2$, halo or —CF$_3$, where R$_{25}$ is H or C1-C3 alkyl; and
BBB is

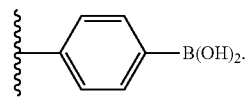

2. The compound, salt, ester, or solvate of claim 1, wherein XX is present, x is 1 and is —O—, —CO—, —SO$_2$— or —O—CO—.
3. The compound, salt, ester, or solvate of claim 1, wherein A is a 5-10 membered saturated, partially saturated or unsaturated cyclic group containing one or more heteroatoms or moieties selected from —N=, —N(R$_{24}$)—, —O—, —S—, —SO—, —SO$_2$—, and —CO—, where R$_{24}$ is selected from H, C1-C4 alkyl, C1-C4 alkyl substituted with a C3-C7 cycloalkyl group, and C1-C4 alkyl substituted with a C6-C10 aryl group.
4. The compound, salt, ester, or solvate of claim 1, wherein XX is present, x is 1 and is —O—CO—, R$_{20}$ is a benzyl group, R$_{20A}$ is C1-C4 alkyl and R$_{20B}$ is hydrogen.
5. A pharmaceutical composition comprising a therapeutically effective amount of a compound, salt, ester, or solvate of claim 1 and a pharmaceutically acceptable carrier.
6. A pharmaceutical composition comprising a therapeutically effective amount of a compound, salt, ester, or solvate of claim 1 and a pharmaceutically acceptable carrier and further comprising ritonovir.
7. The compound, salt, ester, or solvate of claim 4, where R$_{21}$ is selected from hydrogen, —PO$_3$H$_2$, —PO$_3$H$^-$, —PO$_3{}^{2-}$, —CH$_2$—OPO$_3$H$_2$, —CH$_2$—OPO$_3$H$^-$, —CH$_2$—OPO$_3{}^{2-}$, —PO$_3$(R$_{31}$)$_2$, —PO$_3$R$_{31}$H, and pharmaceutically acceptable salts thereof, where R$_{31}$ is optionally substituted C1-C6 alkyl or optionally substituted C6-C10 aryl.
8. The compound, salt, ester, or solvate of claim 7, where A is selected from A1-A4 of formulae:

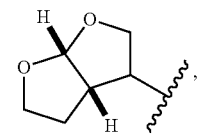

A1

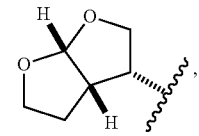

A2

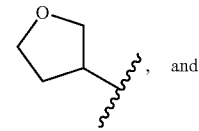

, and

A3

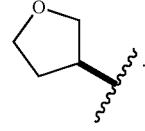

A4

9. The compound, salt, ester, or solvate of claim 7, where A is A2 or A4 of formulae:

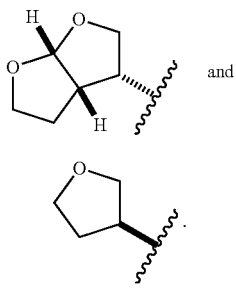

10. The compound, salt, ester, or solvate of claim 9 of formula:

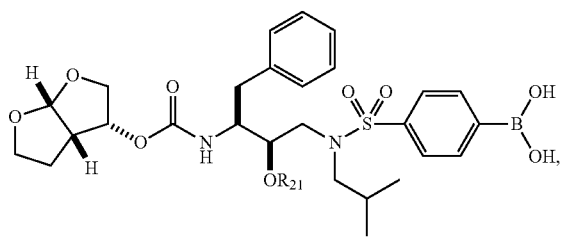

where $R_{21}$ is hydrogen, —$PO_3H_2$ or pharmaceutically acceptable salts thereof.

11. The compound, salt, ester, or solvate of claim 7, where A is A2 or A4 of formulae:

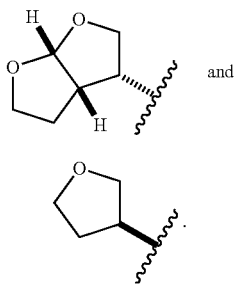

12. The compound claim 1 which is selected from:

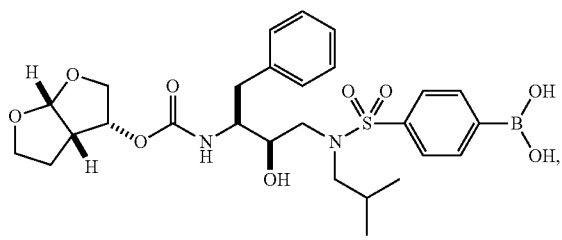

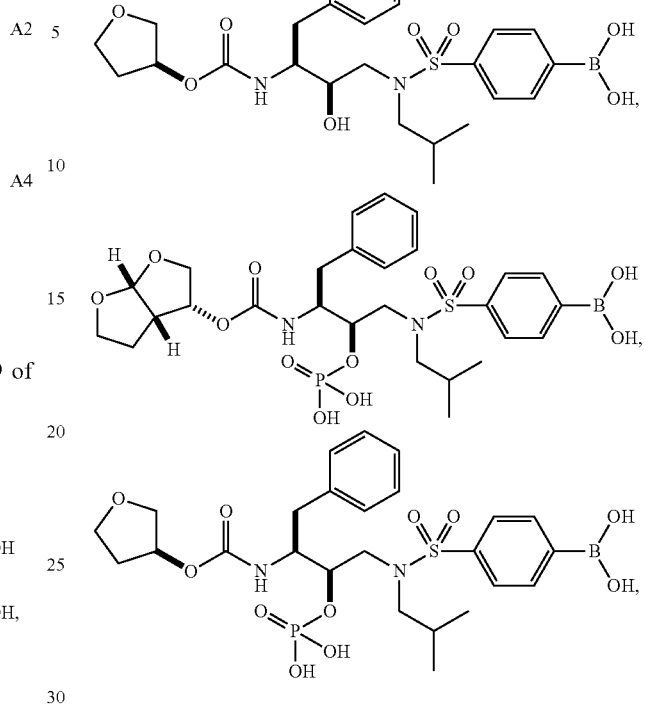

or a salt, ester, or solvate thereof.

13. The compound of claim 1 of formula:

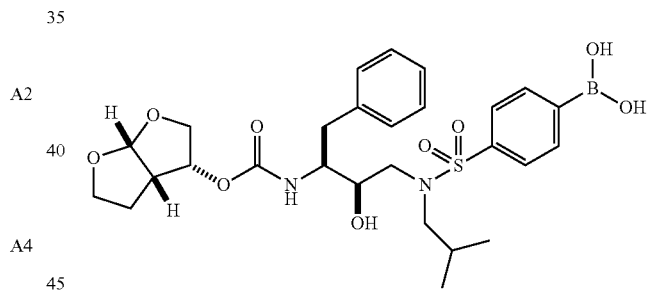

or a salt, ester, or solvate thereof.

14. The compound of claim 1 of formula:

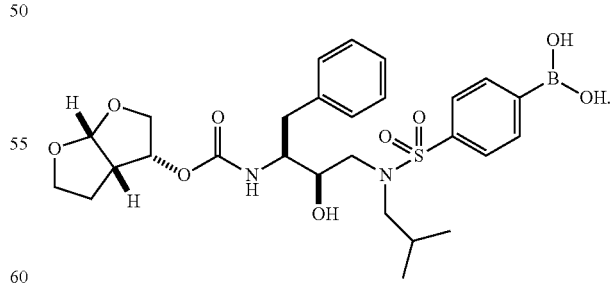

* * * * *

UNITED STATES PATENT AND TRADEMARK OFFICE
CERTIFICATE OF CORRECTION

PATENT NO. : 9,738,664 B2  
APPLICATION NO. : 14/927390  
DATED : August 22, 2017  
INVENTOR(S) : Ronald T. Raines et al.

Page 1 of 1

It is certified that error appears in the above-identified patent and that said Letters Patent is hereby corrected as shown below:

At Column 68 Line 16 (Claim 2), replace "wherein XX is present, x is 1 and is –O–" with -- wherein x is 1 and XX is –O– --.

At Column 68 Line 26 (Claim 4), replace "wherein XX is present, x is 1 and is –O–" with -- wherein x is 1 and XX is –O– --.

Signed and Sealed this
Fifth Day of June, 2018

Andrei Iancu
*Director of the United States Patent and Trademark Office*